(12) United States Patent
Drumheller et al.

(10) Patent No.: US 11,839,698 B2
(45) Date of Patent: *Dec. 12, 2023

(54) DRUG COMPOSITION AND COATING

(71) Applicant: W. L. Gore & Associates, Inc., Newark, DE (US)

(72) Inventors: Paul D Drumheller, Flagstaff, AZ (US); Robert L. Cleek, Flagstaff, AZ (US); Todd J. Johnson, Flagstaff, AZ (US); Theresa A. Holland, Flagstaff, AZ (US)

(73) Assignee: W. L. Gore & Associates, Inc., Newark, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/210,118

(22) Filed: Mar. 13, 2014

(65) Prior Publication Data
US 2015/0258251 A1   Sep. 17, 2015

(51) Int. Cl.
| | | |
|---|---|---|
| *A61L 27/54* | (2006.01) |
| *A61L 31/08* | (2006.01) |
| *A61L 29/16* | (2006.01) |
| *A61L 29/08* | (2006.01) |
| *A61L 27/28* | (2006.01) |
| *A61K 31/337* | (2006.01) |
| *A61K 31/727* | (2006.01) |
| *A61K 45/06* | (2006.01) |
| *A61K 31/436* | (2006.01) |
| *A61L 31/16* | (2006.01) |
| *A61L 31/10* | (2006.01) |
| *A61F 2/07* | (2013.01) |
| *A61F 2/915* | (2013.01) |
| *A61L 31/04* | (2006.01) |
| *A61L 33/00* | (2006.01) |
| *A61L 33/04* | (2006.01) |
| *A61L 33/06* | (2006.01) |

(52) U.S. Cl.
CPC ............... *A61L 27/54* (2013.01); *A61F 2/07* (2013.01); *A61F 2/915* (2013.01); *A61K 31/337* (2013.01); *A61K 31/436* (2013.01); *A61K 31/727* (2013.01); *A61K 45/06* (2013.01); *A61L 27/28* (2013.01); *A61L 29/08* (2013.01); *A61L 29/085* (2013.01); *A61L 29/16* (2013.01); *A61L 31/048* (2013.01); *A61L 31/08* (2013.01); *A61L 31/10* (2013.01); *A61L 31/16* (2013.01); *A61L 33/0035* (2013.01); *A61L 33/0076* (2013.01); *A61L 33/04* (2013.01); *A61L 33/064* (2013.01); *A61L 2300/216* (2013.01); *A61L 2300/416* (2013.01); *A61L 2300/42* (2013.01); *A61L 2300/602* (2013.01); *A61L 2300/606* (2013.01); *A61L 2300/61* (2013.01); *A61L 2420/02* (2013.01); *A61L 2420/06* (2013.01)

(58) Field of Classification Search
None
See application file for complete search history.

(56) References Cited

U.S. PATENT DOCUMENTS

| | | |
|---|---|---|
| 3,953,566 A | 4/1976 | Gore |
| 4,187,390 A | 2/1980 | Gore |
| 4,526,714 A | 7/1985 | Feijen et al. |
| 4,613,665 A | 9/1986 | Larm |
| 5,061,750 A | 10/1991 | Feijen et al. |
| 5,876,432 A | 3/1999 | Lau et al. |
| 6,299,604 B1 | 10/2001 | Ragheb et al. |
| 6,461,665 B1 | 10/2002 | Scholander |
| 6,653,457 B1 | 11/2003 | Larm et al. |
| 6,743,388 B2 | 6/2004 | Sridharan et al. |
| 7,049,380 B1 | 5/2006 | Chang et al. |
| 7,659,219 B2 | 2/2010 | Biran et al. |
| 7,819,914 B2 | 10/2010 | Dave et al. |
| 8,048,440 B2 | 11/2011 | Chang et al. |
| 8,048,503 B2 | 11/2011 | Farnsworth et al. |
| 8,658,707 B2 | 2/2014 | Xu et al. |
| 8,753,386 B2 | 6/2014 | Shaw |

(Continued)

FOREIGN PATENT DOCUMENTS

| | | |
|---|---|---|
| CA | 2484269 A1 | 11/2003 |
| CN | 103691007 A | 4/2014 |

(Continued)

OTHER PUBLICATIONS

Y. Jeffrey Wu et al., Acetaminophen Enhances Cisplatin- and Paclitaxel-mediated Cytotoxicity to SKOV3 Human Ovarian Carcinoma, 33(6) Anticancer Res., 2391-400 (2013).*
International Search Report, PCT/US2014/027304, 5 pages.
Aggarwal, Solid Dispersion as an Eminent Strategic Approach in Solubility Enhancement of Poorly Soluble Drugs, International Journal of Pharmaceutical Sciences and Research, 2010, vol. 1 (8), pp. 1-13.
Albers, Evaluation of Predictive Models for Stable Solid Solution Formation, Journal of Pharmaceutical Sciences, 2011, vol. 100(2), pp. 667-680.

(Continued)

*Primary Examiner* — Patricia Duffy
*Assistant Examiner* — Garen Gotfredson

(57) ABSTRACT

According to the invention there is provided inter alia a medical device for delivering a therapeutic agent to a tissue, the device having a solid surfactant-free particulate coating layer applied to a surface of the device, the coating layer comprising a therapeutic agent and at least one non-polymeric organic additive which is hydrolytically stable; wherein at least a proportion of the particulate coating layer comprising the therapeutic agent and the at least one organic additive melts as a single phase at a lower temperature than the melting point of the therapeutic agent and the at least one organic additive when in pure form; wherein the therapeutic agent is paclitaxel; and wherein the therapeutic agent, when formulated in the coating layer, is stable to sterilization.

40 Claims, 9 Drawing Sheets

(56) References Cited

U.S. PATENT DOCUMENTS

| | | |
|---|---|---|
| 8,784,862 B2 | 7/2014 | Horres et al. |
| 8,887,477 B2 | 11/2014 | Falotico et al. |
| 8,926,688 B2 | 1/2015 | Burkart et al. |
| 8,927,049 B2 | 1/2015 | Dave et al. |
| 2003/0204168 A1 | 10/2003 | Bosma et al. |
| 2004/0024448 A1 | 2/2004 | Chang et al. |
| 2004/0127551 A1 | 7/2004 | Zhang et al. |
| 2005/0055078 A1 | 3/2005 | Campbell |
| 2006/0067977 A1 | 3/2006 | Labrecque et al. |
| 2006/0287712 A1 | 12/2006 | Eidenschink |
| 2007/0207186 A1 | 9/2007 | Scanlon et al. |
| 2007/0212547 A1 | 9/2007 | Fredrickson |
| 2008/0057101 A1 | 3/2008 | Roorda |
| 2008/0057102 A1 | 3/2008 | Roorda |
| 2008/0057103 A1 | 3/2008 | Roorda |
| 2008/0118544 A1 | 5/2008 | Wang |
| 2008/0175980 A1* | 7/2008 | Sun .............................. 427/2.25 |
| 2008/0255508 A1 | 10/2008 | Wang |
| 2009/0076587 A1 | 3/2009 | Cully et al. |
| 2009/0118822 A1* | 5/2009 | Holman ................... A61L 31/12 623/1.49 |
| 2009/0148496 A1 | 6/2009 | Schmitz et al. |
| 2009/0182413 A1 | 7/2009 | Burkart et al. |
| 2009/0228097 A1 | 9/2009 | Wang |
| 2010/0015200 A1 | 1/2010 | McClain et al. |
| 2010/0152841 A1 | 6/2010 | Dave et al. |
| 2010/0161039 A1 | 6/2010 | Dave et al. |
| 2010/0209472 A1 | 8/2010 | Wang |
| 2010/0222311 A1 | 9/2010 | Thommes et al. |
| 2010/0239635 A1 | 9/2010 | McClain et al. |
| 2010/0241220 A1 | 9/2010 | McClain et al. |
| 2010/0256748 A1 | 10/2010 | Taylor et al. |
| 2010/0268321 A1 | 10/2010 | McDermott et al. |
| 2010/0272778 A1 | 10/2010 | McClain et al. |
| 2011/0113728 A1 | 5/2011 | Falotico et al. |
| 2011/0144578 A1 | 6/2011 | Pacetti et al. |
| 2011/0238011 A1 | 9/2011 | Scheller et al. |
| 2012/0172787 A1 | 7/2012 | McClain et al. |
| 2012/0252125 A1 | 10/2012 | Puntambekar |
| 2012/0277843 A1 | 11/2012 | Weber et al. |
| 2012/0303112 A1 | 11/2012 | Armstrong et al. |
| 2012/0310210 A1 | 12/2012 | Campbell et al. |
| 2013/0004548 A1 | 1/2013 | Klocke et al. |
| 2013/0142834 A1 | 6/2013 | Esfand et al. |
| 2013/0189329 A1 | 7/2013 | Wang |
| 2013/0231733 A1 | 9/2013 | Knisley et al. |
| 2013/0253426 A1 | 9/2013 | Campbell et al. |
| 2014/0086971 A1 | 3/2014 | Hall et al. |
| 2014/0135897 A1 | 5/2014 | Cully et al. |
| 2014/0142682 A1 | 5/2014 | Radspinner |
| 2014/0277381 A1 | 9/2014 | Zukowski |
| 2016/0000977 A1 | 1/2016 | Drumheller et al. |
| 2016/0015868 A1 | 1/2016 | Drumheller et al. |
| 2016/0015870 A1 | 1/2016 | Drumheller et al. |
| 2017/0014553 A1 | 1/2017 | Antoni et al. |

FOREIGN PATENT DOCUMENTS

| | | |
|---|---|---|
| EP | 0086186 A1 | 8/1983 |
| EP | 0086187 A1 | 8/1983 |
| EP | 0495820 B1 | 5/1995 |
| EP | 1834636 A1 | 9/2007 |
| EP | 2198814 A2 | 6/2010 |
| EP | 2201915 A1 | 6/2010 |
| EP | 2228082 A2 | 9/2010 |
| EP | 2322230 A1 | 5/2011 |
| EP | 2676639 | 12/2013 |
| JP | 2010-501229 A | 1/2010 |
| JP | 2010-142638 A | 7/2010 |
| JP | 2010-540159 A | 12/2010 |
| KR | 10-2011-0057796 A | 6/2011 |
| WO | 2003/074196 A2 | 9/2003 |
| WO | WO2004/000380 | 12/2003 |
| WO | 2007/133699 A2 | 11/2007 |
| WO | 2008/024669 A2 | 2/2008 |
| WO | WO2008/023038 | 2/2008 |
| WO | WO2008/063576 | 5/2008 |
| WO | 2008/086490 A2 | 7/2008 |
| WO | 2008/106223 A1 | 9/2008 |
| WO | WO2009/051614 | 4/2009 |
| WO | 2009/058666 A1 | 5/2009 |
| WO | WO2009/064372 | 5/2009 |
| WO | 2010/029189 A2 | 3/2010 |
| WO | 2011/035001 A2 | 3/2011 |
| WO | 2011/110684 A1 | 9/2011 |
| WO | WO2011/147408 | 12/2011 |
| WO | 2012/123384 A1 | 9/2012 |
| WO | WO2013/021199 | 2/2013 |
| WO | WO2013/074185 | 5/2013 |
| WO | 2013/130377 A1 | 9/2013 |
| WO | 2014/026174 A1 | 2/2014 |
| WO | 2014/107748 A2 | 7/2014 |
| WO | 2014/202645 A1 | 12/2014 |
| WO | 2015/136106 A1 | 9/2015 |

OTHER PUBLICATIONS

Avula, Predicting eutectic behaviour of drugs and excipients by unique calculations, J. Therm. Anal. Calorim. 2010, 99, pp. 655-658.

Avula, Predicting Eutectic Behaviour of Drugs and Excipients by Unique Calculations. Proceedings of the NATAS Annual Conference on Thermal Analysis and Applications 2008, 36th.

Badjatya, Enhancement of Solubility of Paclitaxel by Solid Dispersions Techniques, Asian Journal of Pharmacy & Life Science, 2011, vol. 1(2), pp. 156-160.

Baird, Evaluation and modelling of the eutectic composition of various drug-polyethylene glycol solid dispersions, Pharmaceutical Development and Technology, 2011, 16(3), pp. 201-211.

Brittain, Cocrystal Systems of Pharmaceutical Interest: 2009, Profiles of Drug Substances. Excipients, and Related Methodology, 2011, vol. 36, pp. 361-381.

Camargo, Injectable PLA-based in situ forming implants for controlled release of Ivermectin a BCS Class II drug: solvent selection based on physico-chemical characterization, Drug Development and Industrial Pharmacy, 2013, 39(1). pp 146-155.

Chen, Chiral co-crystal solid solutions: structures, melting point phase diagram, and chiral enrichment of (ibuprofen)2(4,4-dipyridyl), Cryst. Eng. Comm. 2010, 12, pp. 1485-1493.

Cherukuvada, Eutectics as improved pharmaceutical materials: design, properties and characterization, Chem. Comm. 2014, 50, pp. 906-923.

Chiou, Pharmaceutical Applications of Solid Dispersion Systems, Journal of Pharmaceutical Sciences, 1971, vol. 60(9). pp 1281-1302.

Dake, Polymer-free Paclitaxel-coated Zilver PTX Stents—Evaluation of Phamacokinetics and Comparative Safety in Porcine Arteries, Journal of Vascular and Interventional Radiology, 2011, vol. 22(5), pp. 603-610.

Dinge, Eutectic mixtures of drugs with poor aqueous solubility. Solid state characterization and dissolution studies, Dissertation Abstracts International, 2012, 73 No. 9B(E).

Elder, Use of pharmaceutical salts and cocrystals to address the issue of poor solubility, International Journal of Pharmaceutics, 2013, pp. 88-100.

Ford, The Current Status of Solid Dispersions, Pharm. Acta. Helv., 1986, 61(3), pp. 69-88.

Good, Cocrystal Eutectic Constants and Prediction of Solubility Behavior, Crystal Growth and Design Communication 2010, 10, pp. 1028-1032.

Gordon, Raman mapping of pharmaceuticals, International Journal of Pharmaceutics, 2011, 417, pp 151-162.

Gorniak, Phase Diagram and dissolution studies of the fenofibrate-acetylsalicylic acid system, J. Therm. Anal. Calorim. 2011, 104, pp. 1195-1200.

Gorniak, Thermal, spectroscopic, and dissolution studies of the simvastatin-acetylsalicylic acid mixtures, J. Therm. Anal, Calorim. 2013, 111, pp. 2125-2132.

(56) References Cited

OTHER PUBLICATIONS

Goud, Fast dissolving eutectic compositions of curcumin, International Journal of Pharmaceutics, 2012, pp. 63-72.
Gowthamarajan, Dissolution Testing for Poorly Soluble Drugs: A Continuing Perspective, Dissolution Technologies, 2010, pp. 24-32.
Huuskonen, Prediction of drug solubility from molecular structure using a drug-like training set, SAR and QSAR in Environmental Research, 2008, vol. 19 (3-4), pp. 191-212.
Just, Improved group contribution parameter set for the application of solubility parameters to melt extrusion, European Journal of Pharmaceutics and Biopharmaceutics, 2013, pp. 1-9.
Kitamoto, Caffeine diminishes cytotoxic effects of paclitaxel on a human lung adenocarcinoma cell line, Cancer Letters, 2003, 191, pp. 101-107.
Kraitzer, Mechanisms of antiproliferative drug release from bioresorable porous structures, Journal of Biomedical Materials Research A, 2013, 101A(5). pp 1302-1310.
Kreuter, Solid Dispersion and Solid Solution, Topics in Pharmaceutical Sciences, 1983, pp. 359-370.
Lambert, Radiation and Ethylene Oxide Terminal Sterilization Experiences with Drug Eluting Stent Products, AAPS PharmSciTech, 2011, vol. 12(4), pp. 1116-1126.
Lee, Paclitaxel-coated expanded polytetrafluoroethylene haemodialysis grafts inhibit neointimal hyperplasia in porcine model of graft stenosis, Nephrol Dial Transplant, 21-2432-2438 2006.
Liao, Vascular smooth cell proliferation in perfusion culture of porcine carotid arteries, Biochemical and Biophysical Research Communications, 2008, vol. 372(4), pp. 668-673.
Liggins, Solid-state characterization of paclitaxel, Journal of Pharmaceutical Sciences, 1997, vol. 86, pp. 1458-1463.
Lu, Treatments of paclitaxel with poly(vinyl pyrrolidone) to improve drug release from poly(E-carprolactone) matrix for film-based stent, International Journal of Pharmaceutics, 2012, 434, pp. 161-168.
Lu, Controllable biodegradability, drug release behaviour and hemocompatibility of PTX-eluting magnesium stents, Colloids and Surfaces B: Biointerfaces, 2011, 83, pp. 23-28.
Lu, A rapid thermal method for cocrystal screening, Cryst. Eng. Comm. 2008, 10, pp. 665-668.
Luu, High-throughput 96-well solvent mediated sonic blending synthesis and on-plate solid/solution stability characterization of pharmaceutical cocrystals, International Journal of Pharmaceutics, 2013, 441, pp. 356-364.
Meanwell, The Emerging Utility of Co-Crystals in Drug Discovery and Development, Annual Reports in Medicinal Chemistry, 2008, vol. 43, pp. 373-404.
Moes, Development of an oral solid dispersion formulation for use in low-dose metronomic chemotherapy of paclitaxel, European Journal of Pharmaceuticals and Biopharmaceutics, 2013, 83, pp. 87-94.
Mohammed, Hansen solubility parameter as a tool to predict cocrystal formation, International Journal of Pharmaceutics, 2011, 407, pp. 63-71.
Muddukrishna, Preparation and Solid State Characterization of Paclitaxel Cocrystals, Research J. Pharm. and Tech., 2014, 7(1), pp. 64-69.
Newa, Preparation, characterization and in vivo evaluation of ibuprofen binary solid dispersions with poloxamer 188, International Journal of Pharmaceutics, 2007, 343, pp. 228-237.
Scheinert, The Levant I (Lutonix Paclitaxel-Coated Balloon for the Prevention of Femoropopliteal Restenosis) Trial for Femoropopliteal Revascularization, JACC: Cardiovascular Interventions, 2014, vol. 7(1), pp. 10-19.
Scheller, Paclitaxel Balloon Coating, a Novel Method for Prevention and Therapy of Restenosis, Journal of the American Heart Association, 2004, pp. 810-814.
Schierholz, Physico-chemical properties of a rifampicin-releasing polydimethyl-siloxane shunt, Biomaterials, 1997, 18, pp. 635-641.
Shen, Incorporation of paclitaxel solid dispersions with poloxamer188 or polyethylene glycol to tune drug release from poly(e-carprolactone) films, Drug Development and Industrial Pharmacy, 2013, 39(8), pp. 1187-1196.
Shen, Enhanced Intestinal Absorption of Daidzein by Borneol/Menthol Eutectic Mixture and Microemulsion, AAPS PharmSciTech, 2011, 12(4), pp. 1044-1049.
Simamora, Emulsion Formulations for Intravenous Administration of Paclitaxel, PDA Journal of Pharmaceutical Science & Technology, 1998, 52(4), pp. 170-172.
Sohn, Calorimetric investigation of the phase behaviour of the binary system 7-mPEG 5000-succinyloxy-methyloxycarbonyl-Paclitaxel (PP7)/water, e-Polymers, 2005, No. 007, pp. 1-9 (ISSN 1618-7229).
Stoebner, Effect of processing methods on drug release profiles of anti-restenotic self-assembled monolayers, Applied Surface Science, 2012, 258, pp. 5061-5072.
Tajarobi, Dissolution Rate Enhancement of Parabens in PEG Solid Dispersions and its Influence on the Release from Hydrophilic Matrix Tablets, Journal of Pharmaceutical Sciences, 2011, 100(1), pp. 275-283.
Tian, Construction of Drug-Polymer Thermodynamic Phase Diagrams Using Flory-Huggins Interaction Theory: Identifying the Relevance of Temperature and Drug Weight Fraction to Phase Separation within Solid Dispersions, Mol. Pharmaceutics, 2013, 10, pp. 236-248.
Trask, An Overview of Pharmaceutical Cocrystals as Intellectual Property, Molecular Pharmaceutics, 2007, vol. 4(3), pp. 301-309.
Vedantham, Development of a probucol-releasing antithrombogenic drug eluting stent, Journal of Biomedical Materials Research B: Applied Biomaterials, 2012, 100B(4), pp. 1068-1077.
Vella-Zarb, Small Molecule, Big Difference: The Role of Water in the Crystallization of Paclitaxel, Journal of Pharmaceutical Sciences, 2013, vol. 102(2), pp. 674-683.
Vippagunta, Factors Affecting the Formation of Eutectic Solid Dispersions and Their Dissolution Behaviour, Journal of Pharmaceutical Sciences, 2007, vol. 96(2), pp. 294-304.
Yamashita, Detection of Cocrystal Formation Based on Binary Phase Diagrams Using Thermal Analysis, Pharm. Res., 2013, 30, pp. 70-80.
Yazdani, Vascular, Downstream, and Pharmacokinetic Responses to Treatment with a Low Dose Drug-Coated Balloon in a Swine Femoral Artery Model, Catheterization and Cardiovascular Interventions, 2014, 83, pp. 132-140.
Yoon, Establishment of a solvent map for formation of crystalline and amorphous paclitaxel by solvent evaporation process, Korean J. Chem. Eng., 2011, 28(9), 1918-1923.
Yuan, Influence of Physicochemical Properties on the In Vitro Skin Permeation of Enantiomers, Racemate, and Eutectics of Ibuprofen for Enhanced Transdermal Drug Delivery, Journal of Pharmaceutical Sciences, 2013, 102(6), pp. 1957-1969.
Zhang, Crystalline and Amorphous Solids, Developing Solid Oral Dosage Forms: Pharmaceutical Theory and Practice; Chapter 2.
Criado etal."Early Experience with the Talent(Trademark) Stent-Grall System for Endoluminal Repair of Abdominal Aortic Aneurysms" Peripheral Interventions, 2000, 27(2), pp. 128-135.
Ekdahl et al. "Evaluation of the Blood Compatibility of Materials, Cells, and Tissues: Basic Concepts, Test Models, and Practical Guidelines" Advances in Experimental Medicine and Biology, 2013, Chapter 18, pp. 257-270.
International Preliminary Report on Patentability received for PCT Patent Application No. PCT/US2014/027304, dated Sep. 22, 2016, 10 pages.
International Preliminary Report on Patentability received for PCT Patent Application No. PCT/US2015/020390, dated Sep. 22, 2016, 9 pages.
International Search Report and Written Opinion received for PCT Patent Application No. PCT/US2015/020390, dated Jul. 10, 2015, 11 pages.
Lappegerd et al. "The artificial surface-induced whole blood inflammatory reaction revealed by increases in a series of chemokines and growth factors is largely complement dependent" Journal of Biomedical Materials Research Part A, 2008, 87A(1), pp. 129-135.

(56) References Cited

OTHER PUBLICATIONS

Larsen et al. "Assay of plasma heparin using thrombin and the chromogenic substrate H-D-Phe-Pip-Arg-pNA (S-2238)" Thrombosis Research, 1978, 13(2), pp. 285-288.
Pasche et al. "Binding of Antithrombin to Immobilized Heparin Under Varying Flow Conditions" Artificial Organs, 1991, 15(6), pp. 481-491.
Raungaard et al. "Zotarolimus-eluting durable-polymer-coated stent versus a biolimus-eluting biodegradable-polymer-coated stent in unselected patients undergoing percutaneous coronary intervention (Sort Out VI): a randomised non-inferiority trial" The Lancet, 2015, pp. 1-10.
Smith et al. "Quantitation of Glycosaminoglycan Hexosamine Using 3-Methyl-2-Benzothiazolone Hydrazone Hydrochloride" Analytical Biochemistry, 1979, 98(2), pp. 478-480.

\* cited by examiner

DRUG COMPOSITION AND COATING

FIELD OF THE INVENTION

The present invention relates to solid paclitaxel compositions, medical devices with coatings comprising solid paclitaxel compositions and to methods for making such compositions and coatings.

BACKGROUND OF THE INVENTION

It has become increasingly common to treat a variety of medical conditions by introducing a medical device into the vascular system within a human. For example, medical devices used for the treatment of vascular disease include stents, stent-grafts, grafts, catheters, balloon catheters, guide wires, cannulas and the like.

In the case of a localized vascular disease, a systemic administration of a drug may not be desirable because the drug may have unwanted effects on parts of the body which are not to be treated, or because treatment of the diseased vasculature requires a high concentration of drug that may not be achievable by systemic administration. It is therefore often desirable to administer drugs in a localized manner to vascular tissues. Several devices for localized drug delivery are known, including a stent coated with an elutable drug, also known as a drug eluting stent (DES), and a balloon catheter coated with an elutable drug, also known as a drug eluting balloon (DEB).

DESs are coated with the drug using a variety of coating techniques. When the DES is inserted into a vascular organ, the drug may be slowly released into the surrounding vascular tissue, to provide a long lasting therapeutic effect. Alternatively, the drug may be rapidly released from the coating, with minimal drug remaining on the stent shortly after implantation. Coatings with fast drug release characteristics are particularly advantageous if a medical device is not permanently implanted, as it is necessary in this situation to rapidly deliver drug to the vascular tissue at the time of treatment. An example of such a device is a DEB.

Non-stent based local delivery systems, such as DEBs, have also been effective in the treatment of vascular disease. The DEB is coated with drug using a variety of coating techniques. Therapy commences when the DEB is inserted into the patient to a target site, and inflated at the target site, wherein the DEB is pressed against the vascular tissue to deliver the drug. When DEBs are used, it is advantageous for the drug in the coating to be retained on the balloon surface prior to inflation, and to be rapidly released and transferred to the vascular tissue upon inflation. One of the potential drawbacks to the use of a DEB for the localized treatment of vascular disease, is the unintended release of drug away from the target site. This unintended release may occur during removal from the packaging and insertion into the body, tracking to and placement at the treatment site, during expansion of the balloon, or occur post-treatment as the device is withdrawn from the body. Such unintended release may result from physical dislodgement of the coating and particulation, drug diffusion, device contact with areas proximate the treatment site, or washing out of the drug from the surface of the balloon due to blood flow. Another potential drawback to the use of DEBs for the localized treatment of vascular disease, is the possibility that the drug adheres too strongly to the balloon surface during device inflation, such that the balloon may be deflated and withdrawn before the drug can be released and absorbed by vascular tissues. Therefore, the quantity of drug that is delivered to the target vascular tissue may be too low and difficult to measure or predict, and the application of drug to the vascular tissue may be non-uniform.

A drug commonly used for the localized treatment of vascular disease is paclitaxel. Paclitaxel can be coated onto a DEB using a variety of coating techniques. One technique involves combining the paclitaxel with an excipient, either in dry form using powder methods, or in solution or in suspension using solvent methods. The paclitaxel-excipient combination is then applied to the surface of the DEB, either in the form of a powder or via the application of the solution or suspension followed by a drying step.

There are numerous factors that must be considered when creating a paclitaxel-excipient combination, and when coating the combination onto a medical device such as a DEB. In general, combining drugs and excipients, and coating medical devices with drug-excipient combinations, are complicated areas of technology. They involve the usual formulation challenges, such as those of oral or injectable pharmaceuticals, together with the added challenge of maintaining drug adherence to the medical device until it reaches the target site and subsequently delivering the drug to the target tissues with the desired release and absorption kinetics. DEB coatings generally contain little to no components in the form of a liquid, which typically are often used to stabilize drugs. International application WO2009/051614 (Lutonix, Inc.) discloses a coating comprising a therapeutic agent and an additive that has both a hydrophilic part and a drug affinity part which is said to form an effective drug delivery coating on a medical device without the use of oils and lipids.

A further key requirement is that the therapeutic agent, when formulated in the coatings, must survive a sterilization process essentially intact.

Thus, there is a need to develop paclitaxel-excipient combinations that are appropriate for the localized treatment of vascular disease. In particular there is a need to develop coatings for DEBs and other similar medical devices comprising paclitaxel-excipient combinations that can rapidly deliver paclitaxel in a localized manner to a target vascular tissue to treat a vascular disease. The coating should have good adherence to the DEB while in transit but quickly release the paclitaxel in an effective and efficient manner to the target vascular tissue, where the paclitaxel should rapidly permeate the vascular tissue. The therapeutic agent, when formulated in the coating, should also be stable to sterilization, in particular ethylene oxide sterilization.

For medical devices in which the paclitaxel-excipient is combined on a device that is intended to remain within the body for a period of time, such as stents and stent-grafts, the rapid delivery of the paclitaxel to the target vascular tissue is not an essential feature. However, whether the paclitaxel coating is delivered rapidly, or relatively more slowly, in both cases the coating of such a device should have the same advantageous qualities as those for a DEB, such as good adherence in transit and good paclitaxel stability to sterilization.

SUMMARY OF THE INVENTION

The present inventors have prepared novel paclitaxel-excipient solid compositions which exhibit a depressed melting endotherm. Such paclitaxel-excipient solid compositions have been coated onto a variety of medical devices and demonstrate appropriate adherence thereby reducing the extent of unintentional paclitaxel release during device insertion and tracking, while providing suitable release characteristics of the paclitaxel to the target tissue. The paclitaxel present in the compositions and coatings of the invention is also stable to sterilization, in particular ethylene oxide sterilization. Furthermore, when a paclitaxel-excipient coating was over-coated onto a medical device already coated with immobilized biologically active heparin (as an example of an additional therapeutic agent), following removal of the outer paclitaxel-excipient coating, the heparin activity was preserved.

In one aspect, the invention provides a medical device for delivering a therapeutic agent to a tissue, the device having a solid surfactant-free particulate coating layer applied to an exterior surface of the device, the coating layer comprising a therapeutic agent and at least one non-polymeric organic additive which is hydrolytically stable; wherein at least a proportion of the particulate coating layer comprising the therapeutic agent and the at least one organic additive melts as a single phase at a lower temperature than the melting point of the therapeutic agent and the at least one organic additive when in pure form; wherein the therapeutic agent is paclitaxel; and wherein the therapeutic agent, when formulated in the coating layer, is stable to ethylene oxide sterilization.

DETAILED DESCRIPTION OF THE INVENTION

Figure 1A:
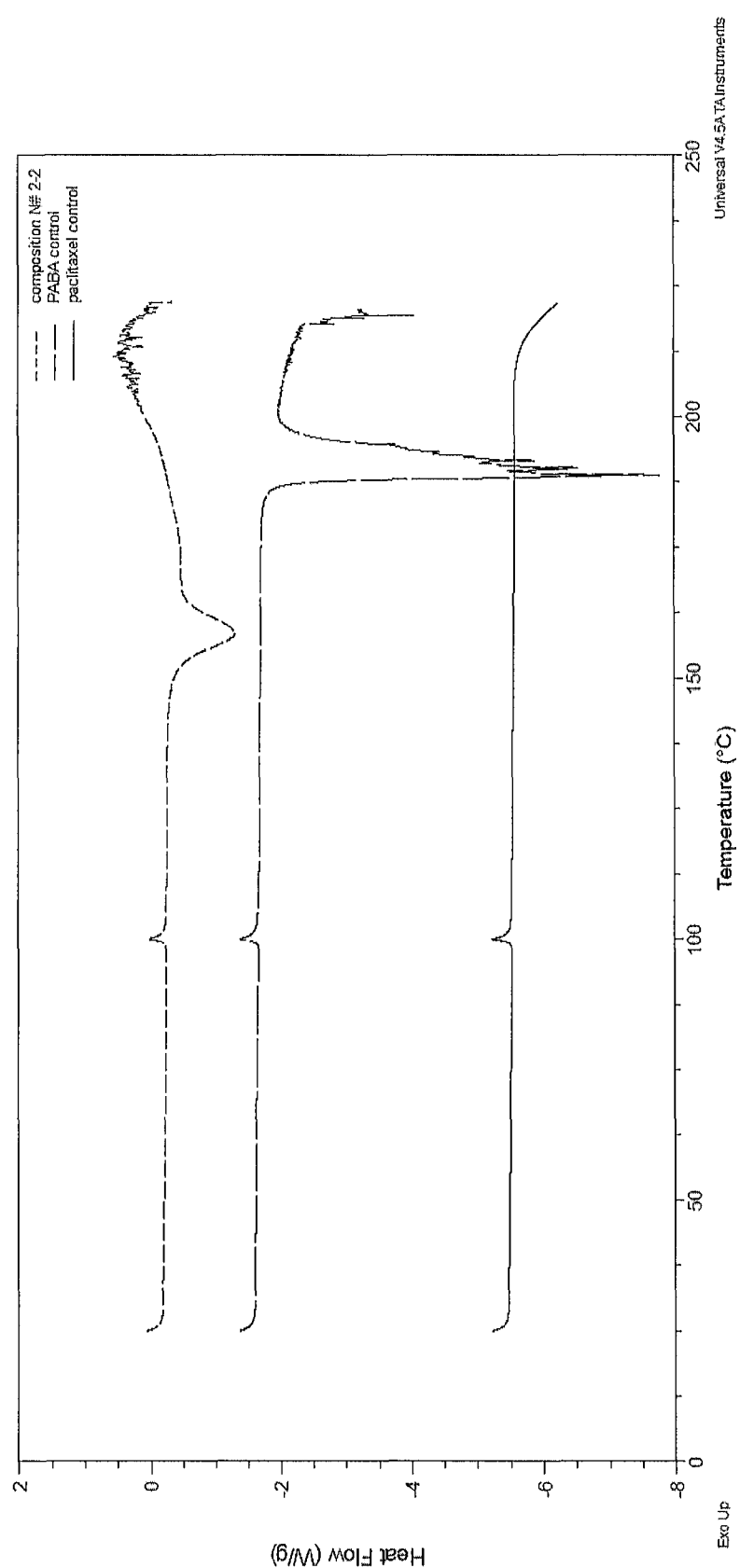
FIGS. 1A-C shows differential scanning calorimetry (DSC) thermograms of a paclitaxel-PABA composition (A), a paclitaxel-succinic acid composition (B), and a paclitaxel-adipic acid composition (C) respectively prepared according to Example 1.
Figure 1:
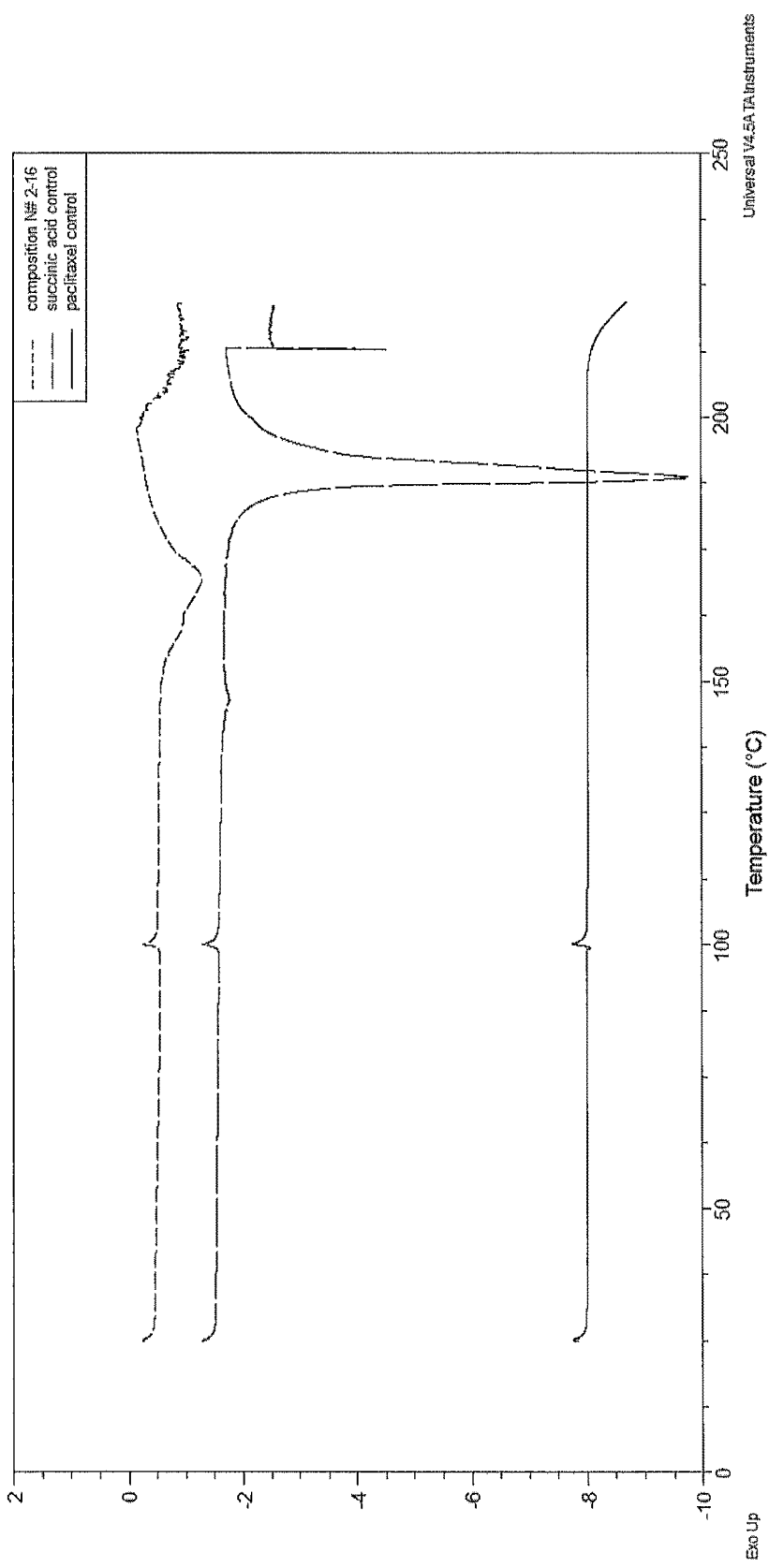

The present invention relates to novel paclitaxel-excipient solid compositions which exhibit a depressed melting endotherm. Such compositions are particularly useful for coating medical devices.

Medical Devices and Materials

The medical devices of the present invention are suitable for a wide range of applications including, for example, a range of medical treatment applications within the body. Exemplary applications include use as a catheter balloon for transferring drug to, or placement of, or "touch-up" of implanted vascular grafts, use as stents, stent-grafts, catheters, a permanent or temporary prosthesis, or other type of medical implant, treating a targeted tissue within the body, and treating any body cavity, space, or hollow organ passage(s) such as blood vessels, the urinary tract, the intestinal tract, nasal or sinus cavities, neural sheaths, intervertebral regions, bone cavities, the esophagus, intrauterine spaces, pancreatic and bile ducts, rectum, and those previously intervened body spaces that have implanted vascular grafts, stents, prosthesis, or other type of medical implants.

Additional examples of medical devices of the present invention include indwelling monitoring devices, artificial heart valves (leaflet, frame, and/or cuff), pacemaker or defibrillator electrodes, guidewires, cardiac leads, sutures, embolic filters, cardiopulmonary bypass circuits, cannulae, plugs, drug delivery devices, tissue patch devices, blood pumps, patches, osteoprostheses, chronic infusion lines, arterial lines, devices for continuous subarachnoid infusions, feeding tubes, CNS shunts (e.g., a ventriculopleural shunt, a ventriculo-atrial (VA) shunt, or a ventriculoperitoneal (VP) shunt), ventricular peritoneal shunts, ventricular atrial shunts, portosystemic shunts and shunts for ascites, devices for the filtering or removal of obstructions such as emboli and thrombi from blood vessels, as a dilation device to restore patency to an occluded body passage, as an occlusion device to selectively deliver a means to obstruct or fill a passage or space, and as a centering mechanism for transluminal instruments like catheters. In one embodiment, the medical devices of the present invention can be used to treat stent restenosis or treat tissue sites where previously placed drug eluting constructs have failed. In another embodiment, medical devices as described herein can be used to establish, connect to, or maintain arteriovenous access sites, e.g., those used during kidney dialysis.

Further examples of medical devices of the present invention which can be permanent or temporary are catheters. Examples of catheters include, but are not limited to, central venous catheters, peripheral intravenous catheters, haemodialysis catheters, catheters such as coated catheters include implantable venous catheters, tunneled venous catheters, coronary catheters useful for angiography, angioplasty, or ultrasound procedures in the heart or in peripheral veins and arteries, hepatic artery infusion catheters, CVC (central venous catheters), peripheral intravenous catheters, peripherally inserted central venous catheters (PIC lines), flow-directed balloon-tipped pulmonary artery catheters, total parenteral nutrition catheters, chronic dwelling catheters (e.g., chronic dwelling gastrointestinal catheters and chronic dwelling genitourinary catheters), peritoneal dialysis catheters, CPB catheters (cardiopulmonary bypass), urinary catheters and microcatheters (e.g. for intracranial application).

In one embodiment, the medical device is an expandable member which, according to the present invention, can be a balloon, expandable catheter, stent, stent-graft, a self-expanding construct, a balloon expandable construct, a combination self-expanding and balloon expandable construct, a graft or a mechanical, radially expanding device which may be expanded, for example, via application of a torsional or longitudinal force. Expandable members can also include those which expand due to pneumatic or hydraulic pressure, those which expand due to magnetic forces, those which expand due to the application of energy (for example thermal, electrical, or ultrasonic (piezoelectric) energy). Expandable members can be placed temporarily in any lumen (e.g. a vessel) by expanding said device and then removed by collapsing said device by a torsional or longitudinal force.

In one embodiment, the medical device is a stent such as a bifurcated stent, balloon expandable stent or a self-expanding stent. Stents are configured as braids, wound wire forms, laser-cut forms, deposited materials, 3-D printed constructs, or combinations thereof, or take other structural forms, including those with length-adjustability, which provide support to a luminal wall or region. Stents are constructed of biocompatible materials including metals, metal alloys, such as stainless steel and nickel-titanium alloy (NiTi), polymers, ceramics, biodegradable materials (such as biodegradable polymers, ceramics, metals and metal alloys), or combinations thereof. Stents can be of substantially unitary form or comprise separate components, e.g., rings. Whether unitary or made up of components, stent structures can be joined together by struts, hinges, connectors, or materials which fully or partially line or cover the stent. In one embodiment, the stent structure is joined with fluoropolymers forming "webs" as described in US2009/0182413 (Gore Enterprise Holdings, Inc., incorporated herein by reference).

In one embodiment, the medical device is a stent such a bifurcated stent, a balloon expandable stent or a self-expanding stent. In one embodiment, the medical device is a stent formed from a metal, a metal alloy, a polymer, a ceramic, a biodegradable material, or a combination thereof.

In one embodiment, the medical device is a stent-graft. Stent-grafts combine at least one stent member with a graft component. Grafts are typically configured as tubular members, with closed walls or walls with openings. Graft materials include biocompatible materials such as fluoropolymers, including polytetrafluoroethylene (PTFE) and expanded polytetrafluoroethylene (ePTFE). Other suitable graft materials include polymers such as polyethylene terephthalate and ultra-high molecular weight polyethylene (UHMWPE). Graft materials can be made to possess different strengths, densities, dimensions, porosities and other functional characteristics and can take the form of films, extrusions, electrospun materials, coatings, depositions, or molded articles. Grafts may used alone or graft materials can fully or partially line or cover a stent structure. In one embodiment, the stent-graft can take forms as described in U.S. Pat. No. 5,876,432 (Gore Enterprise Holdings, Inc., incorporated herein by reference).

In one embodiment, the medical device is a stent graft, wherein the graft is formed from a polymer, suitably a biocompatible polymer. Suitably the graft is formed from a fluoropolymer such as expanded polytetrafluoroethylene (ePTFE).

Stents, stent-grafts and grafts can be overlain with various materials such as polymers and primer layers. In an embodiment, the stent or graft structure is modified to enhance the ability of the device to hold or release a therapeutic agent applied to the device. For example, pits or blind holes can be formed in stent struts into which a therapeutic agent is loaded. When coated onto a stent, stent-graft, or graft, the composition of the invention will release a therapeutic agent in a localized manner, therefore a stent, stent-graft or graft coated with a composition of the invention is referred to herein as a drug eluting stent (DES).

In one embodiment, the expandable member is a medical balloon. Balloons useful in the invention may be formed by using any conventional manner such as extrusion, blow molding and other molding techniques. Balloons may be compliant or semi-compliant or non-compliant and may be of various lengths, diameters, sizes and shapes. Balloons can be so called "conformable" or "conforming", "length-adjustable" or "steerable" balloons, In other embodiments, the expandable members may comprise balloons which are constructed of wrapped films, are fiber-wound, are of variable length, are segmented, and/or have controlled or variable inflation profiles. In other embodiments, balloons may be overlain with a material or comprise more than one layer or be of composite construction. In an embodiment, the balloon surface or structure is modified to enhance the ability of the balloon to hold or release a therapeutic agent applied to it. For example, the balloon can be folded in such a way as to hold a therapeutic agent within said folds. When coated onto a balloon, the composition of the invention will release a therapeutic agent in a localized manner, therefore a balloon coated with a composition of the invention is referred to herein as a drug eluting balloon (DEB).

According to the present invention, medical balloons may be formed using any materials known to those of skill in the art. Commonly employed materials include the thermoplastic elastomeric and non-elastomeric polymers and the thermosets. Examples of suitable materials include but are not limited to, polyolefins, polyesters, polyurethanes, polyamides, polyether block amides, polyimides, polycarbonates, polyphenylene sulfides, polyphenylene oxides, polyethers, silicones, polycarbonates, styrenic polymers, fluoropolymers, copolymers thereof, and mixtures thereof. Some of these classes are available both as thermosets and as thermoplastic polymers. Useful polyamides include, but are not limited to, nylon 12, nylon 11, nylon 9, nylon 6/9 and nylon 6/6. Suitable fluoropolymers include polytetrafluoroethylene (PTFE) or expanded polytetrafluoroethylene (ePTFE). Examples of some copolymers of such materials include the polyether-block-amides, available from Elf Atochem North America in Philadelphia, Pa. under the tradename of PEBAX®. Another suitable copolymer is a polyetheresteramide. Suitable polyester copolymers, include, for example, polyethylene terephthalate and polybutylene terephthalate, polyester ethers and polyester elastomer copolymers such as those available from DuPont in Wilmington, Del. under the tradename of HYTREL®. Block copolymer elastomers such as those copolymers having styrene end blocks, and midblocks formed from butadiene, isoprene, ethylene/butylene, ethylene/propene, and so forth may be employed herein. Other styrenic block copolymers include acrylonitrile-styrene and acrylonitrile-butadiene-styrene block copolymers. Also, block copolymers wherein the particular block copolymer thermoplastic elastomers in which the block copolymer is made up of hard segments of a polyester or polyamide and soft segments of polyether may also be employed herein. Specific examples of polyester/polyether block copolymers are poly(butylene terephthalate)-block-poly(tetramethylene oxide) polymers such as ARNITEL® EM 740, available from DSM Engineering Plastics and HYTREL® polymers available from DuPont de Nemours & Co, already mentioned above.

In one embodiment, the medical device is a balloon formed from a polyolefin, polyester, polyurethane, polyamide, polyether block amide, polyimide, polycarbonate, polyphenylene sulfide, polyphenylene oxide, polyether, silicone, polycarbonate, styrenic polymer, fluoropolymers, a copolymer thereof, or a mixture thereof. Suitably the balloon is formed from a polyamide, such as nylon, or a fluoropolymer such as expanded polytetrafluoroethylene (ePTFE), polytetrafluoroethylene (PTFE), fluorinated ethylene-propylene (FEP), perfluorocarbon copolymers, e.g. tetrafluoroethylene perfluoroalkylvinyl ether (TFE/PAVE) copolymers, copolymers of tetrafluoroethylene (TFE) and perfluoromethyl vinyl ether (PMVE), copolymers of TFE with functional monomers that comprise acetate, alcohol, amine, amide, sulfonate, functional groups and the like as described in U.S. Pat. No. 8,658,707 (W. L. Gore and Associates, incorporated herein by reference), as well as combinations thereof.

In one embodiment, the medical devices of the invention comprise a medical balloon used for Percutaneous Transluminal Angioplasty (PTA) in patients with obstructive disease of the peripheral arteries. In another embodiment, said medical device comprises a medical balloon used for Percutaneous Transluminal Coronary Angioplasty (PTCA). In another embodiment, medical devices provided by the present invention can be used to treat coronary stenosis or obstructions.

In one embodiment, the expandable member is covered with a porous material onto which a coating layer of the present invention is applied. In an embodiment, the expandable member covering material is a fluoropolymer such as polytetrafluoroethylene (PTFE) or an expanded PTFE (ePTFE). The structure of expanded PTFE characterized by nodes interconnected by fibrils, is taught in U.S. Pat. Nos. 3,953,566 and 4,187,390 (W. L. Gore & Associates; both incorporated herein by reference). In one embodiment, the fluoropolymer expandable member covering comprises ePTFE having a material structure with fibrils or fibrils and nodes. In another embodiment, the fibrils or fibrils and nodes change in size, dimension, or orientation as a dimension of the expandable member covering is changed. In one embodiment, the expandable member is a balloon, disposed over at least a part of which is a covering, the covering being made at least in part of ePTFE, and disposed over at least a portion of the ePTFE balloon covering is a coating of the present invention.

In one embodiment, the expandable member comprises a covering disposed around at least a portion of a coating layer of the invention. Such a covering may also be described as a sheath. In one embodiment the covering is removable from over the coating layer. In one embodiment, the covering is disposed over a coating layer of the invention applied to an expandable member. The covering can comprise any biocompatible material, including any possessing porosity or permeability. In one embodiment, the porosity or permeability varies as the material is deformed or otherwise altered in dimension.

Materials which may exhibit porosities or permeabilities that change with changes in the dimension of covering include, but are not limited to, fibrillated structures, such as expanded fluoropolymers (for example, expanded polytetrafluoroethylene (ePTFE)) or expanded polyethylene (as described in U.S. Pat. No. 6,743,388 (Sridharan et al.) and incorporated herein by reference); fibrous structures (such as woven or braided fabrics; non-woven mats of fibers, microfibers, or nanofibers; materials made from processes such as electrospinning or flash spinning; polymer materials consisting of melt or solution processable materials such as fluoropolymers, polyamides, polyurethanes, polyolefins, polyesters, polyglycolic acid (PGA), polylactic acid (PLA), and trimethylene carbonate (TMC), and the like; films with openings created during processing (such as laser- or mechanically-drilled holes); open cell foams; microporous membranes made from materials such as fluoropolymers, polyamides, polyurethanes, polyolefins, polyesters, PGA, PLA, TMC, and the like; porous polyglycolide-co-trimethylene carbonate (PGA:TMC) materials (as described in U.S. Pat. No. 8,048,503 (Gore Enterprise Holdings, Inc.)) and incorporated herein by reference); or combinations of the above. Processing of the above materials may be used to modulate, enhance or control porosity or permeability between a first, closed state and second, more porous or permeable state. Such processing may help close the material structure (thus lowering porosity or permeability) in a first state, help open the material structure in a second state, or a combination of both. Such processing which may help close the material structure may include, but is not limited to: calendaring, coating (discontinuously or continuously), compaction, densification, coalescing, thermal cycling, or retraction and the like. Such processing that may help open the material structure may include, but is not limited to: expansion, perforation, slitting, patterned densification and/or coating, and the like. In another embodiment, said materials comprise pores between fibrils or between nodes interconnected by fibrils, such as in ePTFE.

One skilled in the art will appreciate various methods which characterize the change in porosity or permeability using testing at a first state comparing to testing done at a second state. These methods include, but are not limited to, characterizations of air or liquid flux across the material structure at a given pressure differential, characterization which determines the pressure differential at which different fluids strike through the material structure such as Water Entry Pressure or Bubble Point, and visual characterization as measured from an image (e.g. from a scanning electron microscope or light microscope).

In one embodiment, the covering material is a fluoropolymer such as expanded polytetrafluoroethylene (ePTFE), polytetrafluoroethylene (PTFE), fluorinated ethylene-propylene (FEP), perfluorocarbon copolymers, e.g. tetrafluoroethylene perfluoroalkylvinyl ether (TFE/PAVE) copolymers, copolymers of tetrafluoroethylene (TFE) and perfluoromethyl vinyl ether (PMVE), copolymers of TFE with functional monomers that comprise acetate, alcohol, amine, amide, sulfonate, functional groups and the like as described in U.S. Pat. No. 8,658,707 (W. L. Gore and Associates, incorporated herein by reference), as well as combinations thereof. In another embodiment, the fluoropolymer covering possesses a material structure which changes as a dimension of the covering changes. In one embodiment, the fluoropolymer covering comprises ePTFE having a material structure with fibrils or fibrils and nodes. In another embodiment, the fibrils or fibrils and nodes change in size, dimension, or orientation as a dimension of the covering is changed. In one embodiment, the expandable member is a balloon, disposed over at least a part of which is a covering, the covering being made at least in part of ePTFE, and the material structure of the ePTFE changes upon expansion of the balloon.

In another embodiment, the expandable member is a balloon, disposed over at least a part of which is a coating layer of the invention which in turn is covered at least in part with a covering such as a sheath, the covering being made at least in part of ePTFE, and the material structure of the ePTFE changes upon expansion of the balloon. In one embodiment, the porosity or permeability of the covering is sufficiently low so as to prevent substantial movement of material in the coating layer from moving through the covering. In another embodiment, the porosity or permeability of the covering increases upon expansion of the balloon and allows at least some of the material in the coating layer to detach from the surface of the balloon. In one embodiment, the material detached is a paclitaxel-excipient solid composition of the invention. Once the paclitaxel-excipient solid composition passes through the outer covering, it is delivered to a treatment site.

In one embodiment the covering is essentially hydrophobic and is treated to render it hydrophilic using, for example, the methods described in US2013/0253426 (W. L. Gore & Associates; incorporated herein by reference). In another embodiment, the covering comprises a film or film tube of ePTFE.

In another embodiment of the invention, the surface(s) or outward configuration of the covering material may be modified with textures, protrusions, wires, blades, spikes, scorers, depressions, grooves, coatings, particles, and the like. In another embodiment of the invention, the surface(s) or outward configuration of the covering material may be modified with needles, cannulae, and the like. These modifications may serve various purposes such as to modify tissues into which therapeutic agents will be (or have been) delivered, control placement of the system of the invention, and direct fluid transfer. Such textures may help in increased transfer of a therapeutic agent onto, more deeply and/or into deeper tissues. Such textures may be comprised of the covering material, or may be comprised of an added material.

In another embodiment of the invention, the location(s) of the permeable microstructure may be varied. For example, a covering may be constructed such that only a portion of its microstructure is variably permeable. Such a configuration may be desirable where fluid transfer is not desired to occur, for example, at one or both of the ends of the expandable medical device of the invention. This may be desirable where multiple drug eluting devices will be used in a specific anatomy, and it would be undesirable to overlap treatments sites, i.e., delivering too much drug to a particular site.

In another embodiment, the covering may contain or be marked with radiopaque markers or be constructed to be radiopaque in its entirety. Such radiopaque indicators are used by clinicians to properly track and place an expandable medical device of the invention.

In one embodiment, the medical device is an expandable member. In another embodiment, the medical device is a balloon, a stent, a stent-graft or a graft.

The solid composition of the invention can be applied to the entire surface of the device, or only a portion of the surface of the device. Certain devices may have an external surface and an internal surface, either or both of which can be coated. For example, tubular substrates including but not limited to artificial blood vessels, vascular grafts, stents, and stent grafts, have an internal surface, or lumen, which can be coated independently from the external surface. A device comprising an internal and an external surface may only require the external surface to be coated. Conversely, only the internal surface may require a coating of the invention. In one embodiment, the amount or thickness of the coating may be varied over the surface of the medical device. The coating layer can be continuous over an entire surface of the device or be discontinuous and cover only a portion or separate portions of the device. The coating layer can also be "sculpted" or modified to create a desired surface topography or modified with textures, as described supra.

In one embodiment, up to 99%, for example up to 95%, 90%, 75%, 50% or 25% of the surface of the device is coated with the coating of the invention. In one embodiment, both the external and internal surfaces of the device are coated. In another embodiment, only the external surface of the device is coated.

The medical device, in particular a surface of the medical device, can be composed of one or more materials as described hereinabove. The medical device may comprise, consist, consist essentially of, or be formed of a metal or a synthetic or naturally occurring organic or inorganic polymer or a ceramic material, inter alia.

Thus, for example, the medical device, in particular a surface of the medical device, is composed of a synthetic or naturally occurring organic or inorganic polymer or material, including but not limited to materials such as polyolefins, polyesters, polyurethanes, polyamides, polyether block amides, polyimides, polycarbonates, polyphenylene sulfides, polyphenylene oxides, polyethers, silicones, polycarbonates, polyhydroxyethylmethacrylate, polyvinyl pyrrolidone, polyvinyl alcohol, rubber, silicone rubber, polyhydroxyacids, polyallylamine, polyallylalcohol, polyacrylamide, and polyacrylic acid, styrenic polymers, polytetrafluoroethylene and copolymers thereof, expanded polytetrafluoroethylene and copolymers thereof, derivatives thereof and mixtures thereof. Some of these classes are available both as thermosets and as thermoplastic polymers. As used herein, the term "copolymer" shall be used to refer to any polymer formed from two or more monomers, e.g. 2, 3, 4, 5 and so on and so forth. Bioresorbables, such as poly(D,L-lactide) and polyglycolids and copolymers thereof are also useful. Non-woven, bioabsorbable web materials comprising a tri-block copolymer such as poly(glycolide-co-trimethylene carbonate) tri-block copolymer (PGA: TMC) are also useful (as described in U.S. Pat. No. 7,659,219; Biran et al.). Useful polyamides include, but are not limited to, nylon 12, nylon 11, nylon 9, nylon 6/9 and nylon 6/6. Examples of some copolymers of such materials include the polyether-block-amides, available from Elf Atochem North America in Philadelphia, Pa. under the tradename of PEBAX®. Another suitable copolymer is a polyetheresteramide. Suitable polyester copolymers, include, for example, polyethylene terephthalate and polybutylene terephthalate, polyester ethers and polyester elastomer copolymers such as those available from DuPont in Wilmington, Del. under the tradename of HYTREL®. Block copolymer elastomers such as those copolymers having styrene end blocks, and midblocks formed from butadiene, isoprene, ethylene/butylene, ethylene/propene, and so forth may be employed herein. Other styrenic block copolymers include acrylonitrile-styrene and acrylonitrile-butadiene-styrene block copolymers. Also, block copolymers wherein the particular block copolymer thermoplastic elastomers in which the block copolymer is made up of hard segments of a polyester or polyamide and soft segments of polyether may also be employed herein. Other useful materials are polystyrenes, poly(meth-yl)methacrylates, polyacrylonitriles, poly(vinylacetates), poly(vinyl alcohols), chlorine-containing polymers such as poly(vinyl) chloride, polyoxymethylenes, polycarbonates, polyamides, polyimides, polyurethanes, phenolics, amino-epoxy resins, polyesters, silicones, cellulose-based plastics, and rubber-like plastics. Combinations of these materials can be employed with and without cross-linking. Polymeric materials may optionally be blended with fillers and/or colorants, such as a gold, barium, or tantalum filler to render the polymeric material radiopaque. Polymeric materials may optionally be modified at their surface while retaining bulk properties using methods known in the art, such as acid or base etching, hydrolysis, aminolysis, plasma modification, plasma grafting, corona discharge modification, chemical vapour deposition, ion implantation, ion sputtering, ozonation, photomodification, electron beam modification, gamma beam modification, and the like. Suitably a surface of the medical device is composed of nylon.

In one embodiment, the medical device, in particular a surface of the medical device is biocompatible and comprises or consists of a polyether-block-amides, such as PEBAX®.

The medical device, in particular a surface of the medical device, may be composed of fluorinated polymers such as fluoropolymers, e.g. expanded polytetrafluoroethylene (ePTFE), polytetrafluoroethylene (PTFE), fluorinated ethylene-propylene (FEP), perfluorocarbon copolymers, e.g. tetrafluoroethylene perfluoroalkylvinyl ether (TFE/PAVE) copolymers, copolymers of tetrafluoroethylene (TFE) and perfluoromethyl vinyl ether (PMVE), copolymers of TFE with functional monomers that comprise acetate, alcohol, amine, amide, sulfonate, functional groups and the like as described in U.S. Pat. No. 8,658,707 (W. L. Gore and Associates, incorporated herein by reference, as well as combinations thereof. Also contemplated are combinations of the above with and without crosslinking between the polymer chains, expanded polyethylene, polyvinylchloride, polyurethane, silicone, polyethylene, polypropylene, polyurethane, polyglycolic acid, polyesters, polyamides, elastomers and their mixtures, blends and copolymers or derivatives thereof. ePTFE has a porous microstructure which is particularly compatible with the coating of the invention. Suitably a surface of the medical device is composed of ePTFE.

The medical device, in particular a surface of the medical device, may also be composed of metals, including, but are not limited to, biocompatible metals, titanium, stainless steel, high nitrogen stainless steel, gold, silver, rhodium, zinc, platinum, rubidium, copper and magnesium, and combinations thereof. Suitable alloys include cobalt alloys including cobalt-chromium alloys such as L-605, MP35N, Elgiloy, titanium alloys including nickel-titanium alloys (such as Nitinol), tantalum, and niobium alloys, such as Nb-1% Zr, and others. In one embodiment, the medical device is a stent and is composed of biocompatible metal selected from stainless steel, tantalum, titanium alloys and cobalt alloys. The medical device, in particular a surface of the medical device may also be composed of a ceramic substrate including, but are not limited to, silicone oxides, aluminum oxides, alumina, silica, hydroxyapatites, glasses, calcium oxides, polysilanols, and phosphorous oxide.

In one embodiment of the invention, the coating layer is applied to a surface of a device which is composed of nylon. In another embodiment, the coating layer is applied to a surface of a device which is composed of ePTFE. In either embodiment, a proportion or the entire surface of the medical device is composed of nylon or ePTFE, respectively. In a further embodiment, the coating layer is applied to a surface of a balloon which is composed of nylon. In a still further embodiment, the coating layer is applied to a surface of a balloon which is composed of ePTFE. In a still further embodiment, the coating layer is applied to a surface of a balloon which is composed of copolymers of TFE with functional monomers that comprise acetate, alcohol, amine, amide or sulfonate functional groups and the like.

Coating Layer

The paclitaxel-excipient solid compositions of the invention are of use in coating medical devices. In the context of being used as a coating in a layer on a medical device, the paclitaxel-excipient solid compositions are therefore referred to herein as being "coatings of the invention" or "the coating layers of the invention".

The paclitaxel-excipient solid composition comprises a therapeutic agent which is paclitaxel and at least one excipient which is a non-polymeric organic additive.

Paclitaxel is sold commercially in formulations for the treatment of various cancers and for the prevention and treatment of restenosis. Paclitaxel is known to exist in several different physical forms, including amorphous, glassy and crystalline forms, wherein the crystalline forms can be further differentiated into a number of different polymorphs. Furthermore, crystalline paclitaxel can exist as an anhydrate or in hydrated form. The accepted melting point of crystalline paclitaxel is circa 220° C., depending on the heating conditions and polymorph form (Liggins et al. "Solid-state characterization of paclitaxel", J. Pharm. Sci. 1997, Vol. 86, pages 1458-1463). It is known that the particular form of paclitaxel can affect the physical properties of the drug when in solid form. In particular, the adherence of paclitaxel to a surface may be influenced by its physical form, as can its rate of dissolution from a surface to the surroundings. Thus, formulating paclitaxel for solid delivery can be challenging at the first instance, and the effect of formulating paclitaxel in solid form with an excipient cannot easily be predicted.

The coating of the invention also comprises at least one excipient which is a non-polymeric organic additive. The term "non-polymeric" will be clear to a person of skill in the art as meaning a substance which does not contain multiple repeating monomer units. Typically, a polymer will consist of at least 5 repeating monomer units, for example at least 6, at least 7, at least 8 or at least 9 repeating monomer units. References to polymers are intended to include copolymers. Examples of polymeric substances include proteins which are thus not suitable as organic additives for use in the invention. Poly(lactic-co-glycolic) acid (PLGA), polyvinylpyrrolidone (PVP) and polyethylene glycol (PEG) and poloxamers are examples of polymers which are not suitable as an organic additive for use in the invention. Thus, coatings and compositions of the invention do not contain polymers, in particular polylactic-co-glycolic) acid (PLGA), polyvinylpyrrolidone (PVP) or polyethylene glycol (PEG). A further example of a material which is polymeric and therefore not suitable as an organic additive for use in the coating and composition of the invention is shellac.

In one embodiment, the coating layer is plasticizer-free i.e. does not contain a plasticizer. Plasticizers (also known as dispersants) are defined herein as compounds that increase the plasticity or fluidity of a material, usually a polymer. Plasticizers can be in monomeric, oligomeric or polymeric form. Examples of plasticizers include acetic acid, formic acid, 1-butanol, 2-butanol, ethanol, 2-methyl-1-butanol, 2-methyl-1-propanol, 1-pentanol, 1-propanol, 2-propanol, ethyl acetate, ethyl formate, isopropyl acetate, methyl acetate, propyl acetate, anisole, tert-butylmethyl ether, ethyl ether, cumene, heptane, pentane, acetone, methylethyl ketone, methylisobutyl ketone, dimethyl sulfoxide, glycerin, polyethylene glycols, polyethylene glycol monomethyl ether, sorbitol, sorbitan, citrate esters including acetyl tributyl citrate, acetyl triethyl citrate, tributyl citrate, triethyl citrate and the like, castor oil, diacetylated monoglycerides, dibutyl sebacate, diethyl phthalate, triacetin, fractionated coconut oil, and acetylated monoglycerides.

The organic additive is hydrolytically stable i.e. resistant to chemical reaction/decomposition in the presence of water. A compound which is not hydrolytically stable will undergo an irreversible chemical transformation in an aqueous solution e.g. ester or amide or anhydride hydrolysis. Conversely, a compound which is hydrolytically stable will not undergo an irreversible transformation in an aqueous solution. A compound may undergo reversible proton exchange, or reversible hydrate formation and still be considered as being hydrolytically stable. When a compound is exposed to an aqueous solution and a chemical transformation results, and if the resulting compound (degradant) cannot be converted back to the original compound by simple pH modification, then the original compound is not hydrolytically stable.

In one embodiment, a compound is hydrolytically stable if, when exposed to buffered saline at pH 7.4, for 1 to 24 h (for example 5 h, 10 h, 15 h or 24 h), it does not show chemical reaction or degradation when analyzed with ultra-performance liquid chromatography (UPLC) or high-performance liquid chromatography (using a method similar to that set out in "Evaluation methods"). In one embodiment, a compound is considered to be hydrolytically stable if, following the treatment above, at least 80%, for example at least 90% of 95% of the compound is recovered in un-degraded form.

Whether a particular compound is hydrolytically stable or not can depend on the pH. In one embodiment, the organic additive is hydrolytically stable at physiological pH. In one embodiment, physiological pH is pH 7.4.

Certain chemical functional groups such as esters, in particular succinimidyl esters, sulfosuccinimidyl esters, acyl halides, acetals, hemiacetals, and anhydrides are known to be prone to hydrolysis therefore compounds containing such functionality might, at the first instance, appear not be suitable as an organic additive in the coating of the invention. However, the hydrolytic stability of such functional groups can be enhanced by the remaining functionality of the compound e.g. by steric or electronic effects of neighbouring functional groups. Thus, although the presence of functional groups known to be prone to hydrolysis may, on a first assessment, indicate that a compound is unsuitable for the purposes of being the organic additive, the compound as a whole should be assessed. The following substances at least are not suitable as organic additives for use in the present invention because they are not hydrolytically stable: gluconolactone, maleic anhydride, diglycolic anhydride and acetic anhydride.

Early experiments indicated that vanillin was unsuitable for use as the organic additive as it easily degraded in solution. Thus, vanillin is not suitable as an organic additive for the present invention. In one embodiment, the coating layer does not contain vanillin. In one embodiment, the organic additive does not contain phenolic aldehyde functionality. In another embodiment, the coating of the invention does not contain compounds containing phenolic aldehyde functionality.

The use of Hansen solubility parameters can assist in the understanding or rationalization of the behaviour of a composition comprising two or more components (Mohammed et al. International Journal of Pharmaceutics 2011, Vol. 407 pp 63-71 and Albers et al. Journal of Pharmaceutical Sciences 2011, Vol. 100 pp 667-680). In one embodiment, the organic additive is a substance having a value for the dispersion component of the Hansen solubility parameter determined at 25° C. substantially the same as that of paclitaxel. In one embodiment, "substantially the same" means within ±3.0 MPa$^{0.5}$ of the value for the dispersion component of the Hansen solubility parameter for paclitaxel (determined at 25° C.). Suitably the dispersion component of the Hansen solubility parameter determined at 25° C. of the organic additive is between 16 and 21 MPa$^{0.5}$.

The organic additive will typically have a low molecular weight. For example, the organic additive will have a molecular weight of less than 1200 Da, less than 990 Da, less than 750 Da, less than 500 Da, less than 400 Da or less than 300 Da. In one embodiment, the organic additive has a molecular weight of between about 50 Da and about 400 Da, for example between about 80 Da and about 350 Da. The organic additive is not a protein. In one embodiment, the coating layer is free of protein. In a further embodiment, the organic additive is not a therapeutic agent. In an embodiment the organic additive is not aspirin.

The organic additive will typically have a melting point of greater than 80° C. when in pure form, for example greater than 90° C., greater than 100° C., greater than 110° C. or greater than 120° C. Compounds with a melting point lower than 80° C. when in pure form generally have weak intermolecular interactions, potentially leading to the compound being physically unstable. Compounds that are capable of forming coordinated solvates, such as a hydrate, with the paclitaxel and/or the organic additive typically have physical stability.

In one embodiment the (at least one) organic additive is independently selected from the list consisting of p-aminobenzoic acid, saccharin, ascorbic acid, methyl paraben, caffeine, calcium salicylate, pentetic acid, creatinine, ethylurea, acetaminophen, aspirin, theobromine, tryptophan, succinic acid, glutaric acid, adipic acid, theophylline, and saccharin sodium. The formation of compositions and coatings of the invention using these organic additives is described in Examples 1 and 3. Suitably the (at least one) organic additive is independently selected from the list consisting of p-aminobenzoic acid, methyl paraben, caffeine, calcium salicylate and succinic acid. In one embodiment the organic additive is succinic acid. In another embodiment, the organic additive is caffeine.

In an embodiment the organic additive is not sodium salicylate. In an embodiment the organic additive is not calcium salicylate. In an embodiment the organic additive is not magnesium salicylate.

In an embodiment the organic additive is not a substance containing magnesium ions i.e. a magnesium salt.

In an embodiment the organic additive is not ascorbic acid or a salt thereof e.g. L-ascorbic acid or a salt thereof.

The therapeutic agent, when formulated in the coating layer, should be able to withstand a sterilization process essentially intact. A therapeutic agent within the coating layer is defined as being essentially intact after sterilization, or is considered to be stable to sterilization, if it exhibits no more than 20% degradation after sterilization without aging, for example no more than 15%, 10%, 9%, 8%, 7%, 6%, 5%, 4%, 3%, 2% or 1% degradation. The therapeutic agent is considered to be degraded if it is chemically altered following sterilization. Conversely, a therapeutic agent in the coating layer is defined as being essentially intact after sterilization, or is considered to be stable to sterilization, if the coating retains at least 80% of the therapeutic agent chemical content after sterilization, for example at least 85%, 90%, 91%, 92%, 93%, 94%, 95%, 96%, 97%, 98%, 99% or substantially all of the therapeutic agent chemical content after sterilization.

The amount of intact therapeutic agent in the coating following sterilization can be determined using high-performance liquid chromatography (HPLC) techniques such as ultra-performance liquid chromatography (UPLC), for example using the UPLC method described in the Evaluation methods section, and/or by mass spectrometry.

Suitable sterilization processes include, but are not limited to sterilization using ethylene oxide, vapour hydrogen peroxide, plasma phase hydrogen peroxide, dry heat, autoclave steam sterilization, chlorine dioxide sterilization, gamma ray sterilization or electron beam sterilization. In one embodiment, the therapeutic agent is essentially intact after ethylene oxide sterilization, vapour hydrogen peroxide sterilization, plasma phase hydrogen peroxide sterilization or electron beam sterilization. In one embodiment, the therapeutic agent stable to ethylene oxide sterilization, vapour hydrogen peroxide sterilization, plasma phase hydrogen peroxide sterilization or electron beam sterilization (or indeed multiple sterilization methods). Sterilization using ethylene oxide is the most commonly utilized, proven and readily available sterilization technique for implantable medical devices such as stents, stent grafts, balloons and balloon catheters. Thus, in one embodiment, the therapeutic agent is essentially intact after sterilization using ethylene oxide. In another embodiment, the therapeutic agent is stable to ethylene oxide sterilization.

Specific evaluation methods "Test Method D", "Test Method E", "Test Method F", and "Test Method G" are provided in the Test Methods section for assessing stability to sterilization using ethylene oxide, electron beam, vapour hydrogen peroxide, and plasma hydrogen peroxide, respectively.

In one aspect of the invention is provided a coated medical device as described herein which has been sterilized, e.g. ethylene oxide sterilized.

In Example 12a, balloons coated with a paclitaxel-caffeine coating and a paclitaxel-succinic acid coating (prepared according to Example 3b) were testing using Test method D and were found to retain >80% of their paclitaxel chemical content following ethylene oxide sterilization.

In Example 12b, various paclitaxel-organic additive compositions were tested using Test method D and were found to retain between 88.5% and 100% of their paclitaxel chemical content following ethylene oxide sterilization.

Compounds with certain functional groups such as primary amides (—C(O)NH$_2$) and primary alkyl amines (alkyl-NH$_2$) have been observed to be incompatible with paclitaxel, when formulated together as a solid coating and subjected to ethylene oxide sterilisation. An example of such a compound is niacinamide, which (as described in Example 12c), when formulated with paclitaxel and coated onto a balloon, resulted in nearly complete paclitaxel degradation when the balloon was ethylene oxide sterilised. Thus, compounds containing such functionality might cause paclitaxel to degrade under ethylene oxide sterilization, therefore might not be suitable as an organic additive in the coating of the invention. However, the interaction of such compounds with paclitaxel may be altered by the remaining functionality of the molecule, for example, the reactivity of primary amide or primary alkyl amine groups adjacent to aromatic functionality can be tempered to the extent that such compounds will not cause degradation of paclitaxel under ethylene oxide sterilization conditions. The following substances at least are not suitable as organic additives for use in the present invention because they cause degradation of the paclitaxel under the conditions of ethylene oxide sterilization: niacinamide and sodium salicylate.

Thus, the organic additive is not niacinamide (also known as nicotinamide) or sodium salicylate. In one embodiment, the coating layer does not contain niacinamide.

As discussed in further detail below, coatings of the invention can be prepared by pipetting a solution containing therapeutic agent and excipient onto the device to be coated. Using this method it is difficult to achieve a suitable coating unless both components are soluble in the solution. The present inventors found it was not possible to form coatings where the organic additive has poor solubility in the solvent system. For example, thiamine-HCl has poor solubility in acetone, ethanol and aqueous mixtures thereof and attempts to formulate a paclitaxel-thiamine-HCl coating on a balloon were unsuccessful. Thus, in one embodiment the organic additive is not thiamine-HCl. In another embodiment, the coating layer does not contain thiamine-HCl.

Suitably the organic additive is not dexpanthenol. Suitably the organic additive is not ricinoleic acid. Suitably the organic additive is not resorcin. Suitably the organic additive is not isomalt.

The coating layer is surfactant-free i.e. does not contain a surfactant. Surfactants are defined herein as compounds that are amphiphilic and contain both hydrophobic and hydrophilic groups and include ionic, non-ionic, zwitterionic, aliphatic and aromatic surfactants. Surfactants can be in monomeric, oligomeric or polymeric form. Examples of surfactants include, but are not limited to, polysorbate (Tween® 20, Tween® 40, Tween® 60), PEG-fatty esters, PEG mega-3 fatty esters, PEG ethers (such as Triton X-100/octoxynol-9) and alcohols (such as tyloxapol), glycerol fatty esters, sorbitan fatty esters, PEG, glyceryl fatty esters, PEG sorbitan fatty esters, PEG sugar esters, poloxamers (which may be sold under the trade names of Synperonics®, Pluronics® and Kolliphor®), ascorbyl palmitate and p-isononylphenoxypolyglycidol (Olin 10-G® or Surfactant 10-G®).

In one embodiment, the coating of the invention is free of cyclodextrin.

In one embodiment, the coating of the invention is free of inorganic components (e.g. salts having both inorganic cations and inorganic anions). Suitably the coating of the invention is bioabsorbable or is biostable.

In one embodiment, the coating layer consists of the therapeutic agent and at least one organic additive. In this embodiment, the coating layer does not comprise components other than paclitaxel or at least one organic additives as described herein.

In one embodiment, the coating layer comprises one organic additive. In one embodiment, the coating layer consists of the therapeutic agent which is paclitaxel and one organic additive as described herein. In this embodiment, the coating of the invention is a binary composition (See Examples 1 and 3 for examples of binary compositions and coatings of the invention). In one, embodiment the organic additive is succinic acid. In another embodiment, the organic additive is caffeine.

In one embodiment, the coating layer comprises two organic additives. In one embodiment, the coating layer consists of the therapeutic agent which is paclitaxel and two organic additives as described herein. In this embodiment, the coating of the invention is a ternary composition (see Example 14 for an example of a ternary composition of the invention). In one embodiment, the two organic additives are caffeine and succinic acid. In one embodiment, the coating layer comprises three or more organic additives.

In another embodiment, the coating of the invention is not a ternary composition i.e. the coating consists of more or fewer than three components. In another embodiment, the coating of the invention is not a quaternary composition i.e. the coating consists of more or fewer than four components.

Coatings of the invention are described as particulate because when visually examined macroscopically, they appear opaque/white and not glassy (i.e., transparent). Furthermore, when the coating surface is analyzed using microscopy techniques such as scanning electron microscopy (SEM) at a suitable magnification e.g. 5000×, an abundance of individual particles of roughly 1 µm length can be observed.

A key characteristic of the coating of the invention comprising paclitaxel and at least one organic additive is that at least a proportion of the coating exhibits a depressed melting endotherm. A melting endotherm is observed in a differential scanning calorimetry (DSC) measurement. Thus, "melting point" and "peak melting endotherm" as referred to herein should be considered as being equivalent. A "depressed melting endotherm" is observed when a proportion of the coating comprising paclitaxel and at least one organic additive melts as a single phase at a lower temperature than the melting point of either paclitaxel or the at least one organic additive when in pure form. If the coating layer or composition contains more than one organic additive, the depressed melting endotherm is lower than the melting points of all of the organic additives present in the coating layer.

Reference to "at least a proportion" of the coating exhibiting a depressed melting point is intended to cover the scenario when the entire coating comprising paclitaxel and at least one organic additive exhibits a depressed melting point i.e. the remaining coating (other than the defined "proportion") can also exhibit the same depressed melting point.

The proportion of the coating layer comprising paclitaxel and the at least one organic additive which exhibits a depressed melting point melts at the lower temperature as a single phase i.e. a single depressed melting point is observed at which point both the paclitaxel and the at least one organic additive melt simultaneously.

In at least some embodiments it has been observed that the coatings of the invention comprising paclitaxel and the at least one organic additive are predominantly in crystalline form.

The coating layer may comprise crystalline particles of paclitaxel and the at least one organic additive in the form of a eutectic mixture, wherein the eutectic mixture exhibits a depressed melting point. A eutectic mixture is defined herein as an intimately blended physical mixture of two or more crystalline components which melts as a single phase having a melting point lower than that of either or any of its components. A eutectic mixture tends to form when the two (or more) different crystalline components are mismatched in terms of molecular size or molecular shape such that cohesive interactions are relatively stronger than adhesive interactions, leading to a conglomerate of the two or more lattice structures, rather than a new lattice structure. Therefore, an X-ray powder diffraction ("XRPD") pattern of such a paclitaxel-organic additive coating would be expected to have an XRPD pattern identical to, or substantially similar to, a superimposition of the individual XRPD patterns of paclitaxel and the organic additive. The XRPD pattern of such a coating would not have a unique lattice arrangement distinct from the individual components therefore peaks other than those corresponding to the paclitaxel and organic additive would not be visible (Cherukuvada et al., 2014, Chem. Comm, Vol. 50, pages 906-923). Without wishing to be bound by theory, the inventors believe that the colligative properties and high thermodynamic functions (e.g. free energy, enthalpy and entropy) of a eutectic drug coating composition could allow rapid transfer of the drug from the coating to an adjacent tissue, while minimizing the nonspecific loss of drug from the coating prior to transfer to the adjacent tissue.

Alternatively, the coating layer may comprise particles of crystalline material comprising paclitaxel and the at least one organic additive, sometimes referred to as a "co-crystal", wherein the crystalline material exhibits a depressed melting point. A co-crystal rather than a eutectic system is more likely to be formed when the two (or more) individual components have a strong adhesive interaction leading to an essentially single continuous crystalline phase. A co-crystalline paclitaxel-organic additive coating material would therefore be expected to exhibit a unique XRPD pattern, different from that of the paclitaxel or organic additive (Cherukuvada et al., 2014, Chem. Comm, Vol. 50, pages 906-923).

It is widely accepted that there are no ground rules or structural guidelines as to the point at which the cohesive interactions dominate over the adhesive interactions (to give a eutectic) and vice versa (to give a co-crystal). It should be noted that the exact structural nature of the coating and composition of the invention (i.e. eutectic, co-crystal or mixture thereof) need not be determined for the purposes of working the present invention, as the key feature that all of the embodiments above share is that of having a depressed melting point.

As mentioned above, paclitaxel can have an optional amount of coordinated solvent, e.g. can be present in the composition in the form of a solvate, such as a hydrate. In one embodiment, the paclitaxel is present in the coating and composition as anhydrous paclitaxel. In another embodiment, the paclitaxel is present in the coating and composition in the form of a paclitaxel hydrate. In an alternative embodiment, both anhydrous and hydrated forms of paclitaxel may be present in the coating and composition of the invention.

The relative amounts of paclitaxel and at least one organic additive in the coating of the invention should be such that at least a proportion of the coating will exhibit a depressed melting point. This will depend to some extent on the nature of the at least one organic additives, but can easily be determined by varying the ratio of the two components and analysing the resulting coatings by DSC to determine whether the required depressed melting point is present.

Figure 1C:
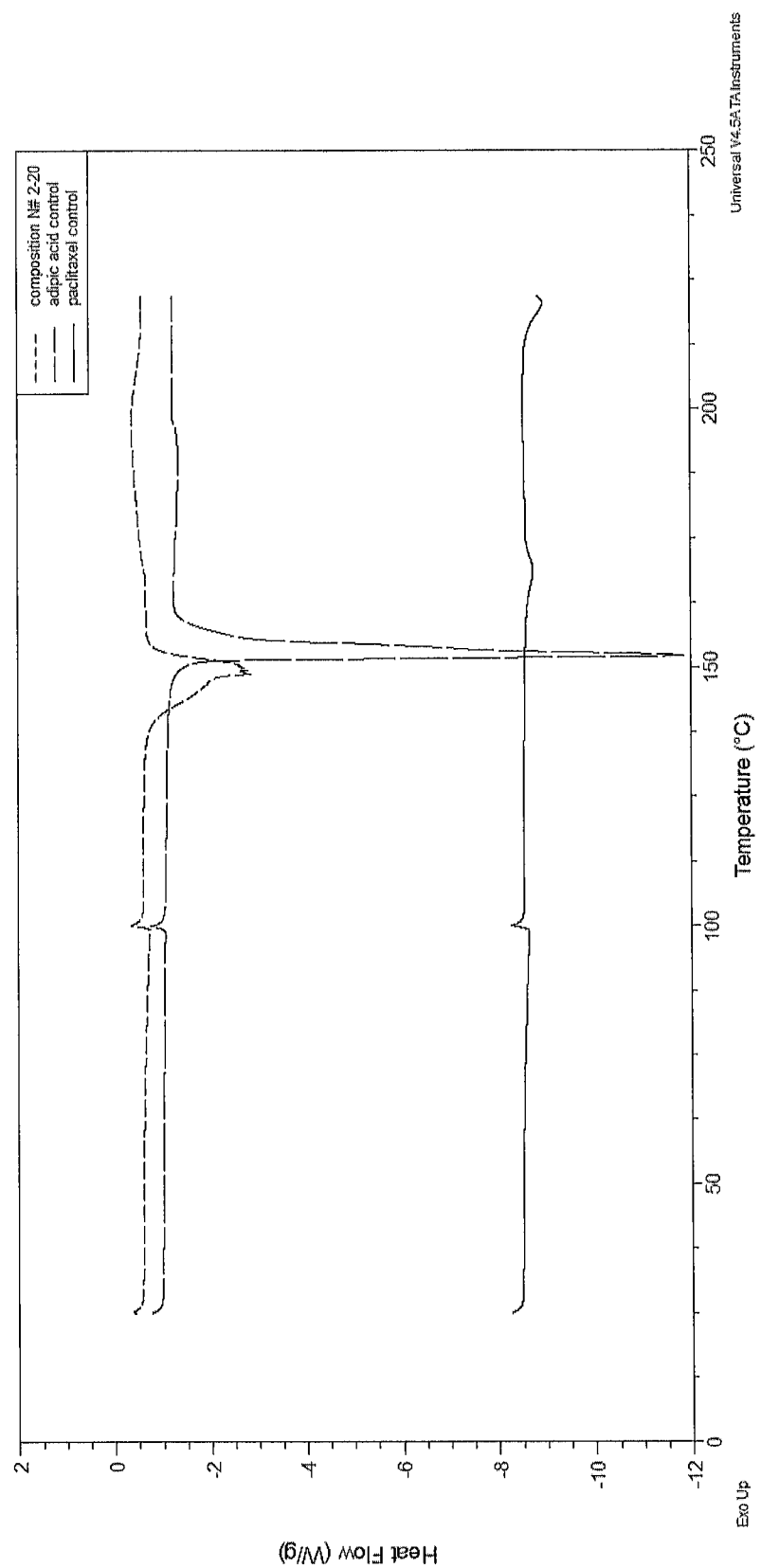

In one embodiment, substantially all of the particulate coating layer comprising paclitaxel and the at least one organic additive melts as a single phase at a lower temperature than the melting point of either the paclitaxel or the at least one organic additive when in pure form. In this embodiment, a DSC thermogram of the coating layer will show a single depressed melting point and no visible endotherm corresponding to the melting of pure paclitaxel or at least one pure organic additive. Examples of such thermograms are shown in FIGS. 1A to 1C, where it is evident that samples of paclitaxel-PABA (para-aminobenzoic acid), paclitaxel-succinic acid and paclitaxel-adipic acid compositions of the invention (prepared according to Example 1) all exhibited a single melting endotherm which was at a lower temperature than the endotherms for pure paclitaxel or PABA, succinic acid and adipic acid, respectively.

In one embodiment, 20-100% (by weight) of the coating or composition exhibits a depressed melting point (i.e. a melting point which is at a lower temperature than the melting point of the therapeutic agent and the at least one organic additive in pure form) such as 30-100%, 40-100%, 50-100%, 60-100%, 70-100%, 80-100% 90-100% or substantially all of the coating or composition exhibits a depressed melting point. In embodiments where less than 100% of the coating or composition is in a form which exhibits a depressed melting point, the remaining material will be paclitaxel in pure form, or at least one (if present) of the organic additives in pure form, or a mixture thereof.

Figure 8:
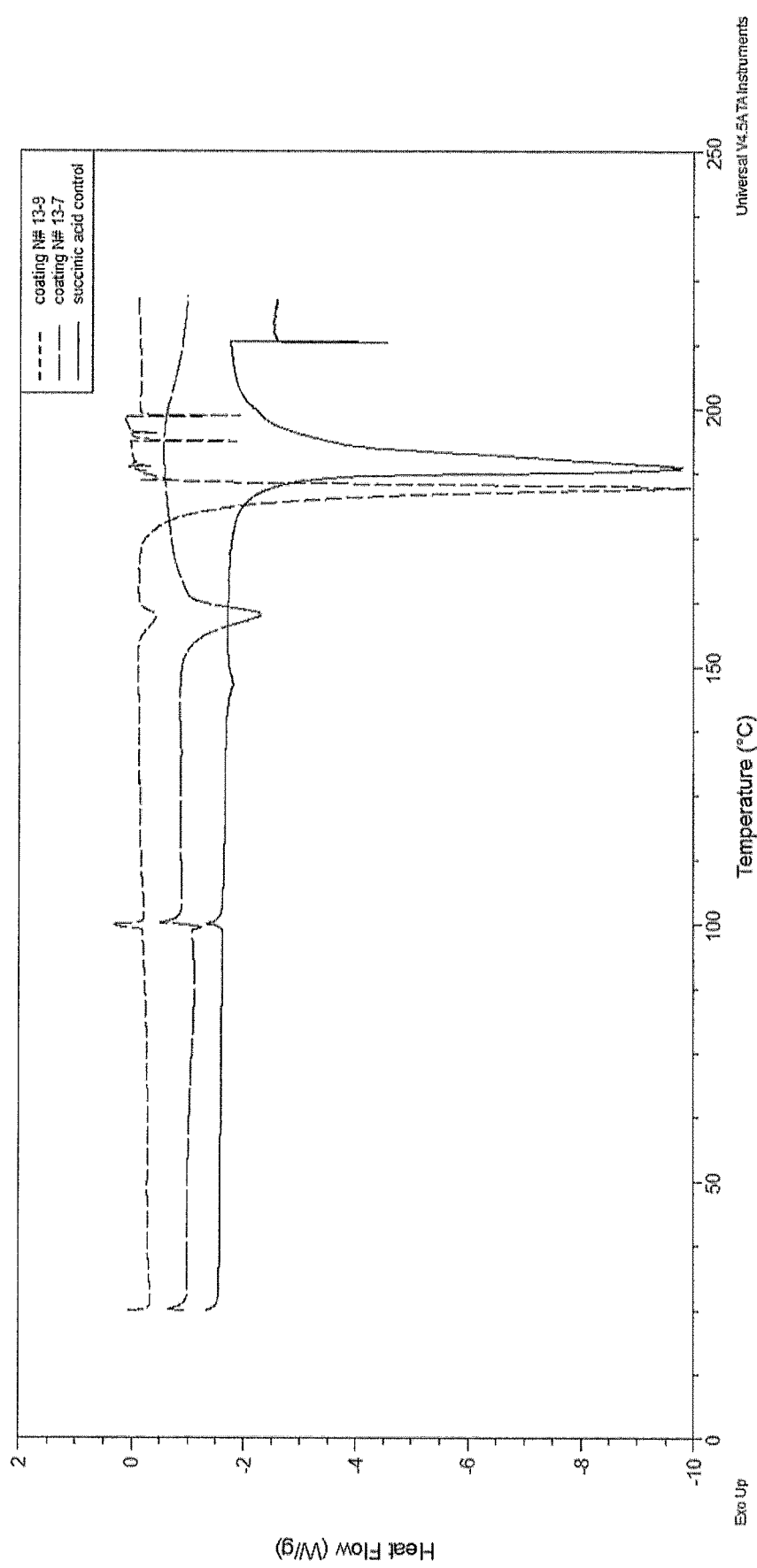
FIG. 8 shows a DSC thermogram of a paclitaxel-succinic acid coated balloon prepared according to Example 13 (paclitaxel:succinic acid=18:82 wt/wt) and compared to the paclitaxel-succinic acid coated balloon (paclitaxel:succinic acid=82:18 wt/wt), the DSC thermogram of which is shown in FIG. 7.

In one embodiment, a proportion of the particulate coating layer comprising paclitaxel and at least one organic additive melts as a single phase at a lower temperature than the melting point of either the paclitaxel or the at least one organic additive when in pure form, and the remaining particulate coating layer comprising paclitaxel and at least one organic additive melts at or close to the melting point of the at least one organic additive in pure form. In this embodiment, a DSC thermogram of the coating layer will show a single depressed melting point and an endotherm at or close to the known melting point for the at least one pure organic additive. In one embodiment, "close to" the known melting point means within ±10° C. of the known melting point for the pure organic additive, for example within ±5° C., within ±4° C., within ±3° C., within ±2° C. or within ±1° C. An example of such a thermogram is shown in FIG. 8 with a depressed melting endotherm at around 160° C. (corresponding to paclitaxel-succinic acid) and an endotherm at around 185° C., corresponding to the melting point of succinic acid in pure form (around 189° C.). In this embodiment, the proportion of organic additive which melts at a temperature at or close to the melting point of the organic additive in pure form is suitably lower than the proportion of organic additive in the paclitaxel-organic additive material which melts with a single depressed melting point. In a coating comprising two organic additives, a DSC thermogram may show a single depressed melting point and one or two endotherms corresponding to the known melting point of one, or both of the organic additives in pure form.

In one embodiment, the proportion of organic additive which melts at a temperature at or close to the melting point of the organic additive in pure form is 1-80% (wt %) of the organic additive in the coating or composition e.g. 1-70%, 1-60%, 1-50%, 1-40%, 1-30%, 1-20%, 1-10%, 1-5% or 1-2%.

In a further embodiment, a proportion of the particulate coating layer comprising paclitaxel and at least one organic additive melts as a single phase at a lower temperature than the melting point of either the paclitaxel or the at least one organic additive when in pure form, and the remaining particulate coating layer comprising paclitaxel and at least one organic additive melts at or close to the melting point of the paclitaxel in pure form. In this embodiment, a DSC thermogram of the coating layer will show a single depressed melting point and an endotherm at or close to the known melting point for paclitaxel. In this embodiment, the proportion of paclitaxel which melts at a temperature at or close to the melting point of the paclitaxel in pure form is suitably lower than the proportion of paclitaxel in the paclitaxel-organic additive material which melts with a single depressed melting point.

In one embodiment, the proportion of paclitaxel which melts at a temperature at or close to the melting point of the paclitaxel in pure form is 1-80% (wt %) of the paclitaxel in the coating or composition e.g. 1-70%, 1-60%, 1-50%, 1-40%, 1-30%, 1-20%, 1-10%, 1-5% or 1-2%.

In a still further embodiment, a proportion of the particulate coating layer comprising paclitaxel and at least one organic additive melts as a single phase at a lower temperature than the melting point of either the paclitaxel or the at least one organic additive when in pure form, and the remaining particulate coating layer comprising paclitaxel and at least one organic additive exhibits two melting endotherms: one at or close to the melting point of the paclitaxel in pure form and the other at or close to the melting point of the at least one organic additive in pure form. In this embodiment, a DSC thermogram of the coating layer will show a single depressed melting point and one endotherm at or close to the known melting point for paclitaxel and another endotherm at or close to the known melting point for the at least one organic additive. In this embodiment, the proportion of paclitaxel which melts at a temperature at or close to the melting point of the paclitaxel in pure form is suitably less that the proportion of paclitaxel in the paclitaxel-organic additive material which melts with a single depressed melting point, and the proportion of organic additive which melts at a temperature at or close to the melting point of the at least one organic additive in pure form is suitably less that the proportion of organic additive in the paclitaxel-organic additive material which melts with a single depressed melting point.

The relative proportions of 1) paclitaxel/organic additive composition exhibiting a depressed melting point; and 2) paclitaxel/organic additive composition with a melting point at or close to the melting point of pure paclitaxel and/or organic additive can be determined by DSC analysis because the area under the relevant endotherms can be correlated to the relative amount of each component 1) or 2) in the coating as a whole (in terms of weight, which can be converted to a molar ratio if required). A representative calculation is set out in Example 13.

As mentioned above, the coating layer or composition of the invention can be analysed by ultra-performance liquid chromatography (UPLC) and/or by mass spectrometry to determine the amount of paclitaxel in the coating layer or composition. When the weight % of paclitaxel in the solid coating is known, as in the case of a binary coating layer or composition (i.e. paclitaxel+one organic additive only) then the weight % of the organic additive can easily be determined as being 100−paclitaxel wt %.

In one embodiment, the weight % of therapeutic agent i.e. paclitaxel in the solid composition or coating is between about 5 wt. % and about 95 wt. %, for example between about 10 wt. % and about 95 wt. %, between about 20 wt. % and about 95 wt. %, between about 30 wt. % and about 90 wt. %, between about 45 wt. % and about 85 wt. %, between about 55 wt. % and about 70 wt. %, between about 40 wt. % and about 80 wt. %, between about 25 wt % and about 95 wt. %, between about 30 wt. % and about 85 wt. %, between about 70 wt. % and about 95 wt. %, 70 wt. % and about 80 wt. % or between about 75 wt. % and about 80 wt. %.

In one embodiment, the organic additive is PABA and the weight % of paclitaxel in the solid composition or coating layer is between about 30 wt. % and about 90 wt. %, for example between about 40 wt. % and about 80 wt. %. In one embodiment, the organic additive is PABA and the ratio (wt. %) of paclitaxel:PABA in the solid composition or coating layer is between about 3:7 and about 9:1, for example between about 2:3 and about 4:1.

In one embodiment, the organic additive is methyl paraben and the weight % of paclitaxel in the solid composition or coating layer is between about 45 wt. % and about 85 wt. %, for example between about 55 wt. % and about 70 wt. %. In one embodiment, the organic additive is methyl paraben and the ratio (wt. %) of paclitaxel:methyl paraben in the solid composition or coating layer is between about 4:5 and about 9:1, for example between about 1:1 and about 7:3.

In one embodiment, the organic additive is caffeine and the weight % of paclitaxel in the solid composition or coating layer is between about 70 wt. % and about 95 wt. %, for example between about 75 wt. % and about 90 wt. %. In one embodiment, the organic additive is caffeine and the ratio (wt. %) of paclitaxel:caffeine in the solid composition or coating layer is between about 7:3 and about 95:5, for example between about 3:1 and about 9:1 wt. %.

In one embodiment, the organic additive is calcium salicylate and the weight % of paclitaxel in the solid composition or coating layer is between about 70 wt. % and about 90 wt. %, for example between about 75 wt. % and about 80 wt. %. In one embodiment, the organic additive is calcium salicylate and the ratio (wt. %) of paclitaxel:calcium salicylate in the solid composition or coating layer is between about 7:3 and about 9:1, for example between about 3:1 and about 4:1.

In one embodiment, the organic additive is succinic acid and the weight % of paclitaxel in the solid composition or coating is between about 70 wt. % and about 90 wt. %, for example between about 75 wt. % and about 85 wt. %. In one embodiment, the organic additive is succinic acid and the ratio (wt. %) of paclitaxel:succinic acid in the solid composition or coating layer is between about 7:3 and about 9:1, for example between about 3:1 wt. % and about 6:1.

In one embodiment the organic additive is selected from the group consisting of p-aminobenzoic acid (PABA), saccharin, ascorbic acid, methyl paraben, caffeine, calcium salicylate, pentetic acid, creatinine, ethylurea, acetaminophen, aspirin, theobromine, tryptophan, succinic acid, glutaric acid, adipic acid, theophylline, and saccharin sodium, and weight % of paclitaxel in the solid composition or coating layer is between about 30 wt. % and about 90 wt. %, such as between about 50 wt. % and about 90 wt. %.

In one embodiment the organic additive is selected from the group consisting of p-aminobenzoic acid, saccharin, ascorbic acid, methyl paraben, caffeine, calcium salicylate, pentetic acid, creatinine, ethylurea, acetaminophen, aspirin, theobromine, tryptophan, succinic acid, glutaric acid, adipic acid, theophylline, and saccharin sodium, and the ratio (wt. %) of paclitaxel:organic additive is between about 3:7 and 9:1, such as between about 1:1 and about 9:1.

In one embodiment the organic additive is selected from the group consisting of p-aminobenzoic acid, methyl paraben, caffeine, calcium salicylate and succinic acid, and the weight % of paclitaxel in the solid composition or coating layer is between about 30 wt. % and about 90 wt. %, such as between about 50 wt. % and about 90 wt. %.

In one embodiment the organic additive is selected from the list consisting of p-aminobenzoic acid, methyl paraben, caffeine, calcium salicylate and succinic acid and the ratio (wt. %) of paclitaxel:organic additive is between about 3:7 and about 9:1, such as between about 1:1 and about 9:1.

The coating layer of the invention need not be applied directly to a surface of the medical device. Embodiments of medical devices coated with a composition of the invention can also include additional coatings underlying or overlaying the composition of the invention. Such additional coatings are separate and distinct from the coating layer of the invention. Such additional coatings can be used to increase adherence between the device surfaces and the composition of the invention or used to limit or meter elution of therapeutic agents from the composition. These additional coatings can include other therapeutic agents (such as those listed directly above), alone or in combination with various excipients or carriers. In one embodiment, the amount or thickness of the additional coating may be varied over the surface of the medical device. The additional coating layer can be continuous over an entire surface of the device or be discontinuous and cover only a portion or separate portions of the device. The additional coating layer can also be "sculpted" or modified to create a desired surface topography or texture.

In one embodiment, an adherent layer is interposed between the solid coating layer and the material of the surface of the device. The adherent layer, which is a separate and distinct layer underlying the paclitaxel-excipient coating layer improves the adherence of the drug coating layer to the surface of the medical device and further maintains the integrity of the coating, particularly during transit to the tissue to the be treated. In one embodiment, the adherent layer comprises a polymer, which is suitably biocompatible and avoids irritation of body tissue. Examples of such polymers include, but are not limited to polyolefins, polyisobutylene, ethylene-α-olefin copolymers, acrylic polymers and copolymers, polyvinyl chloride, polyvinyl methyl ether, polyvinylidene fluoride and polyvinylidene chloride, fluoropolymers, e.g. expanded polytetrafluoroethylene (ePTFE), polytetrafluoroethylene (PTFE), fluorinated ethylene-propylene (FEP), perfluorocarbon copolymers, e.g. tetrafluoroethylene perfluoroalkylvinyl ether (TFE/PAVE) copolymers, copolymers of tetrafluoroethylene (TFE) and perfluoromethyl vinyl ether (PMVE), copolymers of TFE with functional monomers that comprise acetate, alcohol, amine, amide, sulfonate, functional groups and the like as described in U.S. Pat. No. 8,658,707 (W. L. Gore and Associates, incorporated herein by reference, as well as combinations thereof), polyacrylonitrile, polyvinyl ketones, polystyrene, polyvinyl acetate, ethylene-methyl methacrylate copolymers, acrylonitrile-styrene copolymers, ABS resins, Nylon 12 and its block copolymers, polycaprolactone, polyoxymethylenes, polyethers, epoxy resins, polyurethanes, rayon-triacetate, cellulose, cellulose acetate, cellulose butyrate, cellophane, cellulose nitrate, cellulose propionate, cellulose ethers, carboxymethyl cellulose, chitins, polylactic acid, polyglycolic acid, polylactic acid-polyethylene oxide copolymers, polyethylene glycol, polypropylene glycol, polyvinyl alcohol, elastomeric polymers such as silicones (e.g., polysiloxanes and substituted polysiloxanes), polyurethanes, thermoplastic elastomers, ethylene vinyl acetate copolymers, polyolefin elastomers, EPDM rubbers and mixtures thereof.

In another embodiment, an additional coating layer comprising a therapeutic agent other than paclitaxel is interposed between the solid coating layer and the material of the surface of the device. Said coating layer is a separate and distinct layer underlying the paclitaxel-excipient coating layer and may provide a therapeutic benefit in addition to the benefit provided by the paclitaxel i.e. allowing for adjunctive therapies to be combined with the paclitaxel-organic additive. For example, a coating of the invention can be applied to a medical device already coated with an immobilized biologically active heparin coating, while maintaining the activity of both coatings (i.e. the anti-proliferative effect of the paclitaxel-organic additive composition and the antithrombin III (ATIII) binding activity of the heparin, as measured by known analytical methods. Thus, coated medical devices of the invention with a heparin bonded undercoating appear to have the added benefit of producing a reduction in sub-acute thrombosis after implantation. Example 7 describes such an embodiment, in which a vascular stent composed of nitinol and ePTFE was coated with a heparin bonded surface. The heparin-coated stent was then further coated with a paclitaxel-excipient composition of the invention (paclitaxel-caffeine). As shown in Example 8, the dual coated stent was found to demonstrate a high degree of durability. Furthermore, as described in Example 9, when the paclitaxel-excipient coating was removed from the surface of the stent, the underlying heparin-bonded surface had retained its ATIII activity. In one embodiment, the additional coating layer comprises a therapeutic agent other than paclitaxel. Alternatively, said additional coating layer comprising a therapeutic agent other than paclitaxel will overlay a portion, or all of the coating layer of the invention. As described above, such coating layer is a separate and distinct layer overlying the paclitaxel-organic additive(s) coating layer.

In one embodiment, the additional coating layer comprises a therapeutic agent selected from cilostazol, everolimus, dicumarol, zotarolimus, carvedilol, anti-thrombotic agents such as heparin, heparin derivatives, urokinase, and dextrophenylalanine proline arginine chloromethylketone; antiinflammatory agents such as dexamethasone, prednisolone, corticosterone, budesonide, estrogen, sulfasalazine and mesalamine, sirolimus and everolimus (and related analogs), anti-neoplastic/antiproliferative/anti-miotic agents such as major taxane domain-binding drugs, such as paclitaxel and analogues thereof, epothilone, discodermolide, docetaxel, paclitaxel protein-bound particles such as ABRAXANE® (ABRAXANE is a registered trademark of ABRAXIS BIOSCIENCE, LLC), paclitaxel complexed with an appropriate cyclodextrin (or cyclodextrin like molecule), rapamycin and analogues thereof, rapamycin (or rapamycin analogs) complexed with an appropriate cyclodextrin (or cyclodextrin like molecule), 17β-estradiol, 17β-estradiol complexed with an appropriate cyclodextrin, dicumarol, dicumarol complexed with an appropriate cyclodextrin, β-lapachone and analogues thereof, 5-fluorouracil, cisplatin, vinblastine, cladribine, vincristine, epothilones, endostatin, angiostatin, angiopeptin, monoclonal antibodies capable of blocking smooth muscle cell proliferation, and thymidine kinase inhibitors; lytic agents; anaesthetic agents such as lidocaine, bupivacaine and ropivacaine; anti-coagulants such as D-Phe-Pro-Arg chloromethyl ketone, an RGD peptide-containing compound, AZX100 a cell peptide that mimics HSP20 (Capstone Therapeutics Corp., USA), heparin, hirudin, antithrombin compounds, platelet receptor antagonists, antithrombin antibodies, anti-platelet receptor antibodies, aspirin, prostaglandin inhibitors, platelet inhibitors and tick antiplatelet peptides; vascular cell growth promoters such as growth factors, transcriptional activators, and translational promoters; vascular cell growth inhibitors such as growth factor inhibitors, growth factor receptor antagonists, transcriptional repressors, translational repressors, replication inhibitors, inhibitory antibodies, antibodies directed against growth factors, Afunctional molecules consisting of a growth factor and a cytotoxin, b (functional molecules consisting of an antibody and a cytotoxin; protein kinase and tyrosine kinase inhibitors (e.g., tyrphostins, genistein, quinoxalines); prostacyclin analogs; cholesterol-lowering agents; angiopoietins; antimicrobial agents such as triclosan, cephalosporins, aminoglycosides and nitrofurantoin; cytotoxic agents, cytostatic agents and cell proliferation affectors; vasodilating agents; agents that interfere with endogenous vasoactive mechanisms; inhibitors of leukocyte recruitment, such as monoclonal antibodies; cytokines; hormones, radiopaque agents such as iodinated contrast agents, gold, or barium, or a combination thereof. Suitably an additional coating layer comprises heparin.

In one embodiment, the medical device further comprises a protective top coat overlying the surface of the coating layer. The top coat may further minimise loss of the paclitaxel-excipient layer before it is brought into contact with target tissues, for example during device assembly and packaging, transit to the site to be treated, or if the device is a balloon or stent, during the first moments of inflation or expansion before coating layer is pressed into direct contact with target tissue. The top coat may be of particular use during crush loading, for example when an expandable medical device such as a balloon, stent, stent-graft or graft is coated in its expanded form, before being contracted into its non-expanded form. The contracted form of the coated device will usually be stored for a period of time before use. A top coating may prevent loss of the coating layer of the invention during storage and during expansion when the device is deployed. Alternatively, or additionally, the top coat may have lubricious properties to reduce frictional forces on the device while in transit. Suitably the top coat is degradable or soluble and will release slowly in the body lumen while protecting the drug layer. The top layer will erode more slowly if it is comprised of more hydrophobic, high molecular weight additives. Surfactants are examples of more hydrophobic structures with long fatty chains, such as Tween 20 and polyglyceryl oleate. High molecular weight additives include polyethylene oxide, polyethylene glycol, and polyvinyl pyrrolidone. Hydrophobic drug itself can act as a top layer component. For example, paclitaxel or rapamycin are hydrophobic. They can be used in the top layer. On the other hand, the top layer cannot erode too slowly or it might actually slow the release of drug during deployment at the target site. Other additives useful in the top coat include additives that strongly interact with drug or with the coating layer, such as p-isononylphenoxypolyglycidol, PEG laurate, Tween 20, Tween 40, Tween 60, PEG oleate, PEG stearate, PEG glyceryl laurate, PEG glyceryl oleate, PEG glyceryl stearate, polyglyceryl laurate, polyglyceryl oleate, polyglyceryl myristate, polyglyceryl palmitate, polyglyceryl-6 laurate, plyglyceryl-6 oleate, polyglyceryl-6 myristate, polyglyceryl-6 palmitate, polyglyceryl-10 laurate, plyglyceryl-10 oleate, polyglyceryl-10 myristate, polyglyceryl-10 palmitate PEG sorbitan monolaurate, PEG sorbitan monolaurate, PEG sorbitan monooleate, PEG sorbitan stearate, PEG oleyl ether, PEG laurayl ether, octoxynol, monoxynol, tyloxapol, sucrose monopalmitate, sucrose monolaurate, decanoyl-N-methylglucamide, n-decyl-[beta]-D-glucopyranoside, n-decyl-[beta]-D-maltopyranoside, n-dodecyl-[beta]-D-glucopyranoside, n-dodecyl-[beta]-D-maltoside, heptanoyl-N-methylglucamide, n-heptyl-[beta]-D-glucopyranoside, n-heptyk[beta]-D-thioglucoside, n-hexyl-[beta]-D-glucopyranoside, nonanoyl-N-methylglucamide, n-noyl-[beta]-D-glucopyranoside, octanoyl-N-methylglucamide, n-octyl-[beta]-D-glucopyranoside, octyl-[beta]-D-thioglucopyranoside; cysteine, tyrosine, tryptophan, leucine, isoleucine, phenylalanine, asparagine, aspartic acid, glutamic acid, and methionine; acetic anhydride, benzoic anhydride, ascorbic acid, 2-pyrrolidone-5-carboxylic acid, sodium pyrrolidone carboxylate, ethylenediaminetetraacetic dianhydride, maleic and anhydride, succinic anhydride, diglycolic anhydride, glutaric anhydride, acetiamine, benfotiamine, pantothenic acid; cetotiamine; cyclothiamine, dexpanthenol, niacinamide, nicotinic acid, pyridoxal 5-phosphate, nicotinamide ascorbate, riboflavin, riboflavin phosphate, thiamine, folic acid, menadiol diphosphate, menadione sodium bisulfite, menadoxime, vitamin B12, vitamin K5, vitamin K6, vitamin K6, and vitamin U; albumin, immunoglobulins, caseins, hemoglobins, lysozymes, immunoglobins, a-2-macroglobulin, fibronectins, vitronectins, fibrinogens, lipases, benzalkonium chloride, benzethonium chloride, docecyl trimethyl ammonium bromide, sodium docecylsulfates, dialkyl methylbenzyl ammonium chloride, and dialkylesters of sodium sulfosuccinic acid, L-ascorbic acid and its salt, D-glucoascorbic acid and its salt, tromethamine, triethanolamine, diethanolamine, meglumine, glucamine, amine alcohols, glucoheptonic acid, glucomic acid, hydroxyl ketone, hydroxyl lactone, glucono-lactone, glucoheptonolactone, glucooctanoic lactone, gulonic acid lactone, mannoic lactone, ribonic acid lactone, lactobionic acid, glucosamine, glutamic acid, benzyl alcohol, benzoic acid, hydroxybenzoic acid, propyl 4-hydroxybenzoate, lysine acetate salt, gentisic acid, lactobionic acid, lactitol, sinapic acid, vanillic acid, vanillin, methyl paraben, propyl paraben, sorbitol, xylitol, cyclodextrin, (2-hydroxypropyl)-cyclodextrin, acetaminophen, ibuprofen, retinoic acid, lysine acetate, gentisic acid, catechin, catechin gallate, tiletamine, ketamine, propofol, lactic acids, acetic acid, salts of any organic acid and organic amine, polyglycidol, glycerol, multiglycerols, galactitol, di(ethylene glycol), tri(ethylene glycol), tetra(ethylene glycol), penta(ethylene glycol), poly(ethylene glycol) oligomers, di(propylene glycol), tri (propylene glycol), tetra(propylene glycol), and penta(propylene glycol), poly(propylene glycol) oligomers, a block copolymer of polyethylene glycol and polypropylene glycol, PTFE, ePTFE and derivatives and combinations thereof.

As discussed above, the coated medical device of the invention may comprise an additional coating layer such as an adherent layer, an additional layer comprising a therapeutic agent or a top coat layer. It should be noted that such additional layers are considered to be distinct and separate layers to the coating layer of the invention which comprises paclitaxel and at least one organic additive and exhibits a depressed melting point. For example, while the coating layer of the invention (i.e. the coating layer which comprises the paclitaxel and at least one organic additive in a form exhibiting a depressed melting point) is surfactant-free, the medical device can have a distinct and separate coating layer comprising surfactant, either underlying or overlying the coating of the invention. Similarly, although in one embodiment the coating of the invention does not contain protein, the medical device may have a further coating layer, underlying or overlying the coating layer of the invention, which comprises protein. Thus, a component in the additional coating layer will not form part of the paclitaxel-excipient material which exhibits a depressed melting point.

In a situation where a medical device has multiple coating layers in addition to the coating layer of the invention, the presence of a depressed melting point may be difficult to confirm. However, in this situation, the presence of a melting point which does not correspond to any of the coating components is suggestive of the formation of paclitaxel-organic excipient material exhibiting a depressed melting point, particularly if the characteristic melting endotherms corresponding to paclitaxel and the organic excipient are also absent.

As discussed above, a particular challenge when developing a solid drug coating for a medical device is to achieve a balance between having sufficient adhesion to the device such that the coating is not lost/damaged in transit, yet also having suitable release characteristics such that the drug will transfer from the coating to the target tissue i.e. if the adhesion of the coating is too strong, the coating will be durable but an insufficient amount of the drug will be released and will result in suboptimal efficacy. Conversely, a coating may have excellent release characteristics but if the coating does not have sufficient adhesion to the device then an insufficient amount of drug will reach the target tissue, and unintentional release of the drug in areas other than the target tissue may be detrimental to the patient.

The coating layer of the present invention provides a good balance of good adhesion to a medical device, thereby minimising or even eliminating coating loss during transit of the device, and suitable release characteristics such that the paclitaxel is delivered in an effective and efficient manner to the target tissue. Paclitaxel-excipient compositions of the invention were coated onto balloons as described in Example 3, and the durability of the coatings was assessed using an adhesion test, as described in Example 4. The results of the experiment are summarised in FIG. 2 where it can be seen that the addition of an excipient increased adhesion of the coating to the balloon, as reflected by the lower % of drug coating lost during shaking for all coating layers containing an excipient. As noted in Example 4, the adherence of a paclitaxel-only coating was found to be prima facie so poor that it was not included in the test. Examples 5 and 6 describe in vitro and in vivo tests to examine balloons coated according to Example 2 for their efficacy in transferring paclitaxel from the balloon surface to a vascular tissue. As summarized in FIGS. 3, 5 and 6, significant transfer of paclitaxel from the surface of the balloon to the target tissue was observed.

In one embodiment, the coating of the invention has suitable adherence such that less than 40% of the paclitaxel is lost during shaking, for example less than 30%, less than 25%, less than 20%, less than 15%, less than 10% or less than 5%, using Test Method C, as described in Example 4.

In one embodiment, the coating of the invention has suitable release characteristics such that using Test Method A a coated balloon of the invention will release at least 50 µg drug per g tissue (µg/g), for example at least 60 µg/g, at least 70 µg/g or at least 80 µg/g of paclitaxel to the tested tissue, as described in Example 5.

The release characteristics of a composition of the invention may determine its suitability for a use in coating a particular type of medical device. Coatings of the invention which exhibit very fast release of paclitaxel are particularly suitable for use on DEBs, where once inflated the balloon is in contact with the target tissue for a relatively short amount of time before being removed. Conversely, a coating which exhibits relatively slower release of paclitaxel is better suited for use on a DES (or stent or stent graft (SSG)) which is retained within the vessel.

Therapeutic Methods

Medical devices coated with the novel paclitaxel-excipient compositions of the invention are of use in medical therapy.

In one aspect of the invention is provided a medical device with a coating layer as described hereinabove for use in treating tissue in the human or animal body. The tissue to be treated includes any body cavity, space, or hollow organ passage(s) such as blood vessels, the urinary tract, the intestinal tract, nasal cavity, neural sheath, intervertebral regions, bone cavities, esophagus, intrauterine spaces, pancreatic and bile ducts, rectum, and those previously intervened body spaces that have implanted vascular grafts, stents, prosthesis, or other type of medical implants.

The medical device with a coating layer as described herein can be of use in the removal of obstructions such as emboli and thrombi from blood vessels, as a dilation device to restore patency to an occluded body passage, as an occlusion device to selectively deliver a means to obstruct or fill a passage or space, and as a centering mechanism for transluminal instruments like catheters.

In one aspect of the invention is provided a medical device with a coating layer as described hereinabove for use in the prevention or treatment of stenosis or restenosis in a blood vessel of the human body. In another aspect of the invention is provided a medical device with a coating layer as described hereinabove for use in the prevention or treatment of stenosis or restenosis in a blood vessel of the human body, where previously placed eluting constructs have failed. In another embodiment, a medical device with a coating layer as described herein can be used to establish or maintain arteriovenous access sites, e.g., those used during kidney dialysis.

In one embodiment, said medical device with a coating layer as described herein can be used for Percutaneous Transluminal Angioplasty (PTA) in patients with obstructive disease of the peripheral arteries.

In another aspect of the invention is provided a method for the prevention or treatment of stenosis or restenosis which comprises inserting transiently or permanently into said blood vessel in the human body a medical device with a coating layer as described hereinabove.

Paclitaxel-excipient solid compositions exhibiting a depressed melting endotherm as described hereinabove are of use in coating an exterior surface of a medical device, but may have further utility per se as pharmaceutical compositions.

In one embodiment is provided a solid particulate composition comprising a therapeutic agent and at least one organic additive, wherein at least a proportion of the particulate composition melts as a single phase at a lower temperature than the melting point of the therapeutic agent and the at least one organic additive when in pure form; wherein the therapeutic agent is paclitaxel and wherein the at least one organic additive is independently selected from the list consisting of p-aminobenzoic acid, saccharin, ascorbic acid, methyl paraben, caffeine, calcium salicylate, pentetic acid, creatinine, ethylurea, acetaminophen, aspirin, theobromine, tryptophan, succinic acid, glutaric acid, adipic acid, theophylline, and saccharin sodium.

In another embodiment is provided a solid particulate composition comprising a mixture of components (a) a therapeutic agent and at least one organic additive in a particulate form which melts as a single phase at a lower temperature than the melting point of the therapeutic agent and the at least one organic additive when in pure form and (b) a component which is the organic additive in the form of particles which melt at a temperature at or close to that of the at least one organic additive in pure form; wherein the therapeutic agent is paclitaxel and wherein the at least one organic additive is independently selected from the list consisting of p-aminobenzoic acid, saccharin, ascorbic acid, methyl paraben, caffeine, calcium salicylate, pentetic acid, creatinine, ethylurea, acetaminophen, aspirin, theobromine, tryptophan, succinic acid, glutaric acid, adipic acid, theophylline, and saccharin sodium.

Suitably the solid composition comprises at least one organic additive independently selected from calcium salicylate, caffeine, methyl paraben, p-aminobenzoic acid and succinic acid. In one embodiment, the solid composition comprises succinic acid as the single organic additive or as one of a number of organic additives. In one embodiment is provided a solid particulate composition as described herein above in the form a coating applied to a surface. Suitably the surface is the exterior surface of a medical device. It should be noted that all embodiments described above with respect to the coating of the invention apply equally to the solid composition of the invention.

In another embodiment is provided a solid particulate composition as described hereinabove for use in the prevention or treatment of stenosis or restenosis. In a further embodiment is provided a solid particulate composition as described hereinabove for the treatment of cancer, in particular cancers of the ovary, breast, lung, oesophagus, head and neck region, bladder, prostate, brain, liver, colon and lymphomas. The solid particulate composition can be administered by any convenient method, e.g. by oral, inhalation, parenteral (including injection or infusion), buccal, sublingual, nasal, rectal or transdermal administration and the pharmaceutical compositions adapted accordingly.

The coated medical device of the invention will typically comprise a single dose of paclitaxel. The dose of paclitaxel delivered will depend on many factors including the size of the coated area, the length of time the coated device is in contact with the target tissue and the amount of paclitaxel in the coating. Suitably the medical device has a coating layer containing an average of 0.1-10 µg/mm$^2$ of paclitaxel, such as 0.2-8 µg/mm$^2$, 0.5-5 µg/mm$^2$, or 1-4 µg/mm$^2$ e.g. 2 µg/mm$^2$, 3 µg/mm$^2$ or 4 µg/mm$^2$ of paclitaxel. The apparent coated surface area does not take account of porosity considerations of a porous substrate material. If the substrate material is porous, the effect of porosity on surface area is not considered for these calculations. For example, the apparent surface area of a cylindrical tubular ePTFE vascular graft (which is made of a porous material) with a paclitaxel-excipient coating of the invention comprising the inner surface of the tubular graft is calculated as it is for any cylindrical geometry as 2πrl: where r is the graft inner radius; L is the axial length; and π is the number pi. It is important to note that the porous nature of ePTFE and its effect on surface area is not accounted for herein. Accordingly, non-porous substrate materials that are cut into squares for analysis are taken to have a surface area of the length multiplied by the width.

The coated medical device of the invention will typically contain 0.1-300 mg of paclitaxel in total, for example 0.1-250 mg, 0.1-200 mg, 0.1-150 mg, 0.1-100 mg, 0.1-90 mg, 0.1-80 mg, 0.1-70 mg, 0.1-60 mg, 0.1-50 mg, 0.1-40 mg, 0.1-30 mg, 0.2-20 mg, 0.2-10 mg or 0.2-5 mg. In one embodiment, the coated medical device is a balloon and the coating layer contains 20 mg of paclitaxel in total. In one embodiment, the coated medical device is a stent and the coating layer contains 10 mg of paclitaxel in total. In one embodiment, the coated medical device is a stent graft and the coating layer contains 10 mg of paclitaxel in total.

Methods for Preparing Compositions and Coatings of the Invention

Solid paclitaxel-excipient particulate compositions can be prepared by a multitude of methods. One method involves adding saturated solutions of excipient to a vial containing cast paclitaxel film. The mixture is stirred until a precipitate is formed, which is then filtered and dried to yield the particulate composition. Suitably the at least one organic additive is dissolved in acetone or a mixture of acetone/water for example between about 50/50 and 95/5, between about 60/40 and 90/10, between about 70/30 and about 90/10 or between about 70/30 and about 75/25 acetone/water (v/v), such as 90/10, 75/25 or 70/30 acetone/water (v/v). A representative procedure is described in Example 1.

Another method of preparing a coating of the invention is by evaporation of a solution of paclitaxel and the at least one organic additive applied to a device. Suitably, the solution of the paclitaxel and the at least one organic additive is a solution in a solvent selected from water, acetone and mixtures thereof, for example between about 50/50 and 95/5, between about 60/40 and 90/10, between about 70/30 and about 90/10 or between about 70/30 and about 75/25 acetone/water (v/v), such as 90/10, 75/25 or 70/30 acetone/ water (v/v). Thus, in one aspect of the invention is provided a method for preparing a medical device with a coating layer as described herein which comprises the steps of dissolving the therapeutic agent and the at least one organic additive in a solvent to form a solution, coating the device with the solution and evaporating the solvent.

A coating of the invention may be applied to a medical device using a method which involves minimal solvent, or indeed no solvent. For example, a dry powder method may be used which involves combining the paclitaxel and at least one organic additive in powder form before applying to the device to form a solid particulate composition, optionally followed by thermal treatment. The powder mixture of paclitaxel and at least one organic additive is suitably spayed on to the device, which optionally comprises an adhesive layer (as described hereinabove), which may be followed by thermal treatment, for example, to affix the layer to the surface of the device.

Thus, in one embodiment is provided a method for preparing a medical device as described herein above which comprises the steps of combining the therapeutic agent and the at least one organic additive in powder form, and then applying the powder to the device to form a solid particulate composition. An additional thermal treatment step may subsequently be applied, for example to affix the coating to the surface of the medical device.

Various methods for forming the coating of the invention by evaporation of a solution of paclitaxel and at least one organic additive can used. The solution of paclitaxel and at least one organic additive can be pipetted over the exterior surface of the device, which is itself under rotation, e.g. pipetting 90-100 ul of the coating solution over the device at a time. Alternatively, the device can simply be dipped into the solution of paclitaxel and at least one organic additive, removed and then air dried. The dipping and drying process can be repeated as many times as is necessary to achieve the desired coating thickness or loading of paclitaxel. Other techniques such as casting, spinning, spraying, ink jet printing, electrostatic techniques, painting, dispersion coating, powder coating, or combinations thereof may be used to form the coating.

Following application of the coating a drying step may be required. The coating drying environment may be controlled as a function of time, such as by controlling/modulating the air composition, flow rate and flow patterns, air temperature, localized heating (e.g., heat lamp), etc, to thereby control physical properties of the coating.

In one embodiment, the or an organic additive is PABA and the weight % of paclitaxel in the pipetting/dipping solution (based on the total weight of solid components added) is between about 30 wt. % and about 90 wt. %, for example between about 40 wt. % and about 80 wt. %. In one embodiment, the or an organic additive is PABA and the ratio (wt. %) of paclitaxel:PABA in the pipetting/dipping solution (based on the total weight of solid components added) is between about 3:7 and about 9:1, for example between about 2:3 and about 4:1.

In one embodiment, the or an organic additive is PABA and the ratio (wt. %) of paclitaxel:PABA in the pipetting/dipping solution (based on the total weight of solid components added) is between about 3:7 and about 9:1, for example between about 2:3 and about 4:1, wherein the dipping/pipetting solution is a solution of between about 70/30 and about 90/10 acetone/water (v/v).

In one embodiment, the or an organic additive is methyl paraben and the weight % of paclitaxel in the pipetting/dipping solution (based on the total weight of solid components added) is between about 45 wt. % and about 85 wt. %, for example between about 55 wt. % and about 70 wt. %. In one embodiment, the or an organic additive is methyl paraben and the ratio (wt. %) of paclitaxel:methyl paraben in the pipetting/dipping solution (based on the total weight of solid components added) is between about 4:5 and about 9:1, for example between about 1:1 and about 7:3.

In one embodiment, the or an organic additive is methyl paraben and the ratio (wt. %) of paclitaxel:methyl paraben in the pipetting/dipping solution (based on the total weight of solid components added) is between about 4:5 and about 9:1, for example between about 1:1 and about 7:3, wherein the dipping/pipetting solution is a solution of between about 70/30 and about 90/10 acetone/water (v/v).

In one embodiment, the or an organic additive is caffeine and the weight % of paclitaxel in the pipetting/dipping solution (based on the total weight of solid components added) is between about 70 wt. % and about 95 wt. %, for example between about 75 wt. % and about 90 wt. %. In one embodiment, the or an organic additive is caffeine and the ratio (wt. %) of paclitaxel:caffeine in the pipetting/dipping solution (based on the total weight of solid components added) is between about 7:3 and about 95:5, for example between about 3:1 and about 9:1 wt. %.

In one embodiment, the or an organic additive is caffeine and the ratio (wt. %) of paclitaxel:caffeine in the pipetting/dipping solution (based on the total weight of solid components added) is between about 7:3 and about 95:5, for example between about 3:1 and about 9:1, wherein the dipping/pipetting solution is a solution of between about 70/30 and about 90/10 acetone/water (v/v).

In one embodiment, the or an organic additive is calcium salicylate and the weight % of paclitaxel in the pipetting/dipping solution (based on the total weight of solid components added) is between about 70 wt. % and about 90 wt. %, for example between about 75 wt. % and about 80 wt. %. In one embodiment, the or an organic additive is calcium salicylate and the ratio (wt. %) of paclitaxel:calcium salicylate in the pipetting/dipping solution (based on the total weight of solid components added) is between about 7:3 and about 9:1, for example between about 3:1 and about 4:1.

In one embodiment, the or an organic additive is calcium salicylate and the ratio (wt. %) of paclitaxel:calcium salicylate in the pipetting/dipping solution (based on the total weight of solid components added) is between about 7:3 and about 9:1, for example between about 3:1 and about 4:1, wherein the dipping/pipetting solution is a solution of between about 70/30 and about 90/10 acetone/water (v/v).

In one embodiment, the or an organic additive is succinic acid and the weight % of paclitaxel in the pipetting/dipping solution (based on the total weight of solid components added) is between about 70 wt. % and about 90 wt. %, for example between about 75 wt. % and about 85 wt. %. In one embodiment, the or an organic additive is succinic acid and the ratio (wt. %) of paclitaxel:succinic acid in the pipetting/dipping solution (based on the total weight of solid components added) is between about 7:3 and about 9:1, for example between about 3:1 wt. % and about 6:1.

In one embodiment, the or an organic additive is succinic acid and the ratio (wt. %) of paclitaxel:succinic acid in the pipetting/dipping solution (based on the total weight of solid components added) is between about 7:3 and about 9:1, for example between about 3:1 wt. % and about 6:1, wherein the dipping/pipetting solution is a solution of between about 70/30 and about 90/10 acetone/water (v/v).

In one embodiment the at least one organic additive is independently selected from the group consisting of p-aminobenzoic acid, saccharin, ascorbic acid, methyl paraben, caffeine, calcium salicylate, pentetic acid, creatinine, ethylurea, acetaminophen, aspirin, theobromine, tryptophan, succinic acid, glutaric acid, adipic acid, theophylline, and saccharin sodium, and the weight % of paclitaxel in the pipetting/dipping solution (based on the total weight of solid components added) is between about 30 wt. % and about 90 wt. %, such as between about 50 wt. % and about 90 wt. %.

In one embodiment the at least one organic additive is independently selected from the group consisting of p-aminobenzoic acid, saccharin, ascorbic acid, methyl paraben, caffeine, calcium salicylate, pentetic acid, creatinine, ethylurea, acetaminophen, aspirin, theobromine, tryptophan, succinic acid, glutaric acid, adipic acid, theophylline, and saccharin sodium, and the ratio (wt. %) of paclitaxel:organic additive (total) in the pipetting/dipping solution (based on the total weight of solid components added) is between about 3:7 and about 9:1, such as between about 1:1 and about 9:1.

In one embodiment the at least one organic additive is independently selected from the group consisting of p-aminobenzoic acid, saccharin, ascorbic acid, methyl paraben, caffeine, calcium salicylate, pentetic acid, creatinine, ethylurea, acetaminophen, aspirin, theobromine, tryptophan, succinic acid, glutaric acid, adipic acid, theophylline, and saccharin sodium, and the ratio (wt. %) of paclitaxel:organic additive (total) in the pipetting/dipping solution (based on the total weight of solid components added) is between about 3:7 and about 9:1, such as between about 1:1 and about 9:1, wherein the dipping/pipetting solution is a solution of between about 70/30 and about 90/10 acetone/water (v/v).

In one embodiment, the at least one organic additive is independently selected from the list consisting of p-aminobenzoic acid, methyl paraben, caffeine, calcium salicylate and succinic acid and the weight % of paclitaxel in the pipetting/dipping solution (based on the total weight of solid components added) is between about 30 wt. % and about 90 wt. %, such as between about 50 wt. % and about 90 wt. %.

In one embodiment, the at least one organic additive is independently selected from the list consisting of p-aminobenzoic acid, methyl paraben, caffeine, calcium salicylate and succinic acid and the ratio (wt. %) of paclitaxel:organic additive (total) in the pipetting/dipping solution (based on the total weight of solid components added) is between about 3:7 and about 9:1, such as between about 1:1 and about 9:1.

In one embodiment, the at least one organic additive is independently selected from the list consisting of p-aminobenzoic acid, methyl paraben, caffeine, calcium salicylate and succinic acid and the ratio (wt. %) of paclitaxel:organic additive (total) in the pipetting/dipping solution (based on the total weight of solid components added) is between about 3:7 and about 9:1, such as between about 1:1 and about 9:1, wherein the dipping/pipetting solution is a solution of between about 70/30 and about 90/10 acetone/water (v/v).

In one embodiment, the organic additive is succinic acid and the ratio (wt. %) of paclitaxel:succinic acid in the pipetting/dipping solution (based on the total weight of solid components added) is between about 3:1 and about 6:1, wherein the dipping/pipetting solution is a solution of between about 70/30 and about 90/10 acetone/water (v/v).

Typically, the coating of the invention will have an average total thickness of about 0.1 µm to about 200 µm, such as about 0.2 µm to about 100 µm. Coating thickness can be measured using a suitable coating thickness analyser or gauge.

It should be noted that the methods of preparing the coating layer or composition of the invention described above (e.g. dry powder methods and solvent evaporation methods) are all equally suitable for preparing the various coating and composition embodiments described hereinabove.

Further Embodiments of the Invention

In one aspect of the invention is provided a medical device for delivering a therapeutic agent to a tissue, the device having a solid particulate coating layer applied to an exterior surface of the device, said surface being composed of a material selected from nylon and ePTFE, the coating layer comprising a therapeutic agent and at least one organic additive; wherein at least a proportion of the particulate coating layer comprising the therapeutic agent and the at least one organic additive melts as a single phase at a lower temperature than the melting point of the therapeutic agent and the at least one organic additive when in pure form; wherein the therapeutic agent is paclitaxel and wherein the at least one organic additive is independently selected from the list consisting of calcium salicylate, caffeine, methyl paraben, p-aminobenzoic acid and succinic acid.

In another aspect of the invention is provided a medical device for delivering a therapeutic agent to a tissue, the device having a solid surfactant-free particulate coating layer applied to an exterior surface of the device, the coating layer comprising a therapeutic agent and at least one non-polymeric organic additive which is hydrolytically stable; wherein the particulate coating layer comprises a mixture of components (a) the therapeutic agent and the at least one organic additive in a form which melts as a single phase at a lower temperature than the melting point of the therapeutic agent and the at least one organic additive when in pure form and (b) the at least one organic additive in a form which melts at a temperature at or close to that of said organic additive in pure form; wherein the therapeutic agent is paclitaxel; and wherein the therapeutic agent, when formulated in the coating layer, is stable to ethylene oxide sterilization.

In a further aspect of the invention is provided a medical device for delivering a therapeutic agent to a tissue, the device having a solid surfactant-free particulate coating layer applied to an exterior surface of the device, the coating layer comprising a therapeutic agent and at least one non-polymeric organic additive which is hydrolytically stable; wherein the particulate coating layer is formed by evaporation of a solution of the therapeutic agent and the at least one organic additive applied to the device to form a solid particulate composition, wherein at least a proportion of the particulate coating layer melts as a single phase at a lower temperature than the melting point of the therapeutic and the at least one organic additive when in pure form; wherein the therapeutic agent is paclitaxel; and wherein the therapeutic agent, when formulated in the coating layer, is stable to ethylene oxide sterilization.

In a further aspect of the invention is provided a medical device for delivering a therapeutic agent to a tissue, the device having a solid particulate coating layer applied to an exterior surface of the device, said surface being composed of a material selected from nylon and ePTFE, the coating layer comprising a therapeutic agent and at least one organic additive; wherein the coating layer is formed by evaporation of a solution of the therapeutic agent and the at least one organic additive applied to the device to form a solid particulate composition, wherein at least a proportion of the particulate coating layer melts as a single phase at a lower temperature than the melting point of either the therapeutic agent or the at least one organic additive when in pure form; wherein the therapeutic agent is paclitaxel, wherein the at least one organic additive is independently selected from the list consisting of calcium salicylate, caffeine, methyl paraben, p-aminobenzoic acid and succinic acid and wherein the solution of the therapeutic agent and the at least one organic additive is a solution in a solvent selected from water, acetone and mixtures thereof.

In a further aspect of the invention is provided a medical device for delivering a therapeutic agent to a tissue, the device having a solid surfactant-free particulate coating layer applied to an exterior surface of the device, the coating layer comprising a therapeutic agent and at least one non-polymeric organic additive which is hydrolytically stable; wherein the particulate coating layer is formed by evaporation of a solution of the therapeutic agent and the at least one organic additive applied to the device to form a solid particulate composition comprising (a) a component which melts as a single phase at a lower temperature than the melting point of either the therapeutic agent or the at least one organic additive when in pure form and (b) a component which melts at a temperature at or close to that of the at least one organic additive in pure form; wherein the therapeutic agent is paclitaxel; and wherein the therapeutic agent, when formulated in the coating layer, is stable to ethylene oxide sterilization.

In a further aspect of the invention is provided a medical device for delivering a therapeutic agent to a tissue, the device having a solid surfactant-free particulate coating layer applied to an exterior surface of the device, the coating layer comprising a therapeutic agent and at least one organic additive independently selected from the list consisting of p-aminobenzoic acid, saccharin, ascorbic acid, methyl paraben, caffeine, calcium salicylate, pentetic acid, creatinine, ethylurea, acetaminophen, aspirin, theobromine, tryptophan, succinic acid, glutaric acid, adipic acid, theophylline, and saccharin sodium; wherein at least a proportion of the particulate coating layer comprising the therapeutic agent and the at least one organic additive melts as a single phase at a lower temperature than the melting point of either the therapeutic or the at least one organic additive when in pure form; and wherein the therapeutic agent is paclitaxel.

In a further aspect of the invention is provided a medical device for delivering a therapeutic agent to a tissue, the device having a solid surfactant-free particulate coating layer applied to a surface of the device, the coating layer comprising a therapeutic agent and at least one non-polymeric organic additive which is hydrolytically stable; wherein the particulate coating layer is formed by combining the therapeutic agent and at least one organic additive in powder form, and then applying the powder to the device (with an optional subsequent step of thermal treatment) to form a solid particulate composition, wherein at least a proportion of the particulate coating layer comprising the therapeutic agent and the at least one organic additive melts as a single phase at a lower temperature than the melting point of the therapeutic agent and the organic additive when in pure form; wherein the therapeutic agent is paclitaxel; and wherein the therapeutic agent, when formulated in the coating layer, is stable to sterilization.

In a further aspect of the invention is provided a medical device for delivering a therapeutic agent to a tissue, the device having a solid particulate coating layer applied to an exterior surface of the device, said surface being composed of a material selected from nylon and ePTFE, the coating layer comprising a therapeutic agent and at least one organic additive; wherein the coating layer is formed by combining the therapeutic agent and at least one organic additive in powder form, and then applying the powder to the device (with an optional subsequent step of thermal treatment) to form a solid particulate composition, wherein at least a proportion of the particulate coating layer melts as a single phase at a lower temperature than the melting point of the therapeutic agent and the at least one organic additive when in pure form; wherein the therapeutic agent is paclitaxel, wherein the at least one organic additive is independently selected from the list consisting of calcium salicylate, caffeine, methyl paraben, p-aminobenzoic acid and succinic acid.

In a further aspect of the invention is provided a medical device for delivering a therapeutic agent to a tissue, the device having a solid surfactant-free particulate coating layer applied to an exterior surface of the device, the coating layer comprising a therapeutic agent and at least one non-polymeric organic additive which is hydrolytically stable; wherein the particulate coating layer is formed by combining the therapeutic agent and the at least one organic additive in powder form, and then applying the powder to the device (with an optional subsequent step of thermal treatment) to form a solid particulate composition comprising (a) a component comprising the therapeutic agent and the at least one organic additive which melts as a single phase at a lower temperature than the melting point of the therapeutic agent and the organic additive when in pure form and (b) a component which melts at a temperature at or close to that of the at least one organic additive in pure form; wherein the therapeutic agent is paclitaxel and wherein the therapeutic agent, when formulated in the coating layer, is stable to sterilization.

Coatings and compositions according to the present invention are expected to have one or more of the following merits or advantages:

good adherence to a medical device during crush loading and storage e.g. as measured using Test Method C;

good adherence to a medical device during tracking and insertion, e.g. as measured using Test Method C;

suitable release characteristics, and in certain embodiments, rapid release characteristics upon contact with the target tissue e.g. as measured in Test Method A or Test Method B.

good stability of the formulated therapeutic agent to sterilization e.g. as measured using Test Method D (ethylene oxide sterilization), Test Method E (electron beam sterilization), Test Method F (vapour hydrogen peroxide sterilization) or Test Method G (plasma hydrogen peroxide sterilization);

compatibility with additional therapeutic agents, such as heparin.

The invention embraces all combinations of indicated groups and embodiments of groups recited above.

All patents and patent applications referred to herein are incorporated by reference in their entirety.

Definitions and Abbreviations

DEB drug eluting balloon
DES drug eluting stent
DSC differential scanning calorimetry
ePTFE expanded polytetrafluoroethylene
h hour
HPLC high-performance liquid chromatography ND not determined
PABA p-aminobenzoic acid
PEG polyethylene glycol
PBS phosphate buffered saline
PLGA poly(lactic-co-glycolic) acid
PVP polyvinylpyrrolidone
SSG stent or stent graft
UPLC ultra-performance liquid chromatography

EXAMPLES

General Procedures
Chemicals

Anhydrous crystalline paclitaxel was purchased from Indena. Hydrated crystalline paclitaxel was purchased from LC labs (P-9600 ASM-114). Deuterated paclitaxel was obtained from Toronto Research Chemicals, Inc.
Solvent Acetone ("dry" with <0.5% water) was purchased from Sigma.
Materials Nylon balloon catheters having dimensions of 5 mm in diameter and 40 mm in length and 7 mm diameter and 120 mm in length were obtained (Bavaria Medizin Technologie, Weßling, Germany, model #BMT-035, article #08GL-504A, 5×40 mm, article #08QL-712B, 7×120 mm). Porcine carotid arteries were obtained from Animal Technologies Inc. (Tyler, Texas). Luer fittings (#11570) were purchased from Qosina (Edgewood, New York).
Evaluation Methods The parameter being evaluated by each method is given in parentheses.
Differential Scanning Calorimetry (DSC) Analysis (Peak Melting Endotherm Determination)

A solid sample was added to a DSC pan. The mass of the sample was weighed, and the pan sealed with pinhole lids. The sample was examined using DSC (model #Q2000, TA Instruments), by equilibrating at 25° C., ramping 10° C./min to 100° C., dwelling at 100° C. for 20 min (to remove any trace solvent, in particular acetone or acetone:water), ramping 10° C./min to 225° C.
Ultra-Performance Liquid Chromatography (UPLC) Analysis (Paclitaxel Concentration)

UPLC analysis was carried out using a Waters instrument (model #ACQUITY). The identification of paclitaxel was determined by the retention time of paclitaxel. The concentration of paclitaxel was directly proportional to the integrated peak area, which was determined by external standardization. Samples were dissolved in a sample diluent or submerged in an extraction solvent and shaken for one hour. Paclitaxel standards were prepared by serial dilution of pure paclitaxel in the sample diluent. All samples and standards were protected from light during preparation. UPLC chromatography parameters were: phenyl column (1.7 um, 2.1× 50 mm); mobile phase 2 mM ammonium acetate:0.2% acetic acid; flow rate 0.6 ml/min; run time 3 min; injection volume 2 ul; purge solvent methanol:water (60:40 v/v); wash solvent acetonitrile; column temperature 60° C.; UV detector wavelength 227.0±1.2 nm; sample rate 20 points/sec.
Tandem Mass Spectrometry (Detection and Quantification of Paclitaxel)

Tandem mass spectrometry was carried out using a Waters Xevo TQ-S instrument. The sodium adduct of paclitaxel was used. Mass spectrometry parameters were ESI mode positive; 2 kV capillary; 50V source offset; 7.0 bar nebulizer; 150 L/hr cone gas flow; collision gas argon 0.15 ml/min.

Test Methods
Test Method A—In Vitro Tissue Transfer and Uptake Test—Balloon

Coated balloons are examined for their ability to transfer paclitaxel from the balloon surface to a vascular tissue in an in vitro model. Porcine carotid arteries from 6-9 month old pigs, approximately 6 cm in length, were trimmed of adipose tissue, and fitted at their distal end with Luer fittings using wax thread. The vessel diameters at the proximal and distal ends were approximately 5 mm and 2 mm, respectively (vessels tapered as a function of length). They were flushed with 12 ml of PBS and pinned to a dissecting pad under a slight axial stretch to straighten the vessel. The coated balloons, all 5×40 mm (diameter×length) were inserted into the proximal ends of the vessels to the middle of the vessel, held at this position for 30 sec, inflated to 6 atm pressure for 1 min, deflated and removed. A Luer fitting was fitted to the proximal end with wax thread. Tubing was connected to the proximal and distal fittings, and the vessel was flushed with PBS at 60 ml/min for 1 hr at 37° C. The vessel was analyzed for paclitaxel content using UPLC/Tandem Mass Spectrometry. The coating of the invention has suitable paclitaxel release and tissue transfer characteristics from a balloon such that the measured drug concentration in the tissue at the 1 hr timepoint is at least 20 μg drug per g tissue (μg/g), for example at least 50 μg/g, at least 60 μg/g, at least 70 μg/g or at least 80 μg/g.
Test Method B—In Vitro Tissue Transfer and Uptake Test-Stent Coated stents are examined for their ability to transfer paclitaxel from the stent surface to a vascular tissue in an in vitro model as essentially described by Liao (D. Liao et al., Biochem Biophys Res Commun, 372(4): 668-673, 2008. "Vascular smooth cell proliferation in perfusion culture of porcine carotid arteries"). The coated stent was compacted diametrically to an outer diameter of 3.36 mm using means known to those of skill in the art of self-expanding stents. The stents were constrained in the compacted state within a constraint tube with an inner diameter of 3.36 mm. The compacted stent was inserted into the proximal end of the porcine vessel to the middle of the vessel, and deployed to its expanded state. A Luer fitting was fitted to the proximal end with wax thread. Tubing was connected to the proximal and distal fittings, and the vessel was flushed with PBS at 60 ml/min for 24 hr at 37° C. The stent was removed, and vessel was analyzed for paclitaxel content using LC/MS-MS according to General Procedures. The coating of the invention has suitable paclitaxel release and tissue transfer characteristics from a stent such that the measured drug concentration in the tissue at the 24 hr timepoint is at least 1 μg drug per g tissue (μg/g), for example at least 2.5 μg/g, at least 5 μg/g or at least 10 μg/g.
Test Method C—Coating Adherence Test This test measures coating adherence to a medical device such as a stent or balloon catheter and is intended to gauge coating adhesion and durability relative to other coatings. The entire coated device is placed in a 15 ml glass test tube. While at its minimum diameter (e.g. in the case a balloon catheter, at its un-inflated diameter), the device is tapped against the test tube walls for 30 sec. After 30 sec, the device is removed from the test tube. The test tube is capped and submitted for UPLC analysis of paclitaxel content. The percent of paclitaxel lost during shaking is calculated by dividing the amount found in the test tube by the estimated initial amount coated on the balloon (estimated by pipetting a known solution volume with a known paclitaxel concentration).

The coating of the invention has suitable adherence such that less than 40% of the paclitaxel is lost during shaking, for example less than 30%, less than 25%, less than 20%, less than 15%, less than 10% or less than 5%.

Test Method D—Stability to Ethylene Oxide

A sample of a composition of the invention or a coated device of the invention was placed in a breathable polyethylene pouch (e.g. a Tyvek pouch) and subjected to at least 12 hours preconditioning at 43° C. and 65% relative humidity followed by 12 hours exposure to 600 mg/L ethylene oxide at 52° F. and 25% relative humidity. The chamber was then aerated at 32° F. for at least 12 hours until ethylene oxide concentration was less than 0.25 ppm.

After sterilization, the paclitaxel content on the device or the paclitaxel content of the composition was assessed (through device extraction for coated medical devices i.e. immersion of the whole device in an extraction solvent) using UPLC quantification as described in the evaluation methods section. For each device or composition, the percentage drug recovery after sterilization was calculated by normalizing the extracted paclitaxel amount by the theoretical paclitaxel amount loaded on the device, or present in the composition pre-sterilization.

Test Method E—Stability to Electron Beam Sterilization

A further method to sterilize compositions of the invention includes electron beam sterilization. A sample of the composition is placed into a breathable polyethylene pouch (e.g. a Tyvek pouch) and irradiated at a dosage of 15 to 40 kGray under ambient conditions, using commercial sterilization providers, such as Sterigenics International, Inc. (Deerfield, Illinois). After e-beam sterilization, the paclitaxel content on the device is assessed as described for Test Method D.

Test Method F—Stability to Vapour Hydrogen Peroxide Sterilization

A further method to sterilize compositions of the invention includes vapour hydrogen peroxide sterilization. A sample of the composition is placed into a breathable polyethylene pouch (e.g. a Tyvek pouch) and exposed to vapour hydrogen peroxide using a commercially available sterilization chamber, such as the VHP-MD880 system (Steris Corp., Mentor, Ohio) following the manufacturer's recommended protocol. After vapour hydrogen peroxide sterilization, the paclitaxel content on the device is assessed as described for Test Method D.

Test Method G—Stability to Plasma Hydrogen Peroxide Sterilization

A further method to sterilize compositions of the invention includes plasma phase hydrogen peroxide sterilization. A sample of the composition is placed into a breathable polyethylene pouch (e.g. a Tyvek pouch) and exposed to plasma phase hydrogen peroxide using a commercially available sterilization chamber, such as the Sterrad 100NX system (Advanced Sterilization Products, Irvine, California) following the manufacturer's recommended protocol. After plasma phase hydrogen peroxide sterilization, the paclitaxel content on the device is assessed as described for Test Method D.

Example 1: Method for Preparation of Paclitaxel-Excipient Solid Composition Particulates A paclitaxel stock solution was prepared. Paclitaxel (110 mg/ml) was dissolved in dichloromethane. 300 µl of solution was aliquoted into 4 ml clear glass vials and the dichloromethane allowed to evaporate overnight, to produce a cast paclitaxel film.

1 g of excipient was placed into a 7 ml clear glass vial. 1 ml of either acetone (dry) or acetone:water (75:25 v/v) was added to the vial, as indicated in Table 1. The vial placed on a desktop shaker. Either additional excipient or additional solvent was added as needed to produce a solution saturated with the excipient. The saturated solution was filtered through a 0.2 um PTFE filter into a 4 ml glass vial.

400 µl of the filtered solution was added to the vial containing the cast paclitaxel film. The solution was stirred with a magnetic stir bar. The contents became cloudy or opaque, due to the formation of precipitate. The mixtures were filtered through a PTFE filter. The wet precipitate was collected from the filter membrane, and dried to produce the paclitaxel-excipient solid compositions.

Example 2: Thermal and Compositional Analysis of Paclitaxel-Excipient Solid Compositions of Example 1

The paclitaxel-excipient compositions of Example 1 were examined by DSC using the method described in General Procedures. Samples of each composition were added to a DSC pan and dried overnight. Samples of pure paclitaxel and pure excipient were also examined as controls.

Peak melting temperatures of each starting component and of the paclitaxel-excipient solid compositions are shown in Table 1. Thermograms of paclitaxel-PABA, paclitaxel-succinic acid and paclitaxel-adipic acid compositions are shown in FIGS. 1A to 1C.

The concentration of paclitaxel (wt %) in each paclitaxel-excipient composition was determined using UPLC as described in General Procedures. A sample of each composition was dissolved in the same solvent system from which precipitation occurred (Table 1) prior to analysis.

TABLE 1

Melting points and compositions paclitaxel-excipient solid compositions of Example 1

| # | Excipient | Solvent | $T_m$ Ex (° C.) | $T_m$ Px (° C.) | $T_m$ NF (° C.) | Ptx:ex (wt/wt) | Device[d] |
|---|---|---|---|---|---|---|---|
| | | Compositions of Example 1 | | | | | |
| 2-1 | PABA | 75/25 acetone/water | 189 | 217 | 140 | 62:38 | DEB |
| 2-2 | PABA | Acetone | 189 | >220 | 159 | 77:23 | SSG |
| 2-3 | saccharin | 75/25 acetone/water | >220 | 217 | 150 | 78:22 | DEB |
| 2-4 | saccharin | Acetone | >220 | >220 | 167 | 68:32 | ND |
| 2-5 | ascorbic acid | 75/25 acetone/water | 193 | 217 | 187 | 35:65 | DEB |
| 2-6 | methyl paraben | 75/25 acetone/water | 127 | 217 | 90 | 61:39 | DEB |
| 2-7 | caffeine | 75/25 acetone/water | 158[a] | 217 | 134 | 87:13 | DEB |
| 2-8 | calcium salicylate | 75/25 acetone/water | >220[b] | 217 | 165 | 77:23 | DEB |

TABLE 1-continued

Melting points and compositions paclitaxel-excipient solid compositions of Example 1

| # | Excipient | Solvent | $T_m$ Ex (° C.) | $T_m$ Px (° C.) | $T_m$ NF (° C.) | Ptx:ex (wt/wt) | Device[d] |
|---|---|---|---|---|---|---|---|
| | | Compositions of Example 1 | | | | | |
| 2-9 | pentetic acid | 75/25 acetone/water | >220 | 217 | 210 | 90:10 | ND |
| 2-10 | creatinine | 75/25 acetone/water | 220 | 217 | 171 | 86:14 | ND |
| 2-11 | ethylurea | 75/25 acetone/water | 95 | 217 | 92 | 45:55 | ND |
| 2-12 | acetaminophen | 7525 acetone/water | 170 | 217 | 160 | 41:59 | ND |
| 2-13 | aspirin | 75/25 acetone/water | 144 | 217 | 133 | 35:65 | ND |
| 2-14 | theobromine | 75/25 acetone/water | >220 | 217 | 206 | 84:16 | ND |
| 2-15 | tryptophan | 75/25 acetone/water | >220 | 217 | 206 | 74:26 | ND |
| 2-16 | succinic acid | Acetone | 189 | >220 | 169 | 84:16 | SSG |
| 2-17 | saccharin sodium | 75/25 acetone/water | >220[c] | 217 | 121 | 60:40 | ND |
| 2-18 | succinic acid | 75/25 acetone/water | 189 | 217 | 164 | 82:18 | DEB |
| 2-19 | glutaric acid | 75/25 acetone/water | 98 | 217 | 94 | 36:64 | DEB |
| 2-20 | adipic acid | 75/25 acetone/water | 152 | 217 | 149 | 51:49 | DEB |
| 2-21 | theophylline | 75/25 acetone/water | >220 | 217 | 207 | 80:20 | DEB |

$T_m$ Ex—peak max (determined by DSC) of pure excipient;
Tm Px—peak max (determined by DSC) of pure paclitaxel;
$T_m$ NF—peak max (determined by DSC) of novel form;
Ptx:ex (wt/wt)—ratio of paclitaxel:excipient (determined by measuring wt % of paclitaxel in coating using UPLC);
[a]sublimation observed;
[b]dehydrated at 176° C.;
[c]dehydrated at 129° C.;
[d]preferred device substrate utility
ND = not determined It can be seen that all of the compositions formed in Example 1 melted as a single phase with a depressed melting point. The preferred device substrate utility for each composition was assigned based on the adhesion test described in Example 4 and the in vitro tissue transfer test described in Example 5.

Example 3a—Construction of an ePTFE Covered Balloon for Use with the Coating of the Invention Expanded polytetrafluoroethylene (ePTFE) material was obtained with the following typical properties: thickness of 38.1 microns, width of 2.7 cm, mass/Area of 8.73 g/m², longitudinal (i.e., "machine direction") matrix tensile strength (MTS) of 283.5 MPa, transverse MTS of 11.0 MPa, longitudinal force to break of 0.112 kgf/mm, and IPA bubble point of 9.93 kPa.

A 1.7 mm×170 mm stainless steel mandrel was obtained and a length of the ePTFE material described above was cut to 160 mm. The ePTFE piece was wrapped longitudinally around the mandrel (i.e., "cigarette-wrapped") approximately five times, with the machine direction parallel to the length of the mandrel.

Another type of ePTFE material was obtained to serve as a manufacturing aid. This ePTFE had the following typical properties: thickness of 8.9 microns, width of 24 mm, mass/Area of 2.43 g/m², longitudinal MTS of 661.9 MPa, transverse MTS of 9.9 MPa, and IPA bubble point of 4.83 kPa.

This second ePTFE material was helically wrapped over the first ePTFE wrapped tube on a first bias at a 45 degree pitch with a 50% overlap from one end of the previously wrapped tube to the other and then on a reversed bias at a 45 degree pitch from end to end of the underlying wrapped ePTFE tube. This produced approximately 4 layers of overwrap.

The mandrel and ePTFE wraps were thermally treated for 3 minutes at 380° C. and allowed to cool to room temperature. The helical ePTFE overwrap was removed and discarded.

A nylon tube was obtained having an inside diameter of 2.16 mm and a 0.038 mm wall thickness. The first ePTFE material wrapped tube was trimmed to a length of 44 mm on the mandrel and removed from the mandrel. The inside diameter of the ePTFE tube was increased to fit over the nylon tube by using a tapered stainless steel mandrel. The ePTFE tube was then positioned co-radially over the nylon tube.

A 5 mm×40 mm long nylon balloon catheter with a 0.89 mm guidewire lumen was obtained (Bavaria Medizin Technologie, model #BMT-035, article #08GL-504A). A 0.89 mm stainless steel mandrel was inserted into the distal guidewire lumen of the balloon catheter to stiffen the area of the catheter proximate the balloon. The balloon was inflated to 2 atmospheres. The partially inflated balloon was manually dipped into a solution comprising Fluorinert FC-72 (3M, Saint Paul, MN) and a thermoplastic fluoroelastomer copolymer of tetrafluoroethylene/perfluoromethylvinylether (TFE/PMVE) as taught in U.S. Pat. Nos. 7,049,380 and 8,048,440 (Gore Enterprise Holdings, Inc., incorporated herein by reference).

The balloon was held in the solution for approximately 1 second, removed and gently tapped to remove excess of the solution. The coated balloon was allowed to dry for 15 seconds. This manual dip coating process was repeated 3 times to produce 3 coats over the balloon. The balloon was then deflated to approximately its original compacted diameter by pulling a vacuum on its catheter inflation port.

The nylon tube and ePTFE wrapped tube assembly as described above was fitted co-radially over the re-compacted and coated balloon and centered on the balloon catheter radiopaque marker bands. The ePTFE wrapped tube was held in place while the nylon tube was manually removed. The balloon was inflated to approximately 2-3 atmospheres for 30 seconds. This created an adhesive bond between the inner wall of the ePTFE wrapped tube and the TFE/PMVE coating on the nylon balloon. The balloon was then deflated to approximately its original compacted dimensions.

Example 3b: Method of Preparing a DEB with a Paclitaxel-Excipient Coating

Paclitaxel and excipient were co-dissolved in acetone:water (65-75 v % acetone) to form a coating solution, at concentrations listed in Table 2. Percutaneous transluminal angioplasty balloon catheters ("nylon balloons"—as described in "Materials") were coated with certain paclitaxel-excipient combinations as shown in Table 2. Additional balloons ("ePTFE covered balloons") were first modified by attachment of an ePTFE covering layer (as described in Example 3a) and then coated with certain paclitaxel-excipient combinations as shown in Table 2.

TABLE 2

Coating solution composition

| Solution/ Coating No. | Excipient | Excipient (wt %) | Paclitaxel (wt %) | % Paclitaxel* (wt %) | Total solids (g/ml) |
|---|---|---|---|---|---|
| 3-1 | PABA | 0.26-0.64 | 2.30-2.51 | 80-90 | 0.022-0.027 |
| 3-2 | PABA | 2.53 | 2.51 | 50 | 0.045 |
| 3-3 | Methyl paraben | 0.98-0.99 | 2.29 | 70 | 0.029 |
| 3-4 | Ca salicylate | 0.71-0.80 | 2.30-2.39 | 75-76 | 0.026-0.027 |
| 3-5 | Caffeine | 0.70-0.77 | 2.30 | 75-77 | 0.026-0.027 |
| 3-6 | Succinic acid | 0.32-0.60 | 1.98-2.30 | 79-86 | 0.020-0.025 |
| 3-7 | Ascorbic acid | 2.75 | 2.25 | 45 | 0.046 |

*% of paclitaxel (wt %) in solid components of coating solution

The working regions of the nylon balloon and the ePTFE covered balloons were inflated to full diameter and coated by pipetting the coating solution (90-100 ul of solution for 5×40 mm balloons and 420 ul for 7×120 mm balloons) under rotation. As the solvent from the coating solution evaporated, the balloon was deflated and refolded to its un-inflated diameter. Coated balloons were dried overnight at room temperature in their folded state. The final drug loading on all devices was approximately 3 µg/mm² balloon surface area (estimated by pipetting a known solution volume with a known paclitaxel concentration). Coated balloons were packaged and sterilized by ethylene oxide exposure.

Example 4: Adhesion Test

Coated balloons prepared according to a method of Example 3b were examined for the adhesion of the paclitaxel-excipient solid compositions to the balloon pre-dilation, using Test Method C, as described in General Procedures.

Figure 2:
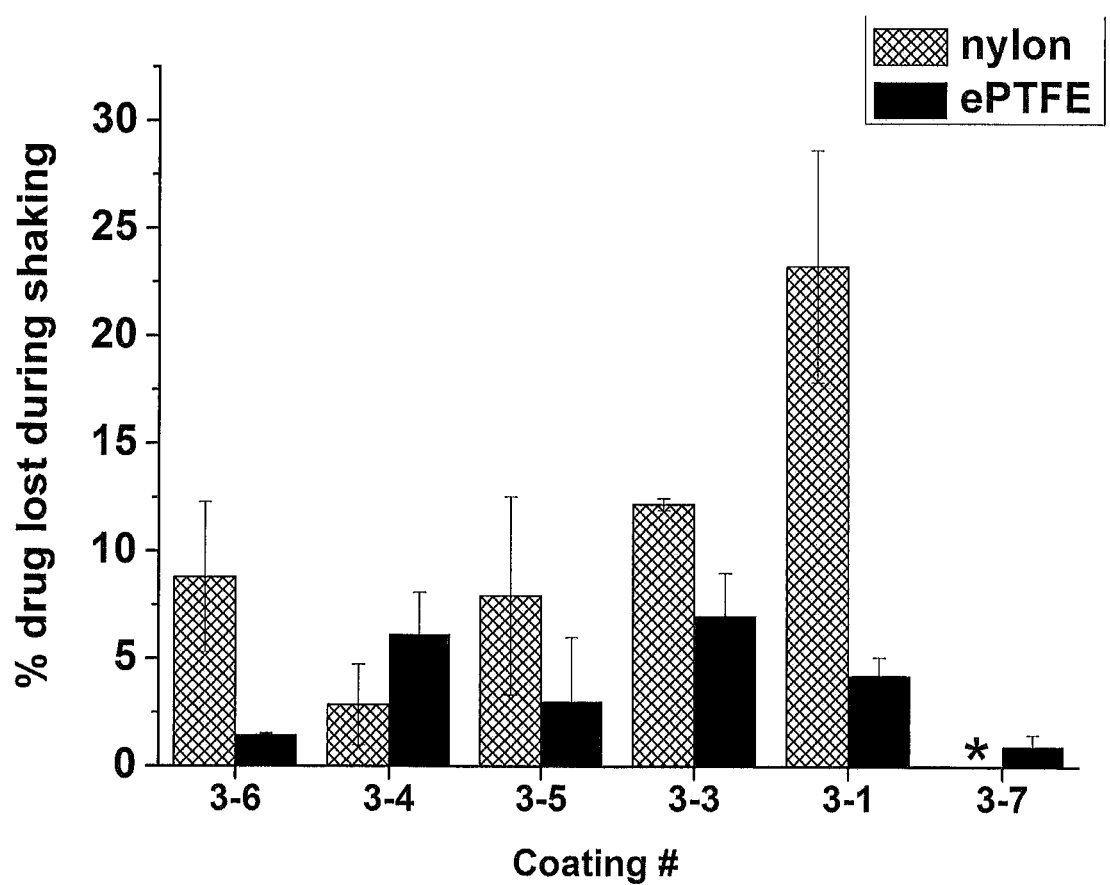
FIG. 2 shows the results of an adhesion test (Example 4) carried out on coatings prepared according to Example 3b.
Figure 3:
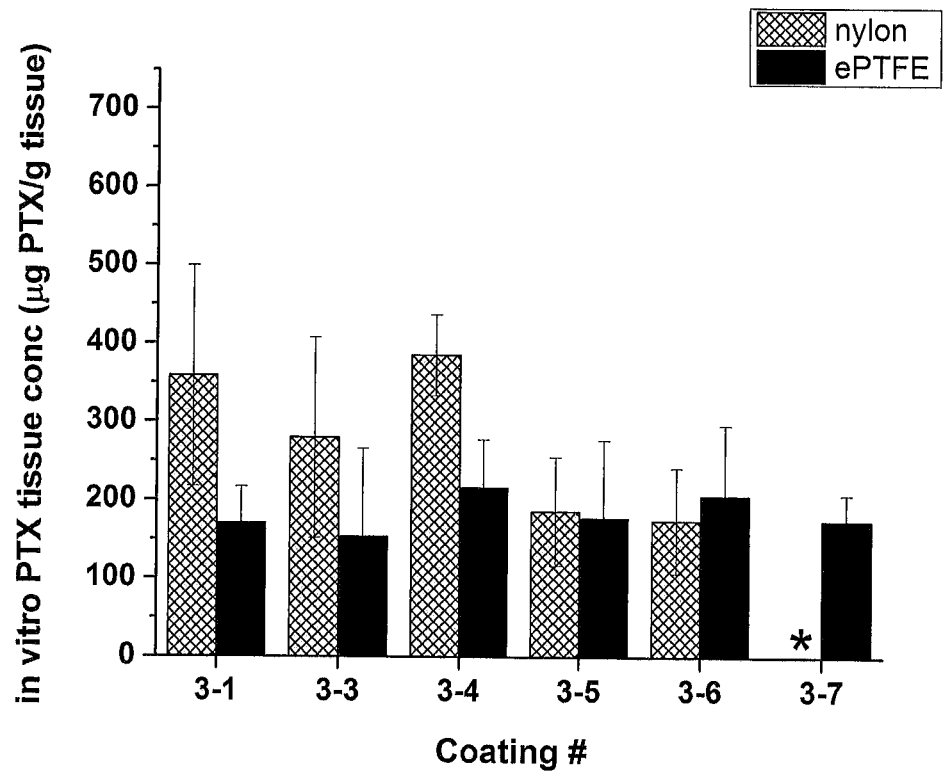
FIG. 3 shows the results of an in vitro tissue test (Example 5) carried out on coatings prepared according to Example 3b.

The results of the test are summarized in FIG. 2. The asterisk in FIG. 2 indicates that there was no testing of the coating on a nylon substrate. It should be noted a paclitaxel-only coated balloon was prepared (for use as a control) but was not included in the adhesion testing due to a high degree of drug being lost with little balloon manipulation (quantified visually). The excipient had an effect on the strength of adhesion, as exemplified by the extent of paclitaxel particulation and transfer to the test tube. Coatings on ePTFE generally showed greater adhesion than the same coating on nylon.

Example 5: In Vitro Tissue Transfer and Uptake Test

Coated balloons prepared according to a method of Example 3b were examined for their ability to transfer paclitaxel from the balloon surface to a vascular tissue using Test Method A, as described in General Procedures. The vessel was analyzed for paclitaxel content using LC/MS-MS according to General Procedures and the results are summarized in FIG. 3. The asterisk in FIG. 3 indicates that there was no testing of the coating on a nylon substrate. Approximately 120-240 µg paclitaxel per gram tissue was transferred from the balloon surface to the porcine vascular tissue.

Example 6: In Vivo Uptake Test

Samples of coated balloons prepared according to a method of Example 3b were deployed in a porcine model in an in vivo test employing the peripheral arteries in an adult swine. Angiography of the peripheral artery determined balloon inflation pressure required for appropriate vessel over-sizing. The balloon was tracked to the target site, inflated to the required inflation pressure for 60 seconds, deflated and removed. Post-deployment, the spent device was submitted for UPLC analysis of remaining paclitaxel content as described in General Procedures.

Animals were euthanized after 7 days or after 28 days. The treated arteries were harvested. An untreated carotid artery was also harvested to assess potential systemic drug delivery to a remote site. Adipose tissue was removed from each artery, radial cross-sections (100±50 mg) were cut from each artery, and the arteries analyzed for paclitaxel content using UPLC/tandem mass spectrometry. For the treated artery, mean paclitaxel levels were calculated by averaging paclitaxel levels in all radial cross-sections in the indicated segment.

Figure 4:
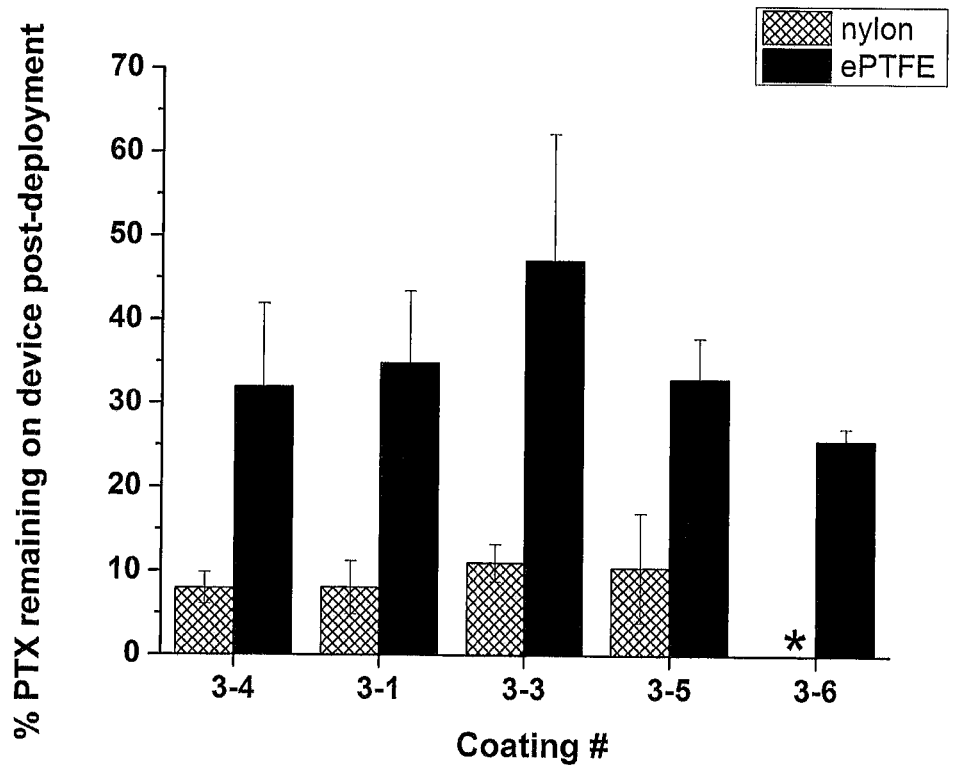
FIG. 4 shows the % paclitaxel remaining on a coated balloon prepared according to Example 3b after in vivo deployment (Example 6)

The tissue samples were homogenized and extracted with 0.2% acetic acid in methanol, containing 2 mg/ml deuterated paclitaxel as an internal standard. The samples were centrifuged to remove all particulates and the supernatant was used for the analysis. The retention and separation of paclitaxel was achieved essentially as per Example 3b (and General Procedures), using a phenyl column with a sodium acetate/acetic acid mobile phase in acetonitrile:water. The detection and quantification of paclitaxel was achieved by tandem mass spectrometry using the sodium adduct of paclitaxel, as described in General Procedures. FIG. 4 shows the percent paclitaxel (mean±s.d.) remaining on the balloon after in vivo deployment and inflation. The asterisk in FIG. 4 indicates that there was no testing of the coating on a nylon substrate. All samples had less than 50% of their initial paclitaxel remaining on the balloon, indicating significant transfer of paclitaxel from the balloon surface to the porcine tissue.

Figure 5:
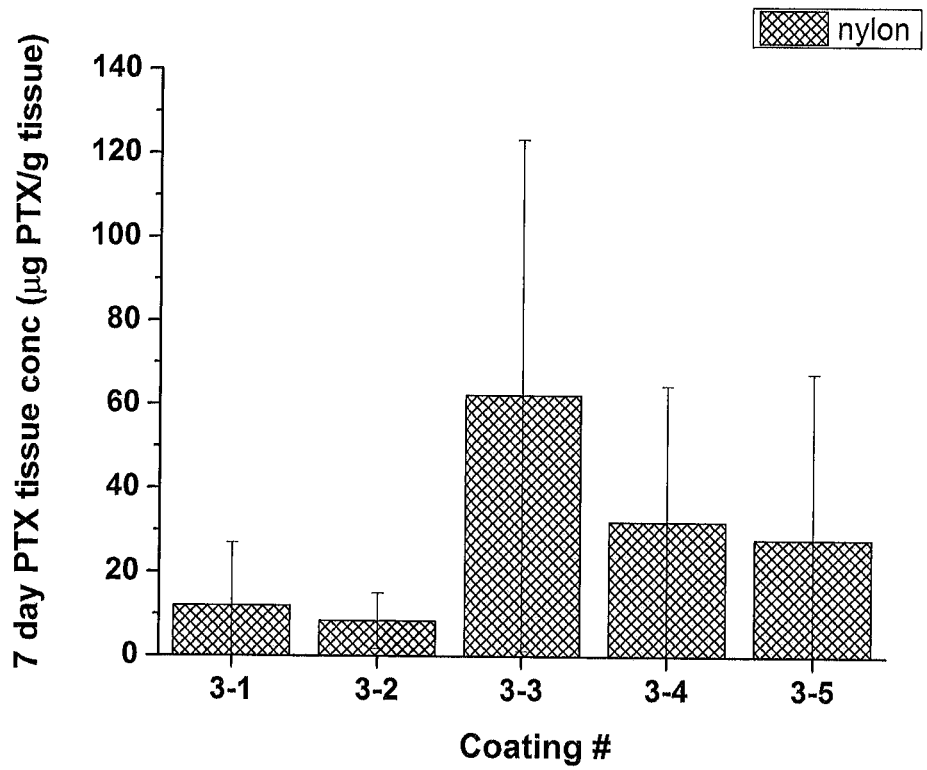
FIG. 5 shows paclitaxel levels in porcine arterial tissue 7 days after in vivo deployment of a coated balloon prepared according to Example 3b (Example 6)
Figure 6:
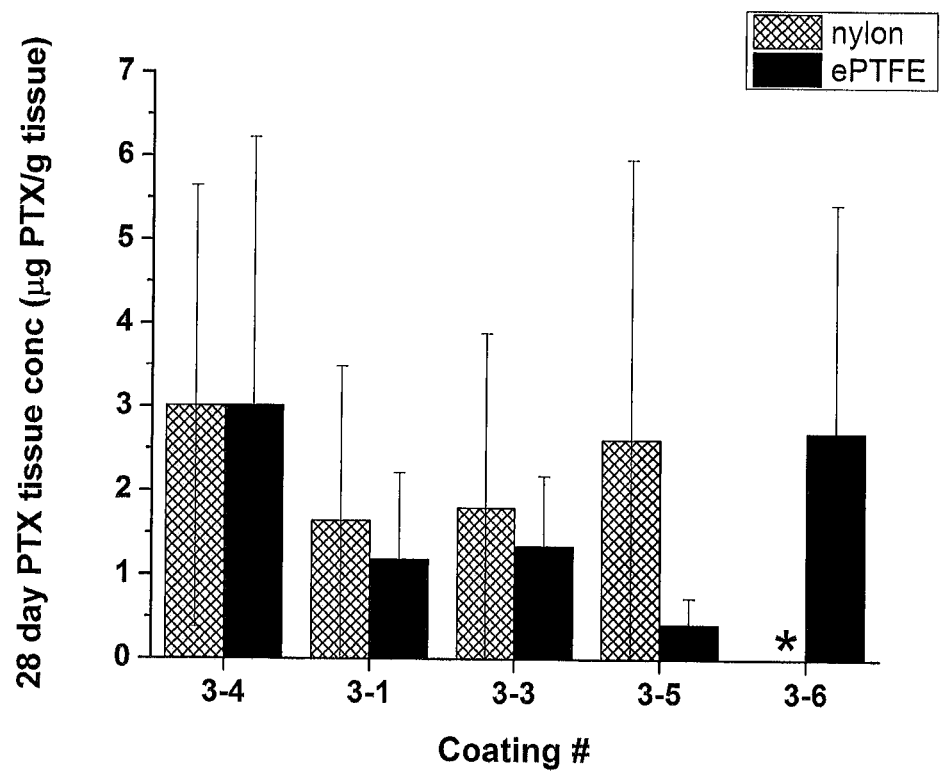
FIG. 6 shows paclitaxel levels in porcine arterial tissue 28 days after in vivo deployment of a coated balloon prepared according to Example 3b (Example 6)

FIGS. 5 and 6 show respectively the 7 and 28 day paclitaxel levels in porcine arterial tissue in treated arterial tissue segments (see also Table 3 below for 28 day results). The asterisk in FIG. 6 indicates that there was no testing of the coating on a nylon substrate. Paclitaxel levels in untreated vascular tissues were several orders of magnitude lower, on the order of 3 to 6 ng paclitaxel per gram of tissue, demonstrating that the delivery of paclitaxel from the balloon was localized to the target tissue, and was retained at the target tissue for up to 28 days.

TABLE 3

Paclitaxel tissue levels at 28 days in vivo porcine model.

| # | Excipient | Substrate | Mass released (mg)[1] | 28 day tissue concentration μg PTX/g tissue | 28 day localized drug delivery efficiency (%)[2] |
|---|---|---|---|---|---|
| 3-6 | Succinic acid | ePTFE | 1.51 ± 0.02 | 5.6 ± 0.4 | 0.09 ± 0.02 |
| 3-5 | Caffeine | Nylon | 1.79 ± 0.13 | 2.6 ± 3.4 | 0.03 ± 0.03 |
|  |  | ePTFE | 1.34 ± 0.10 | 0.4 ± 0.3 | 0.005 ± 0.004 |
| 3-4 | Calcium salicylate | Nylon | 1.84 ± 0.04 | 3.0 ± 2.6 | 0.03 ± 0.02 |
|  |  | ePTFE | 1.36 ± 0.20 | 3.0 ± 3.2 | 0.03 ± 0.03 |
| 3-3 | Methylparaben | Nylon | 1.78 ± 0.04 | 1.8 ± 2.1 | 0.02 ± 0.03 |
|  |  | ePTFE | 1.06 ± 0.30 | 1.3 ± 0.8 | 0.03 ± 0.03 |
| 3-1 | PABA | Nylon | 1.84 ± 0.06 | 1.6 ± 1.8 | 0.02 ± 0.01 |
|  |  | ePTFE | 1.30 ± 0.17 | 1.2 ± 1.0 | 0.01 ± 0.01 |

[1]mg originally on balloon - mg left on balloon following procedure
[2]calculated as (total mg in tissue/mass released) * 100

Example 7: Vascular Stent Coated with Pre-Coated with a Heparin-Bonded Surface Vascular stents were pre-coated to form a heparin-bonded surface before being over-coated with a paclitaxel-excipient solid composition of the invention. Vascular stents (5 mm by 30 mm), featuring a dual component design, constructed from a single wire nitinol stent interconnected by a durable, biocompatible, expanded polytetrafluoroethylene (ePTFE) structure, were made according to US2009/0182413A1 (Gore Enterprise Holdings, Inc., incorporated herein by reference in its entirety). The durable, biocompatible, expanded ePTFE structure was coated with a heparin-bonded surface according to U.S. Pat. No. 6,461,665 (Carmeda AB, which is incorporated herein by reference in its entirety).

The aforementioned heparin coated vascular stents were over-coated with an embodiment of the paclitaxel-excipient solid composition comprising paclitaxel and caffeine. Paclitaxel and caffeine at a weight ratio of 75:25 were dissolved in 90/10 (v/v) acetone/water to obtain a 20 mg/ml paclitaxel solution.

The aforementioned heparin coated vascular stents were tied to a thread at one end for handling during the coating process. They were dipped into the paclitaxel solution, removed, and air dried; the coating procedure was repeated 10 to 30 additional times to produce three coated stents. At the end of the coating procedure each coated stent was weighed (stent device 1 had a coating weight of 0.588 mg, stent 2 had a coating weight of 0.642 mg and stent 3 had a coating weight of 1.2 mg) before being examined using DSC. A stent was compacted into a high mass DSC pan and sealed with an o-ring and lid (TA Instruments, part #900825.902) and analyzed using the DSC method described in General Procedures (except that the sample was not dwelled at 100° C.); an uncoated vascular stent was analyzed as a reference. A single depressed melting endotherm at 132° C. was observed for the paclitaxel-caffeine solid composition. This melting temperature is consistent with the paclitaxel-caffeine solid compositions as prepared by Example 1.

Example 8: Compaction and Deployment of Vascular Stent Coated with Paclitaxel-Excipient Solid Composition The coated stents of Example 7 underwent compaction and deployment to examine durability and robustness of the coating.

The coated stents of Example 7 were compacted diametrically to an outer diameter of 3.36 mm using means known to those of skill in the art of self-expanding stents. The stents were constrained in the compacted state within a constraint tube with an inner diameter of 3.36 mm. Stents were deployed from the containment tube with the use of a push rod. After deployment, the stent was weighed and compared to its weight before compaction.

TABLE 4

Summary of Coating Durability

| Stent Device | Coating Weight (mg) | Coating Lost (mg) | % of coating lost |
|---|---|---|---|
| 1 | 0.588 | 0.085 | 14.5 |
| 2 | 0.642 | 0.038 | 5.9 |
| 3 | 1.2 | 0.107 | 8.9 |

The average drug coating mass loss was 9.7% and this was determined to represent a high degree of durability. This durability not only considers the compaction and expansion of the coated stent, but also considers the stent being pushed out from the containment tube, wherein the stent sheared against the containment tube inner surface.

Example 9: Heparin Activity of Vascular Stent Coated with Paclitaxel-Excipient Solid Composition Heparin activity of the underlying heparin bonded surface of the compacted and deployed stents of Example 8 was measured according to WO2009/064372, which is incorporated herein by reference by its entirety. The paclitaxel-caffeine solid composition coating was first extracted from the vascular stent surface by immersion in a glass vial containing 0.2% acetic acid in methanol, with shaking at 300 rpm for 1 hr at 40° C. The washed stents demonstrated therapeutically useful heparin activities of greater than 1 pmol/cm$^2$.

These results attest to the surprising activity of the heparin-bonded surface under the conditions of coating with a paclitaxel-excipient solid composition, mechanical stress including compaction and expansion, and mechanical shear including deployment.

Example 10: Heparin Activity of Vascular Stent Coated with Paclitaxel-Excipient Solid Composition Post Sterilization Stents coated as in Example 7 are sterilized by ethylene oxide. The stents can subsequently undergo compaction and deployment to examine durability and robustness of the coating along with retention of heparin activity.

Example 11: Acute Tissue Transfer of Vascular Stent Coated with Paclitaxel-Excipient Solid Compositions and Heparin Activity Stent Device number 3 of Example 8 was examined for its ability to transfer paclitaxel from the stent surface to a vascular tissue in an in vitro model as described in Test Method B. The stent was removed, and vessel was analyzed for paclitaxel content using LC/MS-MS according to General Procedures. Approximately 16 μg paclitaxel per gram tissue was transferred from the stent surface to the porcine vascular tissue.

These paclitaxel tissue levels were within the reported therapeutic range of paclitaxel-coated vascular stents of 20 ug paclitaxel per gram tissue at 24 hrs, as described in the literature (M. D. Dake et al., J Vasc Interven Rad, 22(5): 603-610, 2011, "Polymer-free Paclitaxel-coated Zilver PTX Stents—Evaluation of Pharmacokinetics and Comparative Safety in Porcine Arteries")

Heparin activity of the stent after it was removed from the vessel was measured according to Example 9, and was determined to be a therapeutically useful heparin activity of greater than 1 pmole/cm$^2$.

Thus, when a heparin coated vascular stent over-coated with a paclitaxel-excipient coating of the invention was contacted with vascular tissue a therapeutic amount of paclitaxel was transferred from the coating to the vascular tissue and a therapeutically useful heparin activity was retained for the heparin-bonded surface. Thus, a coated stent of the invention has the potential to exhibit dual therapeutic activity, when a first coating comprising a therapeutic agent is applied to the stent, followed by an over coat of the paclitaxel-excipient composition of the invention.

Example 12a: Ethylene Oxide Stability of Coated DEB Prepared Substantially According to the Method of Example 3b Two ePTFE balloons coated according to Example 3b were sterilized and their paclitaxel content analyzed post-sterilization, in accordance with Test Method D. The paclitaxel percentage recovery is shown in Table 5 below.

TABLE 5

Paclitaxel % recovery post-ethylene oxide sterilization

| N# | Excipient | % Recovery (normalized to theoretical) avg ± st dev |
|---|---|---|
| 3-5 | Caffeine | 97.2 ± 1.4 |
| 3-6 | Succinic acid | 82.9 ± 1.5 |

Post-sterilization both samples showed greater than 80% paclitaxel recovery, indicating that these devices have adequate paclitaxel stability following ethylene oxide sterilization.

Example 12b—Ethylene Oxide Stability of Paclitaxel-Excipient Films Prepared According to Example 1

Approximately 30 mg of excipient was weighed into a 7 mL glass vial and 6 mL of 75/25 v/v acetone/water was added. A small stirrer bar was added to each vial and all samples were stirred overnight at room temperature to ensure full dissolution. Next, a stock solution of paclitaxel in the casting solvent was made at 5 mg/mL. A specific volume of paclitaxel stock and excipient stock was added to a new vial to achieve the target paclitaxel/excipient weight fraction listed in Table 6. The vials were then mixed and aliquoted to N=6 of the 20 mL vials (0.5 mL each). A paclitaxel-only control was also added to N=6 vials (0.25 mL each). All vials were left in a fume hood overnight to evaporate the solvents. After drying, the samples were capped with cellulose membranes cut to septa size to allow ethylene oxide and moisture permeability. All samples were packaged in breathable polyethylene pouches. N=3 of each paclitaxel/excipient mixture were kept as non-sterilized controls, and the remainder (N=3) were sent for ethylene oxide sterilization (see Test Method D). Non-sterilized controls were stored at room temperature prior to analysis. Paclitaxel content analysis was performed as described in the Evaluation Methods section. Percent paclitaxel recovery was calculated by normalizing to either theoretical initial loading or pre-sterilized samples.

TABLE 6

Paclitaxel % Recovery on cast formulations pre- and post- sterilization (Mean value of N = 3 shown)

| Excipient | Ptx:ex (wt/wt) | % PTX recovery, theoretical vs. pre | % PTX recovery, pre vs. post |
|---|---|---|---|
| Ca salicylate | 75/25 | 99.0 | 99.3 |
| caffeine | 75/25 | 98.5 | 99.1 |
| p-aminobenzoic acid | 80/20 | 97.6 | 100.2 |
| methylparaben | 70/30 | 100.5 | 98.7 |
| succinic acid | 80/20 | 97.2 | 100.5 |
| ascorbic acid | 45/55 | 98.4 | 99.8 |
| saccharin | 80/20 | 99.4 | 99.2 |
| acetaminophen | 40/60 | 97.9 | 99.5 |
| theophylline | 80/20 | 99.0 | 99.7 |
| aspirin | 35/65 | 99.0 | 88.5 |
| glutaric acid | 40/60 | 92.2 | 98.5 |
| adipic acid | 50/50 | 93.4 | 98.0 |
| PTX only | 100/0 | 98.2 | 101.7 |

Pre-sterilization, all samples showed greater than 90% paclitaxel recovery. Post-sterilization, all samples showed greater than 80% paclitaxel recovery. Altogether, these results indicate that the formulations have adequate paclitaxel stability to ethylene oxide sterilization.

Example 12c: Ethylene Oxide Sterilization Instability of Paclitaxel-Niacinamide Formulations Paclitaxel/niacinamide coated balloons are reported in Example 22 of patent application US2012/0310210 A1 (Campbell et al., herein incorporated by referenced in its entirety). When these same balloon samples were subjected to ethylene oxide sterilization, paclitaxel quantification via UPLC showed nearly complete paclitaxel degradation (paclitaxel recovery after sterilization was 4%, normalized to unsterilized samples).

Example 13: DSC Analysis of DEB Coated with a Paclitaxel-Excipient Coating 30 mL of 75/25 (v/v) acetone/water was added to a scintillation vial. 600 mg of paclitaxel was weighed and added to the vial to achieve approximately 20 mg/mL paclitaxel concentration. In a separate vial, 10 mL of 99/1 (v/v) acetone/water was added along with 200 mg of paclitaxel (to also arrive at 20 mg/mL). The vials were stirred using a stir bar to dissolve the paclitaxel.

Next, using a microbalance, excipients were weighed into 4 or 7 mL glass scintillation vials (see Table 7 below). One of the two paclitaxel stock solutions was added to each vial as noted in Table 7. The volume of stock paclitaxel solution to be added was adjusted based on excipient mass so that the target paclitaxel/excipient ratio was achieved. Each formulation was stirred using a stir bar until the excipient dissolved, which took several minutes for all formulations except 13-2, which failed to dissolve even after approximately 30 minutes of stirring. As a result formulation 13-2 was not evaluated further.

Nylon balloons of 7 mm×120 mm dimension were coated in the same manner as described in Example 3B. 420 µl of coating was added to each balloon surface (volume scaled by surface area so that same coating density as Example 3B). Also coated were ePTFE films supported by embroidery hoops. The ePTFE film was of the type described first in Example 3A and used in that example to cover a nylon balloon. 100 µl of formulation 13-1 and 13-7 was added to separate locations on the ePTFE film (100 µl to each location) and spread around to cover a surface area of approximately 22 mm diameter.

After drying, the balloons were mechanically agitated to remove the coatings from the nylon surface (using a stainless steel spatula to scrape the coating and/or rubbing the balloon surface against wax weighing paper). The generated particulate was then added to a pre-weighed DSC pan. The pan was then weighed again and DSC analysis was performed as described in General Procedures.

Similarly, the coated region of the ePTFE film was cut out using a scissors and compacted into a pre-weighed DSC pan which was then weighed again. An uncoated region of the ePTFE (similar size) was also cut out and added to a pre-weighed DSC pan which was then weighed again. The uncoated PTFE sample mass was subtracted from the coated ePTFE sample masses to provide an approximation for mass of coating in the DSC pans. DSC analysis was performed on all samples as in General Procedures. The peak max endotherm was calculated in the same fashion as Table 1.

Coatings 13-1, 13-4, 13-5, 13-6, 13-7 and 13-8 were formulated with the same or very similar paclitaxel/excipient weight ratios as for compositions prepared according to Example 1 (weight ratios are shown in Table 1). All six coatings showed a single depressed endotherm at around the same temperature as the corresponding composition, as can be seen by comparing the final two columns of Table 7. It can therefore be concluded the precipitation method described in Example 1 and the solvent evaporation method of Example 3b and the present Example produce substantially similar materials.

Figure 7:
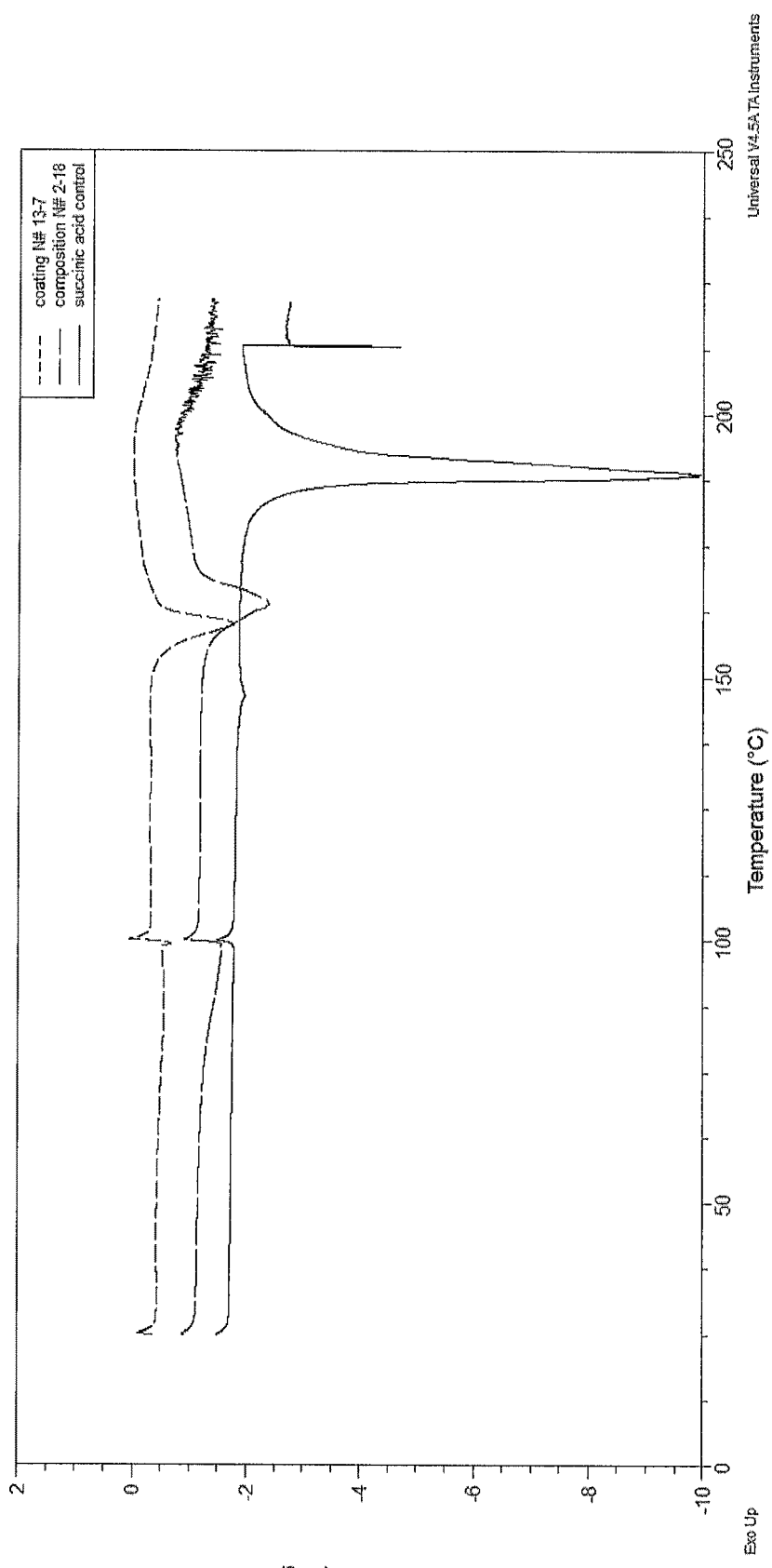
FIG. 7 shows a DSC thermogram of a paclitaxel-succinic acid coated balloon prepared according to Example 13 (paclitaxel:succinic acid=82:18 wt/wt) and compared to the paclitaxel-succinic acid composition shown in FIG. 1B.

FIG. 7 shows an overlay of three DSC thermograms. The lower plot is a thermogram of pure succinic acid as a control, the middle plot is a thermogram of a paclitaxel-succinic acid composition prepared according to Example 1 (composition 2-18), and the upper plot is a thermogram of the corresponding paclitaxel-succinic acid coating formed in the present example (coating 13-7). For the middle and upper plots (composition 2-18 and coating, 13-7, respectively) a depressed melting point is observed (at around the same temperature in each case) with no endotherm corresponding to pure succinic acid.

Coatings corresponding to coatings 13-1 and 13-7 were prepared for nylon balloons and were found to exhibit similar depressed melting endotherms (137-139° C. for caffeine and 161° C. for succinic acid).

TABLE 7

Formulations coated on balloons and ePTFE substrates and DSC analysis

| N# | Excipient (ex) | Mass ex (g) | Ptx:ex (wt/wt) | Solution 1 (mL) | Solution 2 (mL) | $T_m$ coating (° C.) | $T_m$ NF (° C.) (Table 1) |
|---|---|---|---|---|---|---|---|
| 13-1 | caffeine | 0.0149 | 87:13 | 4.979 | 0 | 135 | 134 (3-6) |
| 13-2 | caffeine | 0.1344 | 13:87 | 1.004 | 0 | ND | — |
| 13-3 | caffeine | 0.0171 | 87:13 |  | 5.722 | None | — |
| 13-4 | PABA | 0.0254 | 62:38 | 2.075 | 0 | 139 | 140 (3-1) |
| 13-5 | calcium salicylate | 0.0151 | 77:23 | 2.528 | 0 | 165 | 165 (3-8) |
| 13-6 | Methyl paraben | 0.0263 | 61:39 | 2.054 | 0 | 110 | 90 (3-6) |
| 13-7 | succinic acid | 0.0170 | 82:18 | 3.875 | 0 | 160 | 164 (3-18) |
| 13-8 | succinic acid | 0.0172 | 82:18 | 0 | 3.911 | 159 | 169 (3-16) |
| 13-9 | succinic acid | 0.0934 | 18:82 | 1.025 | 0 | 160, 185 | — |

N# = coating number
Ptx:ex = ratio of paclitaxel to excipient
$T_m$—peak max (determined by DSC) of the coating of Example 13
$T_m$ NF—peak max (determined by DSC) of corresponding compositions formed in Examples 1 and 2 (composition no. in parenthesis);
Solution 1 = 20 mg/mL paclitaxel in 75/25 (v/v) acetone/water
Solution 2 = 20 mg/mL paclitaxel in 99/1 (v/v) acetone/water Coating 13-9 has the reciprocal paclitaxel/excipient weight ratio of composition 2-18 in Table 1, i.e. 18:82 instead of 82:18 paclitaxel/succinic acid. A DSC analysis of coating 13-9 is shown in FIG. 8, which shows two melting endotherms (unlike compositions 13-7 and 13-8 in which a single depressed melting point was observed). A melting endotherm at 160° C. corresponded to a depressed melting endotherm while a melting endotherm at 185° C. was very close to the melting point of pure succinic acid (189° C.). Note that when increasing organic solvent content in the coating solution, the endotherm signal intensity was greatly diminished (formulation 13-7>13-8, and formulation 13-3 had no discernible endotherm).

The proportion of succinic acid which melted at 185° C. (i.e. the temperature close to the melting point of succinic acid in pure form) was determined using the enthalpy of fusion value. It was found that of the succinic acid present in the composition as a whole (82% of the total coating mass), 70% corresponded to pure crystalline succinic acid (i.e, the remaining 30% of succinic acid in the coating would be assumed to be present in the crystalline depressed endotherm form or in amorphous form). This was calculated as follows:

% succinic acid in original crystalline form=(balloon coating enthalpy of fusion circa 185° C./control succinic acid enthalpy of fusion circa 185° C.)*100, where the balloon coating sample mass entered into the DSC software=weighed sample mass added to DSC pan*mass fraction succinic acid in coating (i.e. 0.82).

Example 14: A Ternary Formulation Exhibiting a Singular Depressed Melting Point

A ternary formulation was created by combining succinic acid, caffeine, and paclitaxel. Each component was added to 3 mL of 75/25 v/v acetone/water and stirred until dissolved. The entire solution was then cast into a disposable aluminum pan and allowed to dry. The subsequent dried formulation was added to a DSC pan with a pinhole lid. DSC analysis was performed in the same manner as described in General Procedures, with the exception that the samples were not dwelled at 100° C.

TABLE 8

Composition and peak max of a ternary formulation

| No. | Excipient 1 & 2 | Excipient (wt % each) | Paclitaxel (wt %) | % Paclitaxel* (wt %) | Total solids (g/ml) | $T_m$ NF (° C.) |
|---|---|---|---|---|---|---|
| 14-1 | Succinic acid, caffeine | 0.3 | 2.3 | 79 | 0.023 | 111 |

Figure 9:
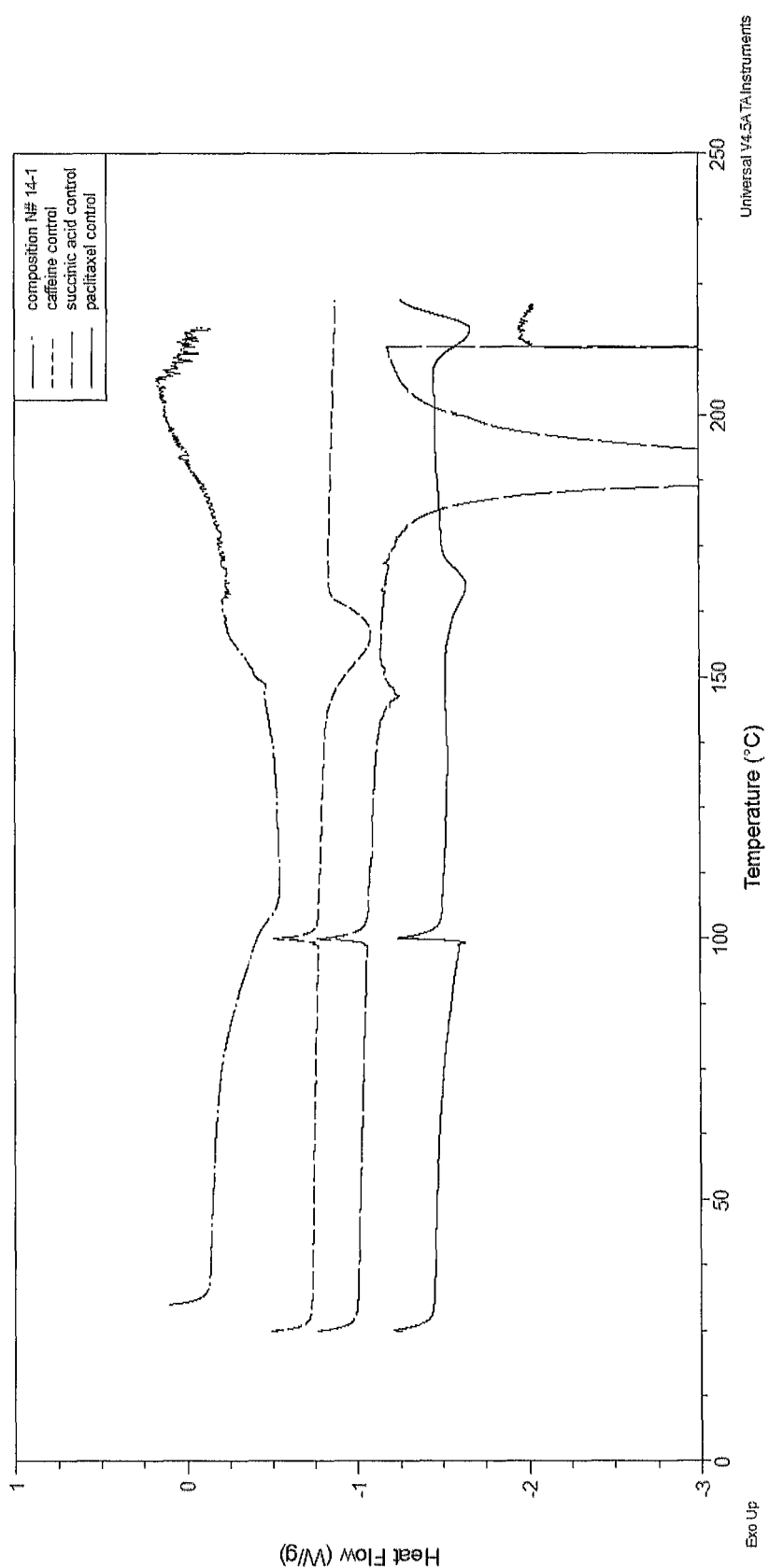
FIG. 9 shows a DSC thermogram of a ternary composition of the invention containing paclitaxel, succinic acid and caffeine (Example 14).

*% of paclitaxel (wt %) in solid components of coating solution
$T_m$ NF—peak max (determined by DSC) of novel form;

As shown in FIG. 9, ternary composition 14-1 exhibited a single endotherm (circa 100-150° C.) which was depressed compared to the individual starting components (see Table 1 for individual Tm's).

All references referred to in this application, including patent and patent applications, are incorporated herein by reference to the fullest extent possible.

Throughout the specification and the claims which follow, unless the context requires otherwise, the word 'comprise', and variations such as 'comprises' and 'comprising', will be understood to imply the inclusion of a stated integer, step, group of integers or group of steps but not to the exclusion of any other integer, step, group of integers or group of steps.

The invention claimed is:

1. A medical device for delivering a therapeutic agent to a tissue, the device having a solid surfactant-free particulate coating layer applied to a surface of the device, the coating layer comprising a therapeutic agent and at least one non-polymeric organic additive which is hydrolytically stable, independently selected from the group consisting of p-aminobenzoic acid, methyl paraben, caffeine, and calcium salicylate;
wherein:
when the least one non-polymeric organic additive is p-aminobenzoic acid, the weight ratio of paclitaxel to p-aminobenzoic acid is from 3:7 to 9:1,
when the least one non-polymeric organic additive is methyl paraben, the weight ratio of paclitaxel to methyl paraben is from 4:5 to 9:1,
when the least one non-polymeric organic additive is caffeine, the weight ratio of paclitaxel to caffeine is from 7:3 to 95:5,
when the least one non-polymeric organic additive is calcium salicylate, the weight ratio of paclitaxel to calcium salicylate is from 7:3 to 9:1,
wherein at least a proportion of the particulate coating layer comprising the therapeutic agent and the at least one non-polymeric organic additive melts as a single phase at a lower temperature than the melting point of the therapeutic agent and the at least one non-polymeric organic additive when in pure form;
wherein the therapeutic agent is paclitaxel; and
wherein the therapeutic agent, when formulated in the coating layer, is stable to ethylene oxide sterilization;
wherein the coating layer comprises crystalline particles of the therapeutic agent and the at least one non-polymeric organic additive in co-crystalline form.

2. A medical device for delivering a therapeutic agent to a tissue, the device having a solid surfactant-free particulate coating layer applied to a surface of the device, the coating layer comprising a therapeutic agent and at least one organic additive which is hydrolytically stable selected from the group consisting of p-aminobenzoic acid, saccharin, methyl paraben, caffeine, calcium salicylate, acetaminophen, aspirin, adipic acid and theophylline, wherein at least a proportion of the particulate coating layer comprising the therapeutic agent and the at least one organic additive melts as a single phase at a lower temperature than the melting point of the therapeutic agent and the at least one organic additive when in pure form;
wherein the therapeutic agent is paclitaxel;
wherein the therapeutic agent, when formulated in the coating layer, is stable to ethylene oxide sterilization;
wherein the coating layer comprises crystalline particles of the therapeutic agent and a non-polymeric organic additive in a co-crystalline form, wherein the non-polymeric organic additive in the co-crystalline form is selected from the list consisting of p-aminobenzoic acid, methyl paraben, caffeine and calcium salicylate.

3. A medical device according to claim 2, wherein the particulate coating layer is formed by evaporation of a solution of the therapeutic agent and the at least one organic additive applied to the device to form a solid particulate composition.

4. A medical device according to claim 2, wherein the particulate coating layer is formed by combining the therapeutic agent and at least one organic additive in powder form, and then applying the powder to the device, with an optional subsequent step of thermal treatment, to form a solid particulate composition.

5. A medical device according to claim 3 wherein the solution of the therapeutic agent and the at least one organic additive is a solution in a solvent selected from water, acetone and mixtures thereof.

6. A medical device according to claim 2, wherein the therapeutic agent and the at least one organic additive in the particulate coating are in crystalline form.

7. A medical device according to claim 2, wherein at least one organic additive melts at a temperature of greater than about 80° C. when in pure form.

8. A medical device according to claim 2, wherein at least one organic additive is a substance having a value for the dispersion component of the Hansen solubility parameter determined at 25° C. substantially the same as that of the therapeutic agent.

9. A medical device according to claim 8 wherein the dispersion component of the Hansen solubility parameter determined at 25° C. of the or each at least one organic additive is between 16 and 21 MPa0.5.

10. A medical device according to claim 2, wherein the coating layer comprises crystalline particles of the therapeutic agent and the at least one organic additive in a eutectic mixture.

11. A medical device according to claim 2, wherein the coating layer comprises crystalline particles of the therapeutic agent and the at least one organic additive in co-crystalline form.

12. A medical device according to claim 2, wherein substantially all of said particulate coating layer comprising the therapeutic agent and the at least one non-polymeric organic additive melts as a single phase at a lower temperature than the melting point of the therapeutic and the at least one organic additive when in pure form.

13. A medical device according to claim 2, wherein a proportion of the particulate coating layer comprising the therapeutic agent and the at least one organic additive melts at a temperature at or close to the melting point of at least one of the at least one of the organic additives in pure form.

14. A medical device according to claim 13, wherein the proportion of the at least one organic additive which melts at a temperature at or close to the melting point of said organic additive in pure form is 1-70% (by weight) of said organic additive in the coating layer.

15. A medical device according to claim 2, wherein 20-100% (by weight) of the particulate coating layer exhibits a melting point which is at a lower temperature than the melting point of the therapeutic agent and the at least one organic additive in pure form.

16. A medical device according to claim 2, wherein at least one organic additive has a molecular weight of less than 750 Da.

17. A medical device according to claim 2, wherein at least one organic additive is independently selected from the list consisting of p-aminobenzoic acid, methyl paraben, caffeine and calcium salicylate.

18. A medical device according to claim 2, wherein the coating layer comprises one organic additive.

19. A medical device according to claim 2, wherein the coating layer comprises two organic additives.

20. A medical device according to claim 2, wherein the coating layer consists of the therapeutic agent and at least one organic additive.

21. A medical device according to claim 2, wherein the coating layer consists of the therapeutic agent and one organic additive.

22. A medical device according to claim 2, wherein the coating layer consists of the therapeutic agent and two organic additives.

23. A medical device according to claim 2, wherein the concentration of the therapeutic agent in the solid coating layer is 5-95% by weight.

24. A medical device according to claim 2, wherein the solid coating layer is applied to a surface of the device which is composed of nylon.

25. A medical device according to claim 2, wherein the solid coating layer is applied to a surface of the device which is composed of ePTFE.

26. A medical device for delivering a therapeutic agent to a tissue, the device having a solid surfactant-free particulate coating layer applied to an exterior surface of the device, the coating layer comprising a therapeutic agent and at least one non-polymeric organic additive which is hydrolytically stable; wherein the particulate coating layer comprises a mixture of components (a) the therapeutic agent and at least one non-polymeric organic additive in a form which melts as a single phase at a lower temperature than the melting point of the therapeutic agent and the at least one non-polymeric organic additive when in pure form and (b) the at least one non-polymeric organic additive in a form which melts at a temperature at or close to that of said organic additive in pure form; wherein the therapeutic agent is paclitaxel; wherein the therapeutic agent, when formulated in the coating layer, is stable to ethylene oxide sterilization; wherein the coating layer comprises crystalline particles of the therapeutic agent and the at least one non-polymeric organic additive in co-crystalline form, and wherein the at least one non-polymeric organic additive which is hydrolytically stable is selected from the group consisting of p-aminobenzoic acid, methyl paraben, caffeine, and calcium salicylate.

27. A medical device according to claim 26, wherein the proportion of the at least one organic additive in component (b) is 1-70% by weight of said organic additive in the coating layer.

28. A medical device according to claim 2, wherein an adherent layer is interposed between the solid coating layer comprising the therapeutic agent and the at least one organic additive, and the material of the surface of the device.

29. A medical device according to claim 2, comprising a protective top-coat layer applied to the solid coating layer comprising the therapeutic agent and the at least one organic additive.

30. A medical device according to claim 2, which is a balloon catheter.

31. A medical device according to claim 2, which is a stent.

32. A medical device according to claim 2, which is a stent-graft.

33. A medical device according to claim 2, which is a graft.

34. A medical device according to claim 2, which coating layer comprising the therapeutic agent and the at least one organic additive has suitable adherence such that less than 40% of the paclitaxel is lost during shaking using Test Method C.

35. A medical device according to claim 30 wherein the coating has suitable paclitaxel release and tissue transfer characteristics such that the measured drug concentration in the tissue at the 1 hr timepoint is at least 50 µg drug per g tissue (µg/g), using Test Method A.

36. A medical device according to claim 31 wherein the coating has paclitaxel release and tissue transfer characteristics such that the measured drug concentration in the tissue at the 24 hr timepoint is at least 1 µg drug per g tissue (µg/g), using Test Method B.

37. A medical device according to claim 2, wherein at least 80%, of the therapeutic agent chemical content is retained following sterilization using Test Method D.

38. A medical device according to claim 2, for use in the prevention or treatment of stenosis or restenosis in a blood vessel of the human body.

39. A sterilized medical device according to claim 2.

40. A sterilized medical device according to claim 39, which has been ethylene oxide sterilized.

* * * * *